US006994962B1

(12) United States Patent
Thilly

(10) Patent No.: US 6,994,962 B1
(45) Date of Patent: Feb. 7, 2006

(54) METHODS OF IDENTIFYING POINT MUTATIONS IN A GENOME

(75) Inventor: William G. Thilly, Winchester, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/503,758

(22) Filed: Feb. 14, 2000

Related U.S. Application Data

(63) Continuation of application No. PCT/US99/29379, filed on Dec. 9, 1999.

(60) Provisional application No. 60/111,457, filed on Dec. 9, 1998.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.2; 536/23.1; 536/24.3

(58) Field of Classification Search .............. 435/6, 435/91.1; 536/23.1, 24.3
See application file for complete search history.

(56) References Cited

U.S. PATENT DOCUMENTS

| | | | |
|---|---|---|---|
| 5,045,450 A | 9/1991 | Thilly et al. ................... 435/6 |
| 5,633,129 A | 5/1997 | Karger et al. | |
| 5,837,832 A | 11/1998 | Chee et al. ................ 536/22.1 |
| 5,976,842 A | 11/1999 | Wurst | |
| 2002/0132244 A1 | 9/2002 | Li-Sucholeiki | |
| 2003/0092021 A1 | 5/2003 | Thilly | |
| 2003/0143584 A1 | 7/2003 | Li-Sucholeiki | |

FOREIGN PATENT DOCUMENTS

| WO | WO91/00925 | 1/1991 |
|---|---|---|
| WO | WO95/21268 | 8/1995 |
| WO | WO 00/34652 | 6/2000 |

OTHER PUBLICATIONS

Khrapko, K. et al., "Constant denaturant capillary electrophoresis (CDCE): a high resolution approach to mutational analysis", Nucl. Acids Res. vol. 22, pp. 364-369 (1994).*
Davies, K. E. et al., "Molecular Basis of Inherited Disease", IRL Press, New York, pp, 21-25 (1992).*
Crow, J.F. et al., "Mutation in Human Population", Adv. Hum. Genet., vol. 14, pp. 59-77 (1985).*
Conneally, P. M., "Human Genetic Polymorphisms", Dev. Biol. Stand., vol. 83, pp. 107-110 (1994).*
de la Chapelle, A., "Disease gene mapping in isolated human populations; the example of Finland", J. Med. Genet., vol. 30, pp 857-865 (1993).*

Cavalli-Sforza, L. L. et al. "The Genetics of Human Populations", W. H. Freeman and Company, San Francisco, pp. 71-110 (1971).*
Hardelin, J-P. et al., "Heterogeneity in the mutations responsible for X-chromosome linked Kallman syndrome", Hum. Mol. Genetics, vol. 2, pp. 373-377 (1993).*
Cooper, D. N. et al., "The mutational spectrum of single base-pair substitutions causing human genetic disease: patterns and predictions", Hum. Genetics, vol. 85, pp. 55-74 (1990).*
Maraglione, M. et al., "Prevalence of Apolipoprotein E Alleles in Healthy Subjects and Survivors of Ischemic Stroke", Stroke, vo 29, pp. 399-403 (Feb. 1998).*
Paik, Y-K. et al., "Nucleotide sequence and structure of the human apolipoprotein E gene", PNAS, vol. 82, pp. 3445-3449 (1985).*
de Knijff, P. et al., "Genetic Heterogeneity of Apolipoprotein E and Its Influence on Plasma Lipid and Lipoprotein Levels", Hum. Mut., pp. 178-194 (1994).*
Bjorheim J. et al., "Mutations analyses of KRAS exon 1 comparing three different techniques: temporal temperature gradient electrophoresis, constant denaturant capillary electrophoresis and allele specific polymerase chain reaction." *Mut. Res.*, 403:103-12 (Jul. 1998).
Ekstrom P.O., et al., "Detection of low-frequency mutations in exon 8 of the TP53 gene by constant denaturant capillary electrophesis (CDCE) ." *Biotechniques*, 27:128-34 (Jul. 1999).
Ekstrom, P.O., et al., "Two-point fluorescence detection and automated fraction collection applied to constant denaturant capillary electrophoresis." *Biotechniques*, 29:582-4, 586-9 (Sep. 2000).
Falt S., et al., "Identification of in vivo mutations in exon 5 of the human HPRT gene in a set of pooled T-cell mutants by constant denaturant capillary electrophoresis (CDCE) ." *Mutat. Res.*, 452:57-66 (Jul. 2000).
Fischer & Lerman, "Separation of random fragments of DNA according to properties of their sequences." *Proc. Natl. Acad. Sci. USA*, 77:4420-4424 (1980).

(Continued)

*Primary Examiner*—Jeffrey Fredman
*Assistant Examiner*—Teresa Strzelecka
(74) *Attorney, Agent, or Firm*—Hamilton, Brook, Smith & Reynolds, P.C.

(57) ABSTRACT

The invention relates to a method for identifying inherited point mutations in a targeted region of the genome in a large population of individuals and determining which inherited point mutations are deleterious, harmful or beneficial. Deleterious mutation are identified directly by a method of recognition using the set of point mutations observed in a large population of juveniles. Harmful mutations are identified by comparison of the set of point mutation observed in a large set of juveniles and a large set of aged individuals of the same population. Beneficial mutations are similarly identified.

11 Claims, 24 Drawing Sheets

OTHER PUBLICATIONS

Fischer & Lerman, "DNA fragments differing by single base-pair substitutions are separated in denaturing gradient gels: Correspondence with melting theory." *Proc. Natl. Acad. Sci. USA*, 80:1579-1583 (1983).

Galinsky, D., et al., "Analysis of the apo E/apo C-I, angiotensin converting enzyme and methylenetetrahydrofolate reductase genes as candidates affecting human longevity." *Atherosclerosis*, 129:177-183 (1997).

Gross et al., "A comparison of BRCA1 mutation analysis by direct sequencing, SSCP and DHPLC." *Hum. Genet.,* 105: 72-78 (1999).

Herrero-Jimenez, P., et al., "Mutation, cell kinetics, and subpopulations at risk for colon cancer in the United States." *Mutat.Res.,* 400:553-78 (May 1998).

Herrero-Jimenez, P., et al., "Population risk and physiological rate parameters for colon cancer. The union of an explicit model for carcinogenesis with the public health records of the United States." *Mut. Res.,* 447:73-116 (Jan. 2000).

Hovig et al., "Constant denaturant gel electrophoresis, a modification of denaturing gradient gel electrophoresis, in mutations detection." *Mut. Res.,* 262:63-71 (1991).

Kervinen, K., et al., "Apolipoprotein E and B polymorphism: Longevity factors assessed in nonagenarians." *Atherosclerosis*, 105:89-95 (1994).

Khrapko K., et al., "Mutational spectrometry without phenotypic selection:human mitochondrial DNA." *Nucleic Acids Res.,* 25:685-693 (1997).

Khrapko K., et al., "Identification of point mutations in mixtures by capillary electrophoresis hybridization." *Nucleic Acids Res.,* 26:5738-40 (Dec. 1998).

Li-Sucholeiki, X.C., et al., "Applications of constant denaturant capillary electrophoresis/high-fidelity polymerase chain reaction to human genetic analysis." *Electrophoresis*, 20:1224-32 (Jun. 1999).

Li-Sucholeiki, X.C., et al., "A sensitive scanning technology for low frequency nuclear point mutations in human genomic DNA." *Nucleic Acids Res.,* 28:E44 (May 2000).

Muniappan, B.P., et al., "Application of constant denaturant capillary electrophoresis (CDCE) to mutation detection in humans." *Genet. Anal.* 14:221-7 (Feb. 1999).

Tomita-Mitchell, A., et al., "Mismatch repair deficient human cells: spontaneous and MNNG-induced mutational spectra in the HRPT gene." *Mut. Res.,* 450:125-38 (May 2000).

Tomita-Mitchell, A., et al., "Single nucleotide polymorphism spectra in newborns and centenarians: identification of genes coding for rise of mortal disease." *Gene* 223:381-391 (1998).

Cariello, N. et al., "Resolution of a Missense Mutant in Human Genomic DNA by Denaturing Gradient Gel Electrophoresis and Direct Sequencing Using In Vitro Amplification: $HPRT_{Munich}$," *Am. J. Hum. Genet.,* 42:726-734 (1988).

Coller, H. et al., "Mutational Spectra of a 100-Base Pair Mitochondrial DNA Target Sequence in Bronchial Epithelial Cells: A Comparison of Smoking and Nonsmoking Twins[1]," *Cancer Res.,* 58:1268-1277 (1998).

Harris, C., "p53: At the Crossroads of Molecular Carcinogenesis and Risk Assessment," *Science*, 262:1980-1981 (1993).

Khrapko, K. et al., "Mitochondrial mutational spectra in human cells and tissues," *Proc. Natl. Acad. Sci. USA*, 94:13798-13803 (1997).

Khrapko, K. et al., "Mutational Spectrometry: Means and Ends," *Prog. Nucleic Acid Res. Mol. Biol.*, 49:285-311 (1994).

Lerman, L. and Silverstein, K., "Computational Simulation of DNA Melting and Its Application to Denaturing Gradient Gel Electrophoresis," *Meth. Enzymol.,* 155:482-501 (1987).

Li, X. and Thilly, W., "Use of wide-bore capillaries in constant denaturant capillary electrophoresis," *Electrophoresis*, 17:1884-1889 (1996).

Li-Sucholeiki, X. and Thilly, W., "A sensitive scanning technology for low frequency nuclear point mutations in human genomic DNA," *Nuc. Acids Res.*, 28:i-viii (2000).

Miller, J., "Mutational Specificity in Bacteria," *Annu. Rev. Genet.*, 17:215-238 (1983).

Miller, R. and Riblet, R., "Improved phenol emulsion DNA reassociation technique (PERT) using thermal cycling," *Nucl. Acids. Res.,* 23:2339-2340 (1995).

Robinson, D. et al., "An analysis of in vivo hprt mutant frequency in circulating T-lymphocytes in the normal human population: a comparison for four datasets," *Mut. Res.,* 313:227-247 (1994).

Thilly, W., "Mutational Spectrometry in Animal Toxicity Testing," *Annu. Rev. Pharmacol. Toxicol.*, 30:369-385 (1990).

* cited by examiner

Fig. 7A
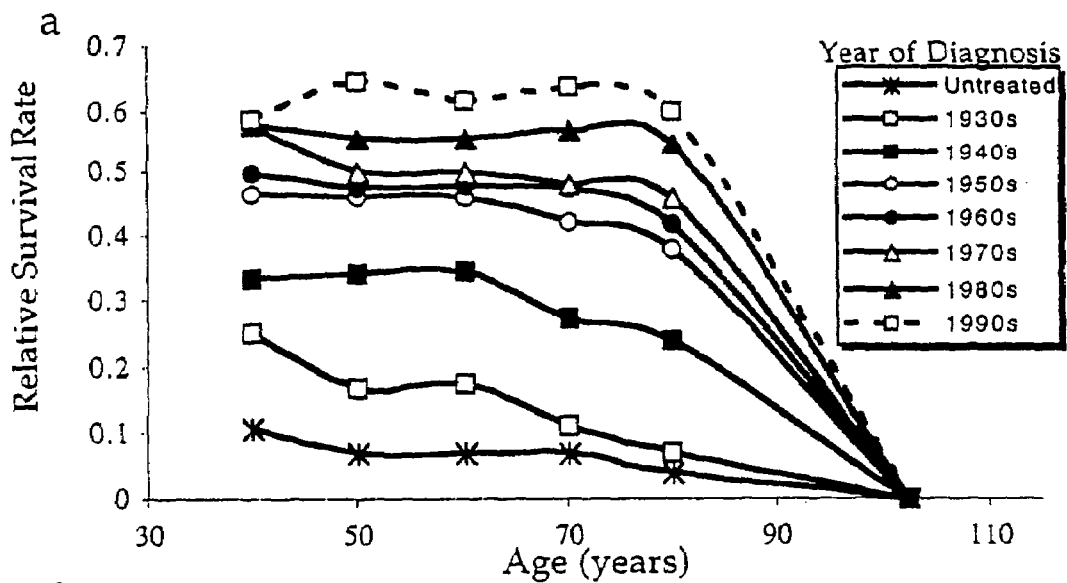
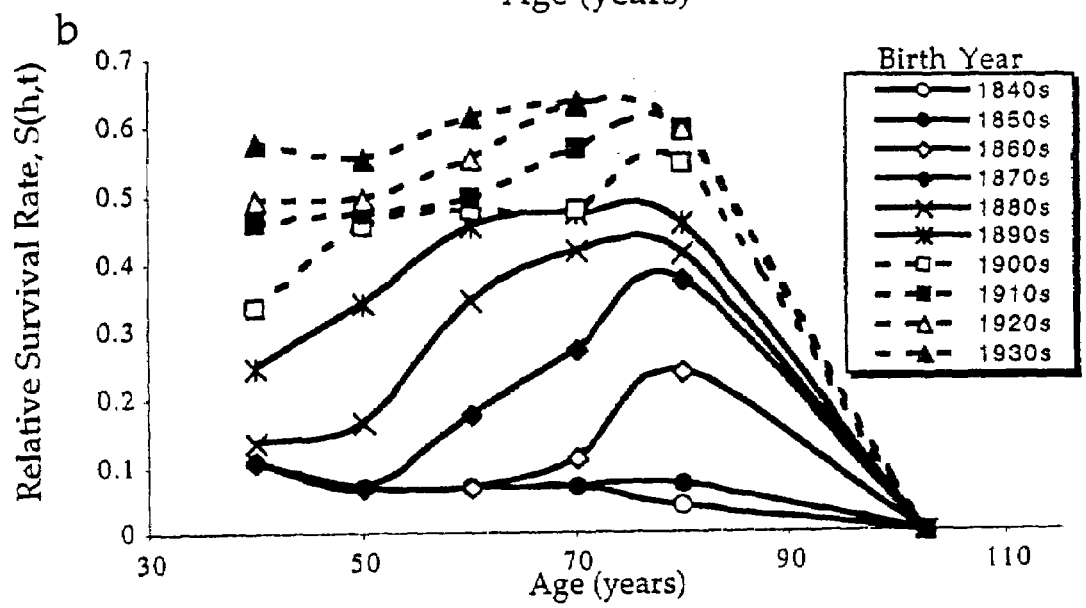
Fig. 7B

Fig. 10A
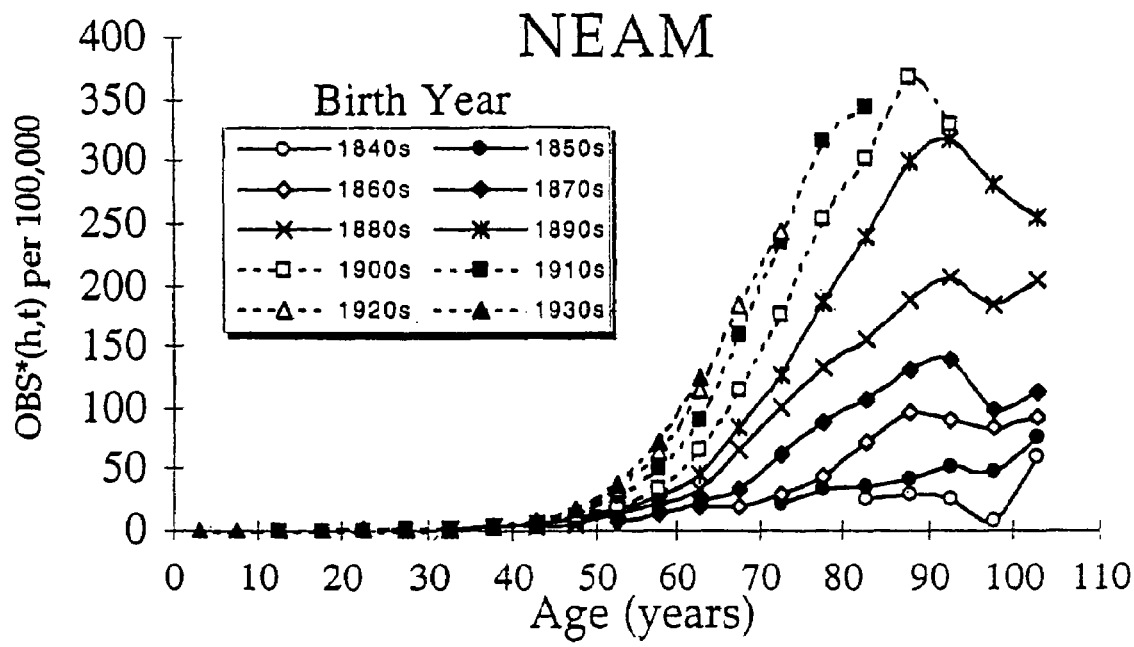
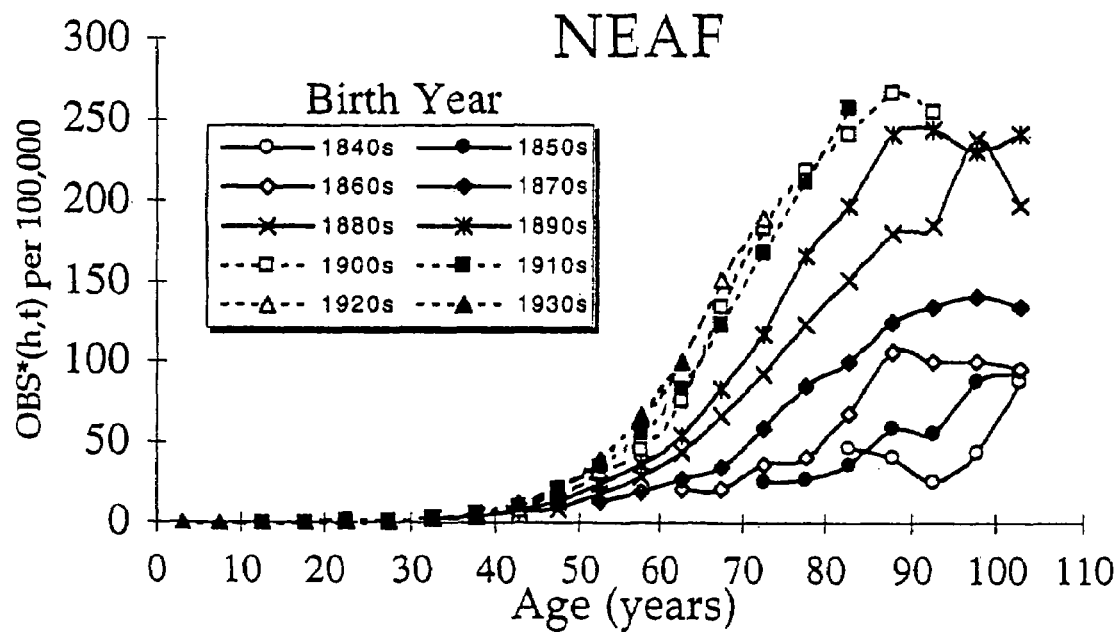
Fig. 10B $G = F(h,t)_{genetic}$     $\overline{G} = (1 - G) = $ not in $F(h,t)_{genetic}$
$E_h = F(h,t)_{environmental}$     $\overline{E}_h = (1 - E_h) = $ not in $F(h,t)_{environmental}$ Fig. 20A
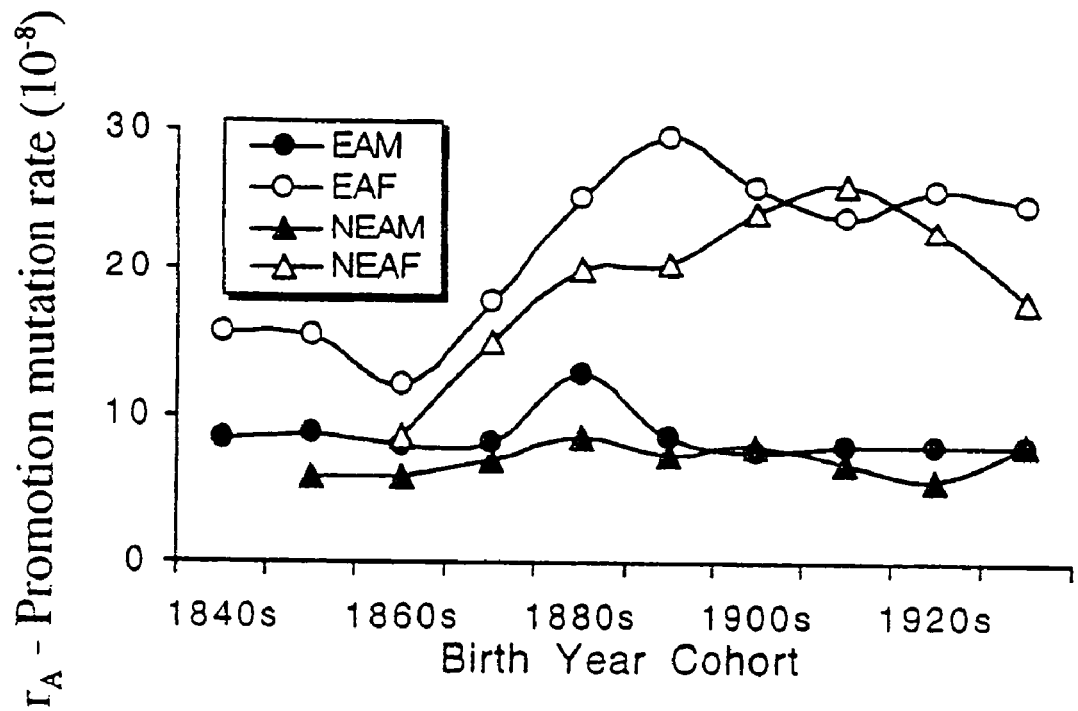
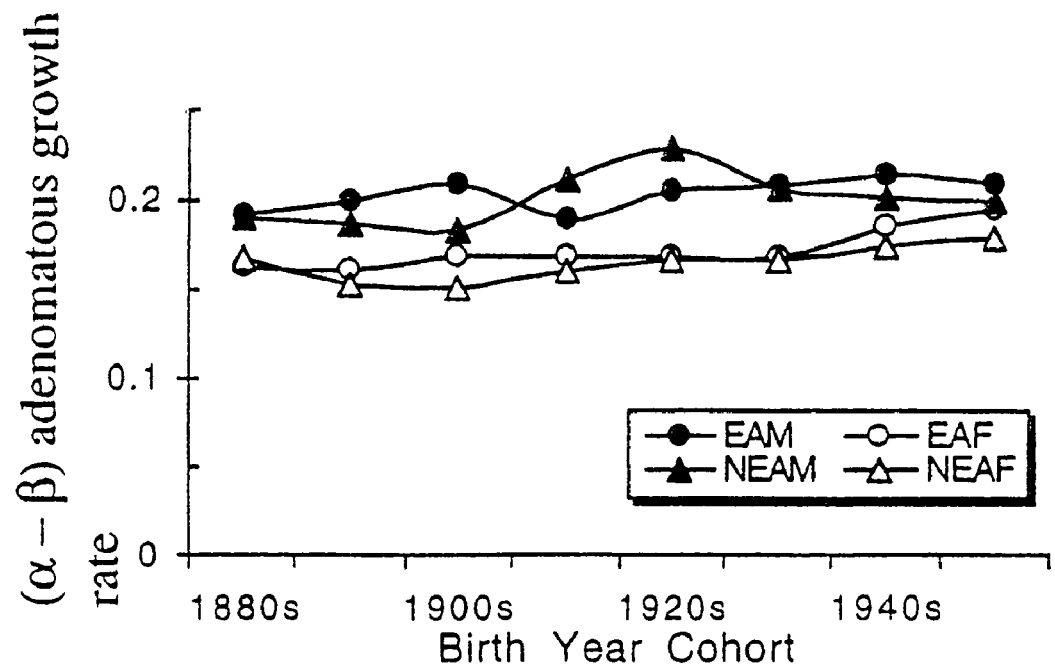
Fig. 20B

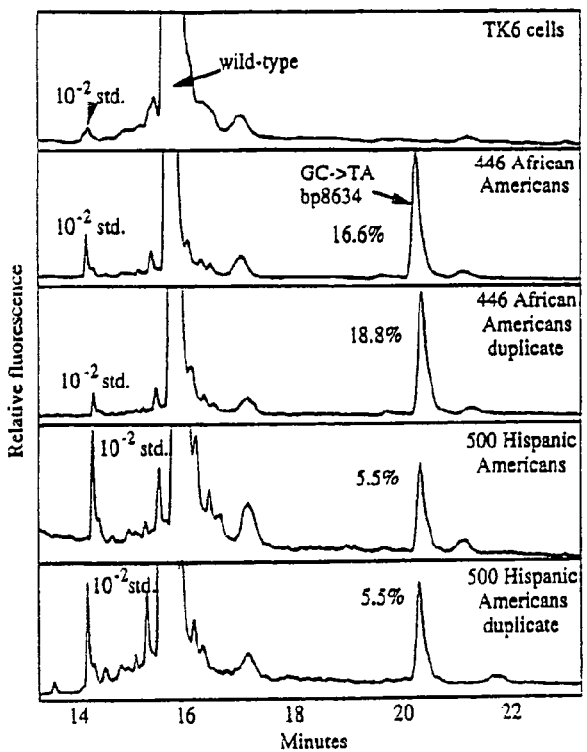
Fig. 25
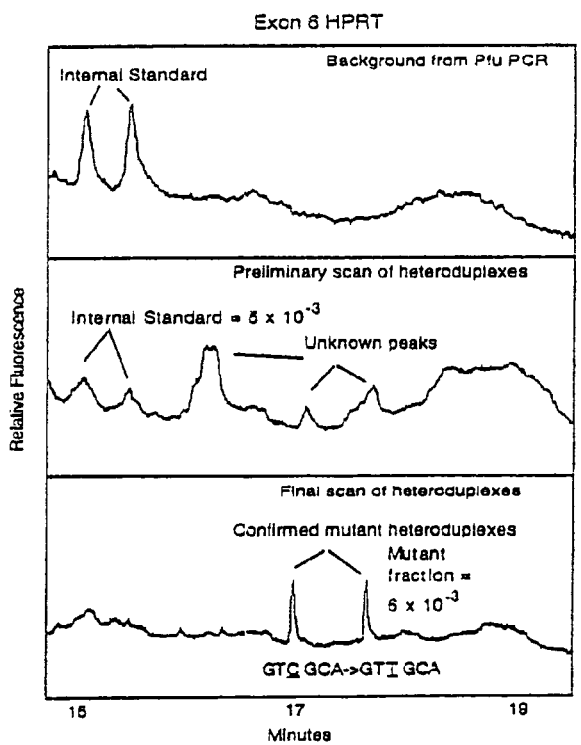
Fig. 26A
Fig. 26B
Fig. 26C

Fig. 27
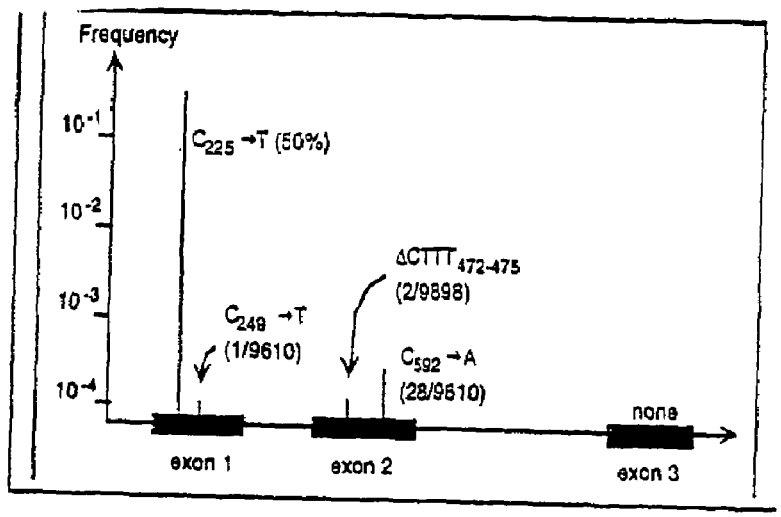
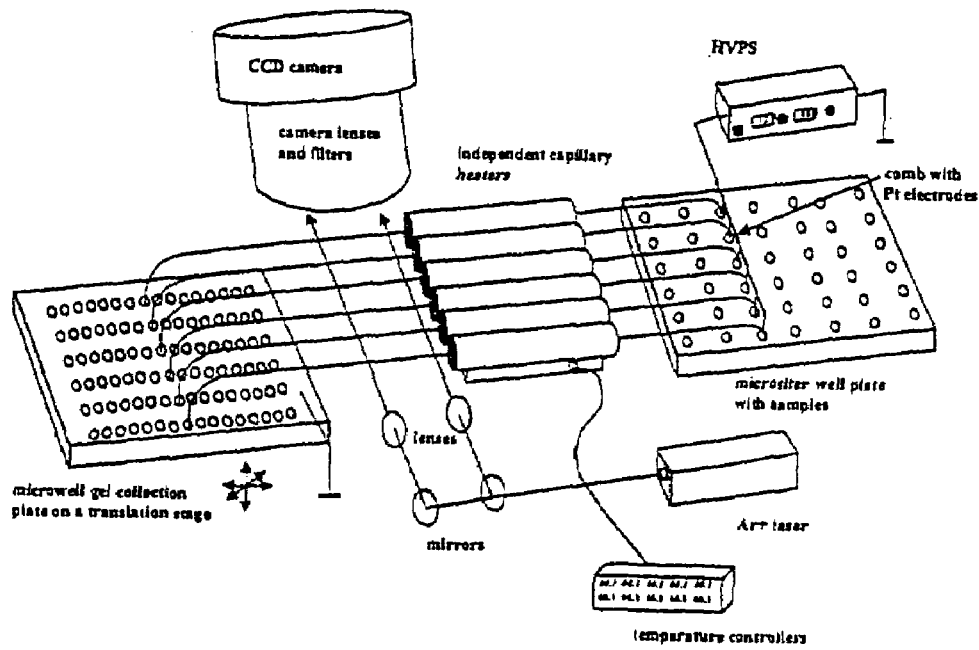
Fig. 28

Fig. 29
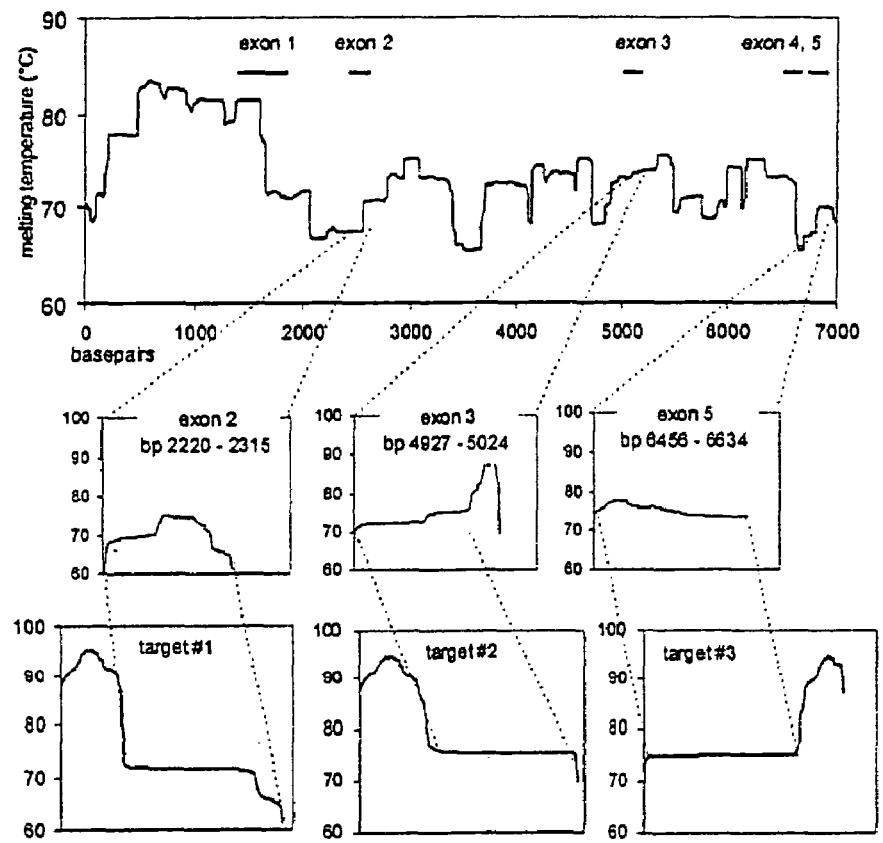
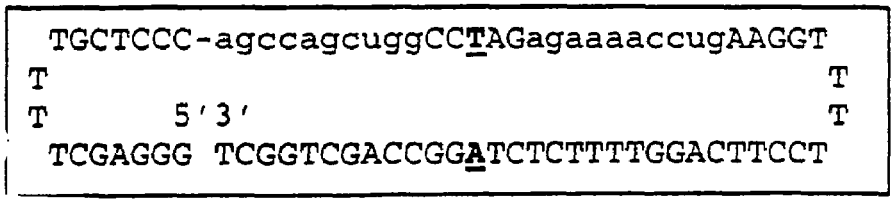
Fig. 30

METHODS OF IDENTIFYING POINT MUTATIONS IN A GENOME

RELATED APPLICATION

This application is a continuation of PCT/US99/29379, filed Dec. 9, 1999, which claims the benefit of U.S. Provisional Application No. 60/111,457, filed Dec. 9, 1998. The entire teachings of each of the foregoing patent applications are incorporated herein by reference.

GOVERNMENT SUPPORT

The invention was supported, in whole or in part, by grants P30-ES02109, P01-ES07168, and P42-ES04675, from grants from the National Institute of Environmental Health Sciences, U.S.A. The Government has certain rights in the invention.

BACKGROUND OF THE INVENTION

In the last year, the National Institutes of Health (U.S.A.) has allocated $36 million in a 3-year program to find 100,000 human single-nucleotide polymorphisms (SNPs) (Masood, E., 1999. Nature. 398:545–546). The SNP Consortium, a group of public and private institutions, has separately committed $45 million in an effort to identify 300,000 SNPs in two years (Wellcome, 1999). Methods currently used to identify SNPs and other mutations include single-strand conformation polymorphism (SSCP; Orita, M. et al., 1989. Proc. Natl. Acad. Sci. USA. 86:2766–2770), restriction fragment length polymorphism (RFLP; Arnheim et al., 1985. Proc. Natl. Acad. Sci. USA. 82:6970–6974), amplified fragment length polymorphism (AFLP; Yunis, I. et al., 1996. Tissue Antigens. 38:78–88), micro- and minisatellite variation (Koreth, J. et al., 1996. J. Pathol. 178: 239–248), allele-specific hybridization (Shuber, A. et al., 1997. Human Mol. Genet. 6:337–347), denaturing gradient gel electrophoresis (DGGE; Guldberg, P. and Guttler, F., 1993. Nucl. Acids Res. 21:2261–2262), DNA chips with detection by fluorescence or mass spectrometry (Chee et al., 1996. Science. 274:610–614; Cargill, M. et al., 1999. Nat. Genet. 22:231–238; Hacia, J. et al., 1999. Nat. Genet. 22:164–167; Griffin, T. et al., 1999. Proc. Natl. Acad. Sci. USA. 96:6301–6306; Li et al., 1999) and direct sequencing. Another approach is direct sequencing of the genome.

The techniques listed above all require assaying each individual separately, or small pools of at most about a dozen individuals (Trulzsch, B. et al., 1999. Biotechniques. 27:266–268). Since the cost per individual is not trivial, this makes mutation discovery in large populations very expensive. However, such studies are required for determination of low-frequency point mutations with useful statistical precision (Hagmann, M., 1999. Science. 285:21–22).

A need exists for a method of identifying low-frequency inherited point mutations in large populations.

SUMMARY OF THE INVENTION

The invention relates to a method for identifying inherited point mutations in a target region of a genome, comprising providing a pool of DNA fragments isolated from a population, and a) amplifying said target region of each of said fragments in a high fidelity polymerase chain reaction (PCR) under conditions suitable to produce double stranded DNA products which contain a terminal high temperature isomelting domain that is labeled with a detectable label, and where the mutant fraction of each PCR-induced mutation is not greater than about $5 \times 10^{-5}$; b) melting and reannealing the product of a) under conditions suitable to form duplexed DNA, thereby producing a mixture of wild-type homoduplexes and heteroduplexes which contain point mutations; c) separating the heteroduplexes from the homoduplexes based upon the differential melting temperatures of said heteroduplexes and said homoduplexes and recovering the heteroduplexes, thereby producing a second pool of DNA that is enriched in target regions containing point mutations; d) amplifying said second pool in a high fidelity PCR under conditions where only homoduplexed double stranded DNA is produced, thereby producing a mixture of homoduplexed DNA containing wild-type target region and homoduplexed DNAs which contain target regions that include point mutations; e) resolving the homoduplexed DNAs containing target regions which include point mutations based upon the differential melting temperatures of the DNAs, and recovering the resolved DNAs which contain a target region which includes point mutations; and f) sequencing the target region of the recovered DNAs which contain a target region which include point mutations. In particular embodiments, the population can comprise at least about 1000, or at least about 10,000 individuals. In a more particular embodiment the population can comprise between about 10,000 and 1,000,000 individuals. In additional embodiments, the population consists of members of the same demographic group, such as those of European ancestry, African ancestry, Asian ancestry or Indian ancestry. In a preferred embodiment, the pool of fragments is enriched in fragments containing the target region. The heteroduplexes can be separated from the homoduplexes in c), and the homoduplexed DNAs can be resolved in d) by constant denaturing gel capillary electrophoresis, constant denaturing gel electrophoresis, denaturing gradient gel electrophoresis or denaturing high performance liquid chromatography. The target region can be any desired region of the genome, such as a portion of a protein or RNA encoding gene. The target region can be from about 80 to about 3,000 base pairs (bp). In one embodiment, the target region is an isomelting domain. In other embodiments, the target region is about 80 to about 1000 bp or about 100 to about 500 bp.

The invention also relates to a method for identifying genes which carry a harmful allele. In one embodiment the method comprises: a) identifying the inherited point mutations which are found in the genes or portions thereof of a population of young individuals, determining the frequencies with which each point mutation occurs, and calculating the sum of the frequency of all point mutations identified for each gene or segment; b) identifying the inherited point mutations which are found in the genes or portions thereof of a population of aged individuals, determining the frequencies with which each point mutation occurs, and calculating the sum of the frequencies of all point mutations identified for each gene or segment; c) comparing the sum frequency of point mutations which are found in a selected gene or portion thereof of the young population calculated in a) with the sum frequency of point mutation which are found in the same gene or portion thereof of the aged population calculated in b), wherein a significant decrease in the sum frequency of point mutations in the aged population indicates that said selected gene carries a harmful allele.

In another embodiment, the method for identifying genes which carry a harmful allele, comprises: a) identifying the inherited point mutations which are found in the genes or portions thereof of a population of young individuals, and determining the frequencies with which each point mutation occurs; b) identifying the inherited point mutations which are found in the genes or portions thereof of a population of aged individuals, and determining the frequency with which each point mutation occurs; and c) comparing the frequency of each point mutation identified in a selected gene or portion thereof of the young population determined in a) with the frequency of the same point mutations identified in said selected gene of the aged population determined in b), wherein a significant decrease in the frequency of two or more point mutations in said selected gene of the aged population relative to said selected gene of the young population indicates that said selected gene carries a harmful allele. In a particular embodiment, the method further comprises: d) determining the frequency of said two or more point mutations which decrease in the aged population in said selected gene of one or more intermediate age-specific populations; e) determining the age-specific decline of said two or more point mutations; and f) comparing the age-specific decline determined in e) with the theoretical age-specific decline of harmful alleles which cause mortal diseases, $X(h,t)$, and determining if the functions are significantly different, wherein a determination that the age-specific decline determined in e) is not significantly different from the theoretical age-specific decline of harmful alleles which cause one or more mortal diseases further indicates that said selected gene carries a harmful allele and has a high probability of being causal of said one or more mortal diseases. In additional embodiments the invention further comprises: g) determining the frequency of said two or more point mutations which decrease in the aged population in said selected gene of one or more proband populations; and h) comparing the frequencies of said two or more point mutations in said selected gene or portion thereof in the young population with the frequencies of said two or more point mutations in said selected gene or portion thereof in the proband populations; wherein a significant increase in the frequencies of said one or more point mutations in the proband population relative to the young population indicates that said gene caries a harmful allele that plays a causal role in said disease; or g) determining the frequency of said two or more point mutations which decrease in the aged population in said selected gene of one or more proband populations consisting of individuals with early onset disease; and h) comparing the frequencies of said two or more point mutations in said selected gene or portion thereof in the young population with the frequencies of said two or more point mutations in said selected gene or portion thereof in the proband populations; wherein a significant increase in the frequencies of said one or more point mutations in the proband population relative to the young population indicates that said gene carries a harmful allele which is a secondary risk factor which accelerates the appearance of disease.

The invention also relates to a method for identifying genes which carry a harmful allele or which are linked to a gene that carries a harmful allele. In one embodiment the method comprises: a) identifying the inherited point mutations which are found in the genes or portions thereof of a population of young individuals, and determining the frequency with which each point mutation occurs; b) identifying the inherited point mutations which are found in the genes or portions thereof of a population of aged individuals, and determining the frequency with which each point mutation occurs; and c) comparing the frequency of each point mutation identified in a selected gene or portion thereof of the young population determined in a) with the frequency of the same point mutations identified in said selected gene of the aged population determined in b), wherein a significant decrease in the frequency of a point mutation in said selected gene of the aged population relative to said selected gene of the young population indicates that said selected gene carries a harmful allele or is linked to a gene that carries a harmful allele.

In another embodiment, the invention relates to a method for identifying genes which carry a harmful allele or which are linked to a gene that carries a harmful allele comprising: a) identifying the inherited point mutations which are found in the genes or portions thereof of an early onset proband population, and determining the frequency with which each point mutation occurs; b) identifying the inherited point mutations which are found in the genes or portions thereof of a late onset proband population, and determining the frequency with which each point mutation occurs; and c) comparing the frequencies of point mutations which are found in a selected gene or portion thereof in the early onset proband population with the frequencies of the same point mutations in said selected gene or portion thereof of the late onset proband populations; wherein a significant increase in the frequencies of one or more point mutations in the early onset proband population relative to the late onset proband population indicates that said gene carries a harmful allele which is a secondary risk factor which accelerates the appearance of disease.

The invention also relates to a method of identifying genes which carries a harmful allele that is a secondary risk factor that accelerates the appearance of a disease. In one embodiment the method comprises: a) identifying the inherited point mutations which are found in the genes or portions thereof of an early onset proband population, determining the frequency with which each point mutation occurs, and calculating the sum of the frequency of all point mutations identified for each gene or segment; b) identifying the inherited point mutations which are found in the genes or portions thereof of a late onset proband population, and determining the frequency with which each point mutation occurs, and calculating the sum of the frequency of all point mutations identified for each gene or segment; and c) comparing the sum frequency of point mutations which are found in a selected gene or portion thereof of the early onset proband population calculated in a) with the sum frequency of point mutation which are found in the same gene or portion thereof of the late onset proband population calculated in b), wherein a significant decrease in the sum frequency of point mutations in the late onset proband population indicates that said selected gene carries a harmful allele which is a secondary risk factor that accelerates the appearance of a disease.

The invention also relates to a method for identifying genes which carry an allele which increases longevity, comprising: a) identifying the inherited point mutations which are found in the genes or portions thereof of a population of young individuals, determining the frequencies with which each point mutation occurs, and calculating the sum of the frequency of all point mutations identified for each gene or segment; b) identifying the inherited point mutations which are found in the genes or portions thereof of a population of aged individuals, determining the frequencies with which each point mutation occurs, and calculating the sum of the frequencies of all point mutations identified for each gene or segment; and c) comparing the sum frequency of point mutations which are found in a selected gene or portion thereof of the young population calculated in a) with the sum frequency of point mutation which are found in the same gene or portion thereof of the aged population calculated in b), wherein a significant increase in the sum frequency of point mutations in the aged population indicates that said selected gene carries an allele which increases longevity.

In another embodiment, the method for identifying genes which carry an allele which increases longevity comprises: a) identifying the inherited point mutations which are found in the genes or portions thereof of a population of young individuals, and determining the frequencies with which each point mutation occurs; b) identifying the inherited point mutations which are found in the genes or portions thereof of a population of aged individuals, and determining the frequency with which each point mutation occurs; and c) comparing the frequency of each point mutation identified in a selected gene or portion thereof of the young population determined in a) with the frequency of the same point mutations identified in said selected gene of the aged population determined in b), wherein a significant increase in the frequency of two or more point mutations in said selected gene of the aged population relative to said selected gene of the young population indicates that said selected gene carries an allele which increases longevity.

In a further embodiment, the method for identifying genes which carry an allele which increases longevity or which are linked to a gene that increases longevity comprises: a) identifying the inherited point mutations which are found in the genes or portions thereof of a population of young individuals, and determining the frequency with which each point mutation occurs; b) identifying the inherited point mutations which are found in the genes or portions thereof of a population of aged individuals, and determining the frequency with which each point mutation occurs; and c) comparing the frequency of each point mutation identified in a selected gene or portion thereof of the young population determined in a) with the frequency of the same point mutations identified in said selected gene of the aged population determined in b), wherein a significant increase in the frequency of a point mutation in said selected gene of the aged population relative to said selected gene of the young population indicates that said selected gene carries an allele which increases longevity or is linked to a gene that increases longevity.

The invention also relates to a method for identifying genes which affect the incidence of a disease, comprising: a) identifying the inherited point mutations which are found in genes or portions thereof of a population of young individuals not afflicted with said disease, determining the frequencies with which each point mutation occurs, and summing the frequency of all point mutations identified in each gene or segment thereof; b) identifying the inherited point mutations which are found in genes or portions thereof of a proband population having said disease, determining the frequencies with which each point mutation occurs, and summing the frequency of all point mutations identified in each gene or segment thereof; and c) comparing the sum frequency of point mutation in a selected gene or portion thereof in the young population with the sum frequency of point mutations in said selected gene or portion thereof in the proband population; wherein a significant increase in the sum frequency of point mutations in the proband population indicates that said gene plays a causal role in said disease.

The invention also relates to a method for identifying a gene which carries deleterious alleles. In one embodiment, the method comprises: a) identifying the inherited point mutations occurring in any exon(s) and splice sites of said gene of a population of young individuals; b) identifying the subset of point mutations in a) that are obligatory knockout point mutations, and determining the frequencies with which each obligatory knockout point mutation occurs; and c) summing the frequency of all obligatory knockout point mutations identified in the gene; wherein a sum frequency of less than about 2% indicates that said gene carries a deleterious allele.

In another embodiment, the method comprises: a) identifying the inherited point mutations occurring in any exon(s) and splice sites of said gene of a population of young individuals; b) identifying the subset of point mutations in a) that are obligatory knockout point mutations, and determining the frequencies with which each obligatory knockout point mutation occurs; c) identifying the subset of point mutations in a) that are presumptive knockout point mutations, and determining the frequencies with which each presumptive knockout point mutation occurs; and d) summing the frequency of all of said obligatory knockout point mutations and presumptive knockout point mutations identified in the gene; wherein a sum frequency of less than about 2% indicates that said gene carries a deleterious allele.

In one embodiment, a sum of about 0.02% to about 2% indicates that said gene carries a recessive deleterious allele. In another embodiment, a sum of less than about 0.02% indicates that said gene carries a dominant deleterious allele. A sum of greater than 2% suggests that the said gene carries no deleterious alleles.

The invention also relates to a method for isolating and identifying a target region of a genome which contains inherited point mutations.

The invention further relates to an isolated nucleic acid which is complimentary to a strand of a gene or allele thereof identified by the methods described herein.

The invention also relates to arrays of isolated nucleic acids of the invention which are immobilized on a solid support.

The present invention further relates to an isolated nucleic acids and an array of isolated nucleic acids described herein for use in therapy (including prophylaxis) or diagnosis, and to the use of such nucleic acids for the manufacture of a medicament for the treatment of a particular disease or condition as described herein.

BRIEF DESCRIPTION OF THE DRAWINGS

FIGS. 3B–3E) and polygenic (n=2; FIGS. 3C–3F) risks in pancreatic cancer analyzed for populations of 10,000 in the preceding section. It is clear by inspection that a sample of 1000 would permit discrimination among newborn, proband and centenarian populations for a polymorphism occurring at the expected frequency at the 95% confidence level for the case of simple monogenic inheritance but not for multigenic or polygenic risk factors. The number of genes involved for each of these cases is denoted by "n". These confidence limits apply to the case of one and only one point mutation compared among the three population groups.

FIG. 6A) and Non-European-American females primarily of African-American descent (NEAF; FIG. 6B; data recorded 1930–1992).

FIGS. 7A and 7B are graphs which demonstrate age-specific relative survival rates of colon cancer for European-American females by year of diagnosis (FIG. 7A) and by year of birth (FIG. 7B).

FIGS. 10A and 10B are graphs of colon cancer age- and birth year-specific mortality curves adjusted for historical changes in under-reporting and survival rates among Non-European Americans males (FIG. 10A) and Non-European Americans females (FIG. 10B). OBS*(h,t)=OBS(h,t)÷[R(h, t) (1−S(h,t))]

FIGS. 20A and 20B are graphs demonstrating promotion mutation rate, $r_A$, (FIG. 20A) and the adenomatous growth rate, (α–β), (FIG. 20B) for EAM, EAF, NEAM and NEAF as a function of year of birth.

FIG. 22B: mutants 1–15 are nearly all G/C→A/T transitions (1, 10 and 12 are G/C→T/A transversions). Measured peak mutant fractions such as in peaks a–n are in the range of 0.5 to $2 \times 10^{-6}$. Fractions of true mutants above this background are observed, isolated and sequenced as seen for MNNG induced mutants 1–15.

FIG. 23A shows the laser-induced fluorescence (LIF) detection trace of the separation of the fragments in one of the capillaries of the array. The fractions were collected in time intervals depicted by the vertical marks on the electropherogram. FIG. 23B shows the LIF detection traces of the fractions recovered from the collection gel well plate used in (FIG. 23A) and reinjected. The off scale peak corresponds to fluorescein, used as an internal standard. The collected fractions were membrane-desalted prior to reinjection.

FIG. 25 is a series of electropherograms demonstrating the results of CDCE/hifiPCR analysis of pooled samples of juveniles from two ethnic backgrounds. This APC gene exon 15 G→T transversion at bp 8634 is found to be significantly higher in the African-American than in the Hispanic-American group.

FIGS. 26A–26C are electropherograms obtained in a study of blood samples from 446 African-American juveniles which were pooled and analyzed for inherited point mutations in exon 6 and 9-bp of its adjacent splice sites. PCR background studies (FIG. 26A) indicated a single mutant allele would be detected at fractions of $5 \times 10^{-5}$ or higher. The preliminary scan in which true mutant/wild-type heteroduplexes would be mixed with non-mutant noise peaks is shown in the second panel with a quantitative internal control peak (FIG. 26B). Isolation of the raw heteroduplex sample followed by high-fidelity PCR produced a clear electropherogram containing one and only one pair of peaks which could have arisen as a mutant in the original pooled sample (FIG. 26C). Subsequent isolation and sequencing showed this mutant to be a "wobble" transition GTC GCA→GTT GCA (SEQ ID NO:1→SEQ ID NO:2) (Val→Val) which had not been previously reported. It was present in approximately $6 \times 10^{-3}$ of the original 669 Hprt alleles or approximately 4 mutant copies. It was not present in Hispanic-American group (New York City) or the mixed ethnic sample of 2000 juveniles (Boston).

FIG. 27 is a fine structure map of inherited point mutations in the three exons of the human beta globin gene. About 10,000 alleles of the Han Chinese population were screened.

FIG. 28 is a schematic demonstrating a multi-capillary CDCE instrument with fraction collector.

FIG. 29 is a melting map of the human uracil-DNA glycosylase (UNG) gene demonstrating the selection of target sequences that cover three exons. The melting profile is shown only for the first 7000 base pairs (bp) of the genomic UNG sequence.

FIG. 30 illustrates the design of a synthetic DNA/RNA chimera (SEQ ID NO:3) to convert codon 12 of rad54 from AAG (lysine) to TAG (stop). Upper case letters represent DNA nucleotides and lower case 2'-O-methyl RNA nucleotides.

DETAILED DESCRIPTION OF THE INVENTION

Figure 1:
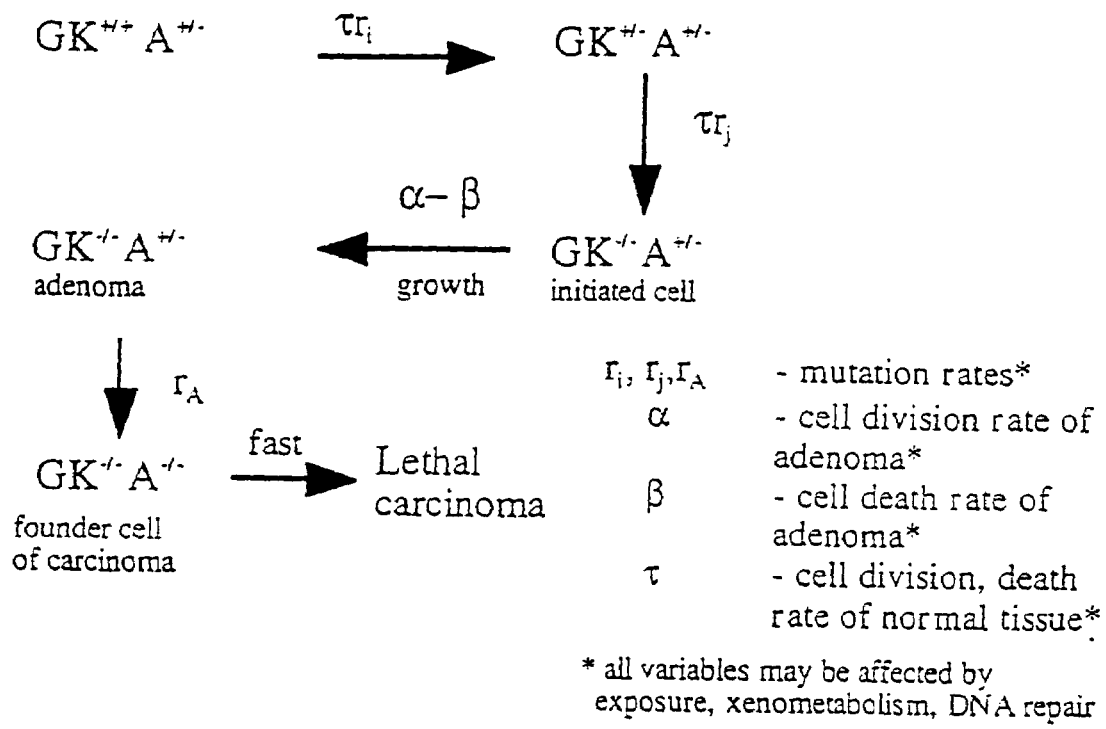
FIG. 1 is a schematic representation of a multi-stage cancer hypothesis for sporadic cancer (Herrero-Jimenez, P. et al., 1998. *Mut. Res.* 400:553–578) where the loss of both alleles of the first gatekeeper gene 'GK' and the remaining active allele of the second gatekeeper gene 'A' are the rate-limiting events. An inherited mutation in gene 'GK' would be expected to lead to early onset familial cancer while an inherited inactivating mutation in one allele of gene 'A', creates a risk of death by sporadic cancer.

The invention relates to a method for identifying inherited point mutations in a targeted region of the genome in a large population of individuals and determining which inherited point mutations are deleterious, harmful or beneficial. Deleterious mutation are identified directly by a method of recognition using the set of point mutations observed in a large population of juveniles. Harmful mutations are identified by comparison of the set of point mutation observed in a large set of juveniles and a large set of aged individuals of the same population. Beneficial mutations are similarly identified.

As used herein, a gene defines a DNA sequence encoding proteins, RNAs or other physiologically functional structures which carry deleterious, harmful or beneficial mutations identified by the presence of point mutations within said deleterious, harmful or beneficial mutations.

The relationship between harmful point mutations in a particular disease (e.g., a mortal disease) can be discovered by a method of comparison of a theoretical age dependent decline of harmful alleles for all particular diseases, and the observed age dependent decline in harmful alleles of a particular gene.

In one aspect, the invention is a method for isolating or identifying inherited point mutations in a target region of a genome. Point mutations are mutations where a small number (e.g., 1–25 or 1–10 or 1–5 or a single base pair) of base pairs are deleted, added or substituted for by a different base (e.g., transitions, transversions). Inherited point mutations are those that are present in the genome of an individual at conception. Generally, the sequence of the target region is known, from public databases such as GenBank. Suitable target sequences can be up to about 3,000 base pairs (bp) long. Target sequences can be from about 80 to about 1000 bp or about 100 to about 500 bp. In particular, target sequences are about 100 bp. In one embodiment the target sequence is an isomelting domain. Suitable target regions can be found throughout the genome. In fact, it is desirable to identify all point mutations in the entire genome using methods described herein. In certain embodiments, the target region is a protein encoding gene or a portion thereof, or an RNA encoding gene or a portion thereof. For example, the target region can be an exon or a protein encoding gene, a regulatory region (e.g., promoter), an intron, or a portion of any of the foregoing. The target region can also span the junction of an exon and an intron of a gene. RNA encoding genes are genes which encode RNA molecules that are not translated into proteins, such as genes encoding ribosomal RNAs, transfer RNAs and ribozymes.

The method for isolating or identifying inherited point mutations in a target region of a genome includes the steps of providing a pool of DNA fragments isolated from a population, and amplifying the target region.

As used herein, a population refers to the set of individuals (e.g., mammals, humans, Homo sapiens) from which DNA samples are taken. In certain embodiments, a population is made up of individuals having common characteristics, such as gender, race, ethnicity, age, disease or disorder and the like. For example, a population of humans can be a sample representative of all human inhabitants of Earth, or can include only individuals from the same demographic group, such as individuals of the same race and/or ethnicity (e.g., individuals of European ancestry, African ancestry, Asian ancestry, Indian ancestry, Hispanic ancestry). It is appreciated that a population can be made up of individuals which are a subgroup of a larger population. For example, the population of Han Chinese is included in the population of individuals of Asian ancestry.

Proband populations are made up of individuals having a particular disease or disorder. Early onset proband populations are made up of the youngest 5 or 10% of individuals which develop disease, and late onset proband populations of are made up of the oldest 5 or 10% of individuals which develop disease. As used herein, "young individuals" includes individuals which are considered to be juveniles, and "aged individuals" includes the oldest about 5% of individuals. For example, a young human population includes individuals of 18 years of age or less, preferable of about 6 years of age or less. An aged human population includes individuals of at least 90, preferably at least 98 years of age. All individuals that are not young or aged, as described herein, are considered to be of intermediate age. Age-specific intermediate populations are made up of individuals of a desired age, such as humans having ages which fall within a desired interval (e.g., a five or ten year interval).

The number of individuals included in the population can vary. Generally, the population is made up of at least 1000 individuals. The method of the invention is well suited for detecting point mutations which occur at a low frequency (e.g., about $5 \times 10^{-5}$) and thus permits the use of a large population. For example, the population can include at least about 1000 or at least about 10,000 individuals. In particular embodiments, the population can be made up of between about 10,000 and about 1,000,000 individuals. In a preferred embodiment, the population is made up of about 100,000 individuals.

The DNA (nuclear, mitochondrial, pooled) can be isolated from each individual in the population and fragmented using methods well known to those of skill in the art. Generally, a sample (e.g., any DNA-containing biological sample such as a tissue biopsy, whole blood, isolated cells) is acquired and DNA is isolated from the cells contained in the sample. DNA can be isolated form a sample from an individual or from pooled samples. For example, DNA can be obtained by acquiring a sample of white blood cells of other suitable tissue sample from each individual of the population. Samples containing similar numbers of cells can be pooled and DNA can be isolated therefrom. Several samples of DNA that were isolated from individuals can also be pooled. Many suitable methods for isolating DNA from cells and/or tissues are available. The isolated DNA is generally fragmented by digestion with one or more suitable restriction endonuclease. Any restriction endonuclease which does not cleave within the target region of the DNA can be used. Preferably, a restriction endonuclease which cuts DNA with low frequency is selected, such as an enzyme with a 6 base pair recognition site ("six-cutter"). Six-cutter enzymes are less likely to cut a target sequence than other enzymes which cut DNA with higher frequency (e.g., four-cutters) and convert genomic DNA into a pool of fragments averaging about 4000 bp. DNA can be individually digested, and the resulting fragments pooled, or a pooled sample of DNA can be digested with a suitable restriction endonuclease to produce a pool of fragments.

The pool of DNA fragments provides a suitable template for amplifying the target region of the genome. The target sequences can be amplified without further processing of the pool, or the pool can be processed to enrich for fragments which contain the target region. Preferably, the pool is enriched for fragments which contain the target region. Enrichment can be achieved using suitable methods. For example, as described herein, the DNA fragments can be incubated with a labeled oligonucleotide probe (e.g., biotin-labeled) that can hybridize to the target region or to sequences flanking the target region under conditions suitable for hybridization, and the labeled hybrids which form can be isolated (e.g., using streptavidin-coated beads). Enrichments of about 10,000 fold have been achieved using this method.

The target regions of the pool of DNA fragments are amplified in a high fidelity polymerase chain reaction (hifiPCR) under conditions suitable to produce double stranded DNA products which contain a terminal high temperature isomelting domain that is labeled with a detectable label. "HifiPCR" is a polymerase chain reaction performed under conditions where PCR-induced (e.g., polymerase induced) mutations are minimized (see, for example, U.S. Pat. No. 5,976,842, the entire teachings of which are incorporated herein by reference). As used herein, hifiPCR refers to a polymerase chain reaction wherein the mutant fraction of each PCR-induced mutation is not greater than about $10^{-4}$. Preferably, the mutant fraction of each PCR-induced mutation is not greater than about $5 \times 10^{-5}$. HifiPCR of target regions can be carried out using Pfu polymerase where the amplification is limited to about 6 doublings. As described herein, the frequency of PCR-induced mutation at any base is dependent upon the number of PCR doublings and the error rate per base pair per doubling. Thus, suitable conditions for hifiPCR can be determined for any desired polymerase and target sequence.

The high temperature isomelting domain is provided by a detectably labeled primer which includes a 5' 40 base non-monotonous sequence with a high melting temperature (e.g., a G/C rich sequence) and a 20 base target region specific sequence. Suitable detectable labels include, for example, a radioisotope, an affinity label (e.g., biotin, avidin), a spin label, a fluorescent group (e.g., fluorescein) or a chemiluminescent group. In a preferred embodiment, the primer is labeled at the 5' end with fluorescein.

The products of the hifiPCR, which contain wild-type or mutant (e.g., having a point mutation) target regions, can be separated based upon differences in melting temperature of the wild-type and mutant target regions. The products which contain mutant target regions can be recovered, thereby producing a secondary pool of DNA that is enriched in target regions that contain point mutations. The PCR products which contain wild-type or mutant target regions can be separated without further processing. However, it is preferred that the PCR products are processed to form a mixture of wild-type homoduplexes and heteroduplexes which contain point mutations before separation. Such a mixture can readily be prepared, for example, by heating the products of hifiPCR, thereby melting the products to form single-stranded DNAs. The mixture can then be cooled to allow the single-stranded DNAs to anneal. Because the quantity of DNA strands with a wild-type target region greatly exceed the quantity of DNA strands with a mutant target region, essentially all DNA strands with a mutant target region form heteroduplexes with wild-type strands.

A number of methods which are suitable for separating nucleic acids based upon differential melting temperatures have been described, including constant denaturing gel capillary electrophoresis (U.S. Pat. No. 5,633,129, the entire teaching of which are incorporated herein by reference), constant denaturing gel electrophoresis, denaturing gradient gel electrophoresis or denaturing high performance liquid chromatography (Gross E. et al., 1999. *Hum. Genet.* 105: 72–78). Preferably, the PCR products which contain wild-type or mutated target regions, or the mixture of wild-type homoduplexes and heteroduplexes which contain point mutations prepared therefrom, are separated by constant denaturing gel capillary electrophoresis and the DNAs containing mutated target regions are recovered to produce the secondary pool of DNA.

The secondary pool can be amplified in a hifiPCR under conditions where only homoduplexed DNA is produced, thereby producing a mixture of homoduplexed DNA containing wild-type target region and of homoduplexed DNAs which contain target regions that include point mutations. The homoduplexed DNAs, which contain target regions that include point mutations, can be resolved based upon the differential melting temperatures of the DNAs as described and the resolved DNAs can be recovered. Occasionally, a mutant homoduplex can have a melting temperature which is nearly identical to the melting temperature of the wild-type homoduplex. Such mutant homoduplexes can be detected by recovering the wild-type homoduplex fraction, and heating and cooling the fraction to create heteroduplexes. The resulting heteroduplexes can be resolved and recovered. Preferably, the homoduplexed or heteroduplexed DNAs which contain target regions that include point mutations are resolved by constant denaturing gel capillary electrophoresis and the resolved DNAs are recovered. The recovered DNAs can then be sequenced using any suitable sequencing method (e.g., cycle sequencing) to identify the point mutations. Once identified the frequency with which each inherited point mutation occurs in the population can be determined.

Inherited point mutations identified as described herein can be used to create a quantitative fine structure map of the point mutations in a gene. Such a quantitative map can be created by determining the frequency with which each identified point mutation occurs in the population. The method of the invention is particularly suited for this purpose because rare inherited point mutations can be detected in DNA pools isolated from large populations (e.g., 100,000 or even 1,000,000 individuals). It is well appreciated that the accuracy and utility of such a map is greatly enhanced if it reflects the frequency of mutations in a large population. A fine structure map of a genes can be used to determine if the gene carries harmful, deleterious or beneficial (e.g., longevity promoting) alleles.

In another aspect the invention relates to a method for identifying genes which carry a harmful allele. As described herein, harmful alleles are alleles which shorten life span. Harmful alleles include, for example, alleles which are causal for disease (e.g., cancer, atherosclerosis) or which accelerate the onset of a disease, such as point mutations which increase somatic mutation rates. Harmful alleles are expected to be present at a reduced frequency in a population of aged individuals in comparison to a population of young (juvenile) individuals. Thus, genes which carry harmful alleles can be identified by comparing the sum frequency or the individual frequencies of inherited point mutations found in the gene of an aged population to the sum frequency or the individual frequencies of the same inherited point mutations in a young population. The method comprises identifying the inherited point mutations which are found in the genes or portions thereof of a population of young individuals and in the genes or portions thereof of a population of aged individuals. The frequencies with which each point mutation occurs in each of the populations is determined. In one embodiment, the sum of the frequencies (sum frequency) of all inherited point mutations in a selected gene, or fragment thereof, of the young population is calculated. The sum frequency of all inherited point mutation in the selected gene or fragment thereof, of the aged population is also calculated, and the sums are compared. A significant reduction in the sum frequency of inherited point mutations in a gene of the aged population relative to the young population indicates that the selected gene carries a harmful allele. In another embodiment, the frequency of each point mutation identified in a selected gene or portion thereof of the young population is compared with the frequency of the same point mutation identified in the selected gene of the aged population. A significant reduction in the frequencies of two or more inherited point mutations in a gene of the aged population indicates with a high probability that the gene carries a harmful allele. A significant reduction in frequency of only one inherited point mutation in a gene of the aged population indicates that the gene either carries a harmful allele or is genetically linked to a nearby a harmful allele. Where no significant differences in the sum frequency or the individual frequencies of the inherited point mutations are observed, the gene does not carry harmful alleles.

As used herein, "significant" means statistically significant. Statistical significance can be determined using a suitable statistical test, such as Chi square test or multinomial distribution, modified to account for the fact that a large number of alleles are being compared. For example, the statistical test can be modified by application of the Bonferoni inequality.

Genes in which the frequency of one or more inherited point mutations decline in aged population in comparison to a young population can be further studied. For example, the age-specific decline of the one or more inherited point mutations can be determined. Age-specific decline can be assessed by determining the frequency of the one or more inherited point mutations in one or more age-specific intermediate populations. The frequencies of the one or more inherited point mutations in the age-specific intermediate population(s) together with the frequencies in the young and aged population demonstrate the age-specific decline of the one or more point mutations. The determined age-specific decline of the one or more point mutations is compared to the theoretical age-specific decline of harmful alleles which cause mortal diseases (each mortal disease has a theoretical rate of decline). The theoretical age-specific decline of harmful alleles which cause mortal disease, $X(h,t)$ (equation 4), is calculated as described herein (Example 1). If the determined age-specific rate of decline of the one or more point mutations is similar or essentially the same as (i.e., is not statistically different from) the theoretical age-specific decline of harmful alleles which cause a particular mortal disease, then the gene which carries the one or more inherited point mutations has a high probability of being causal for the particular disease.

A gene in which one or more point mutations undergo age-specific decline and which has a high probability of being causal for the particular disease can be further studied in a suitable proband population. Generally, the proband population consists of individuals of various ages who have the particular disease. The frequency of the one or more point mutations in the proband group is determined and compared with the frequency of the same one or more point mutations in the young population. A significant increase in the frequency of the one or more point mutations in the proband population in comparison to the young population indicates that the gene carries a harmful allele that plays a causal role in said disease.

There are genes that carry harmful alleles which do not cause disease, but which are secondary risk factors that accelerate the appearance of disease. Such genes can contain one or more inherited point mutations which undergo age-specific decline, and which hasten the appearance of the particular disease. However, a significant association with the proband population, which consists of individuals of a variety of ages, may not be observed for these mutations. In such a situation, the frequency of the one or more inherited point mutations can be determined in an early onset proband population and compared with the frequency of the same one or more inherited point mutations in the young population. A significant increase in the frequency of the one or more point mutations in the early onset proband population in comparison to the young population indicates that the gene carries a harmful allele that is a secondary risk factor which accelerates the appearance of the disease.

Genes carrying harmful alleles that are secondary risk factors which accelerate the appearance of disease can also be identified by determining the frequency of each inherited point mutation which occurs in the genes of a population with early onset of a particular disease (early onset proband) and which occur in the genes of a population with late onset of the same disease (late onset proband). The frequencies of each inherited mutation for a selected gene of the early onset proband are compared with the frequencies of the same point mutations in the gene of the late proband population. A significant increase in the frequency of one or more inherited point mutations in the early onset proband relative to the late onset proband indicates that the gene carries a harmful allele that is secondary risk factors which accelerate the appearance of the disease.

The invention also relates to a method for identifying genes which carry an allele which increases longevity. The method comprises identifying the inherited point mutations which are found in the genes or portions thereof of a population of young individuals and in the same gene or portion thereof in a population of aged individuals. The frequencies with which each point mutation occurs in a selected gene is determined for each population. In one embodiment, the sum of the mutation frequencies for the selected gene in the young population is compared to the sum of the mutation frequencies for the selected gene in the aged population. A significant increase in the sum of the mutation frequencies in the aged population relative to the young population indicates that the selected gene carries alleles which increase longevity. In another embodiment, the frequency of each point mutation identified in a selected gene in the young population is compared to the frequency of the same point mutation identified in the selected gene in the aged population. A significant increase in the frequency of two or more point mutations in a gene of the aged population relative to the young population indicates that the selected gene carries an allele which increases longevity. In another embodiment, the frequency of each point mutation identified in a selected gene in the young population is compared to the frequency of the same point mutation identified in the selected gene in the aged population. A significant increase in the frequency of a point mutation in the gene of aged population relative to the young population indicates that selected gene carries an allele which increases longevity or which is linked to a gene that increases longevity.

The invention also relates to a method for identifying genes which affect the incidence of a disease. The method comprises identifying the inherited point mutations which are found in genes or portions thereof of a population of young individuals not afflicted with the disease, and in the genes or portions thereof of a proband population having the disease. The frequencies with which each point mutation occurs in a selected gene or segment thereof is determined and summed for each population. The sum frequency of point mutation in a selected gene or portion thereof in the young population is compared to the sum frequency of point mutations in the selected gene or portion thereof in the proband population. A significant increase in the sum frequency of point mutations in the proband population relative to the young population indicates that the gene plays a causal role in said disease.

In another aspect the invention relates to a method for identifying a gene which carries a deleterious allele. Deleterious alleles are alleles which interfere with reproduction. The genes are identified based upon the frequency of obligatory knock-out and presumptive knock-out alleles in a population. Obligatory knock-outs are point mutations which necessarily inactive the gene, such as point mutations which introduce stop codons or frame shifts in exons of protein encoding genes. Obligatory knock-outs can also occur in splice sites in the exons or introns of protein encoding genes. Presumptive knock-outs are point mutations which are expected to inactive the gene. For example, a point mutation that introduces a cysteine residue into a protein can form an inappropriate disulfide bond and alter the folding or cause aggregation of the protein. Accordingly, inherited point mutations which introduce a cysteine residue into a protein are considered presumptive knock-outs.

In one embodiment, the method for identifying a gene which carries a deleterious allele comprises identifying the inherited point mutations occurring in the exon(s) and splice sites of a gene of a population of young individuals. The inherited point mutations that are obligatory knock-outs are identified by inspection of the sequences, and the frequencies with which each obligatory knock-out point mutation occurs is determined. The frequencies of all obligatory knock-out point mutations identified in the gene are summed. A sum frequency of all obligatory knock-out point mutations of less than about 2% indicates that said gene carries a deleterious allele. In another embodiment, a sum frequency of all obligatory knockout point mutations of about 0.02% to about 2% indicates that said gene carries a recessive deleterious allele. In anther embodiment, a sum frequency of all obligatory knock-out point mutations of less than about 0.02% indicates that said gene carries a dominant deleterious allele.

In another embodiment, the method for identifying a gene which carries a deleterious allele comprises identifying the inherited point mutations occurring in the exon(s) and splice sites of a gene of a population of young individuals. The inherited point mutations that are obligatory knock-outs and the inherited point mutations that are presumptive knock-outs are identified by inspection of the sequences, and the frequencies with which each obligatory or presumptive knock-out point mutation occurs is determined. The frequencies of all knock-out point mutations identified in the gene (obligatory and presumptive) are summed. A sum frequency of all knock-out point mutations of less than about 2% indicates that said gene carries a deleterious allele. In another embodiment, a sum frequency of all obligatory knock-out point mutations of about 0.02% to about 2% indicates that said gene carries a recessive deleterious allele. In another embodiment, a sum frequency of all obligatory knock-out point mutations of less than about 0.02% indicates that said gene carries a dominant deleterious allele.

In another aspect, the invention relates to isolated nucleic acids which are complimentary to a strand of a gene or portion thereof, or an allele or portion thereof identified according to the methods described herein. The invention also relates to isolated target regions of a genome which contain inherited point mutations which are isolated according to the methods described herein.

Nucleic acids referred to herein as "isolated" are nucleic acids separated away from the nucleic acids of the genomic DNA or cellular RNA of their source of origin (e.g., as it exists in cells or in a mixture of nucleic acids such as a library), and may have undergone further processing. "Isolated" nucleic acids include nucleic acids obtained by methods described herein, similar methods or other suitable methods, including essentially pure nucleic acids, nucleic acids produced by chemical synthesis (oligonucleotides), by combinations of biological and chemical methods, and recombinant nucleic acids which are isolated.

Additionally, the nucleic acid molecules of the invention can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996. *Bioorganic &Medicinal Chemistry.* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNA has been shown to allow for specific hybridization to DNA and RNA under conditions of low ionic strength. The synthesis of PNA oligomers can be performed using standard solid phase peptide synthesis protocols as described in Hyrup et al. (supra; Perry-O'Keefe et al., 1996. *Proc. Natl. Acad. Sci. USA.* 93:14670). PNAs can be further modified, e.g., to enhance their stability, specificity or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup, supra; Finn et al., 1996. *Nucl. Acids Res.* 24:3357–63; Mag et al., 1989. *Nucl. Acids Res.* 17:5973; and Petersen et al., 1975. *Bioorganic Med. Chem. Lett.* 5:1119. Other DNA mimics can comprise an array of bases which are immobilized on a solid support, such as glass or silicon. The bases are arranged in a manner which permits hybridization with a complimentary nucleic acid.

The nucleic acid molecules and fragments of the invention can also include other appended groups such as peptides (e.g., for targeting host cell receptors in vivo), or agents facilitating transport across the cell membrane (see, e.g., Letsinger et al., 1989) *Proc. Natl. Acad. Sci. USA.* 86:6553–6556; Lemaitre et al., 1987. *Proc. Natl. Acad. Sci. USA.* 84:648–652; PCT Publication No. WO88/0918) or the blood brain barrier (see, e.g., PCT Publication No. WO89/10134). In addition, oligonucleotides can be modified with hybridization-triggered cleavage agents (see, e.g., Krol et al., 1988. *BioTechniques.* 6:958–976) or intercalating agents (see, e.g., Zon, 1988. *Pharm Res.* 5:539–549). The nucleic acids of the invention can also be modified by a detectable label, such as a radioisotope, spin label, antigen or enzyme label, fluorescent or chemiluminescent group and the like.

The nucleic acids of the invention can be used as probes, for example, to detect the presence of a deleterious allele. Probes can be of a suitable length to ensure specificity in a hybridization reaction. For example, the probes can be about 15 to several thousand nucleotides long. Preferred probes are synthetic molecules (e.g., oligonucleotides) which are about 15 to about 20 or 25 nucleotides long.

The invention also relates to an array of isolated nucleic acids of the invention, immobilized on a solid support, said array having at least about 100 different isolated nucleic acids which occupy separate known sites in said array, wherein each of said different isolated nucleic acids can specifically hybridize to a target region, gene or allele which contains an inherited point mutation. Such arrays can be prepared using suitable methods, such as the method described in U.S. Pat. No. 5,837,832, the entire teaching of which are incorporated herein by reference.

The arrays or DNA chips can be used as probes to detect harmful or deleterious alleles. For example, alleles which play a causal role in mortal disease (e.g., cancer) can be detected in individuals asymptomatic of the disease. An individual diagnosed in this manner could then begin appropriate prophylactic therapy. The arrays can be used to tailor chemotherapeutic intervention for an individual. For example, an array of probes which hybridize to alleles of xenometabolic enzymes (e.g., cytochrome P450s) can be used to determine an individuals ability to metabolize certain types of drugs. Accordingly, a drug which provides superior efficacy and minimal side effects can be selected for therapy. The arrays can also be used to provide genetic counseling. For example, an array of probes which hybridize to recessive deleterious alleles can be used to detect such alleles in a man and in a woman hoping to have a child. If both the man and the woman carry a recessive deleterious allele of the same gene, then 0.25 of the fertilized eggs produced by them would be homozygous for the allele and may not be viable. The same array can be used to select fertilized eggs which are not homozygous for a deleterious allele. For example, eggs fertilized in vitro can be allowed to undergo cleavage, and a single cell can be removed from the egg for genetic analysis. Eggs which are not homozygous for a deleterious allele can be selected and implanted into a woman's uterus.

The methods described herein can be used to identify any and all deleterious, harmful and beneficial point mutations carried by a particular population. Furthermore, a DNA chip or small set of DNA chips for detecting all deleterious, harmful and beneficial point mutations in all human populations and subgroups found in North America, Europe, Asia, Africa, South America can be prepared as a result of the invention.

EXEMPLIFICATION

Example 1

Introduction

Many inherited mutations are known to cause or predispose people to disease. As the human genome is mapped and sequenced, the number of markers that allow for genome-wide scans has increased dramatically allowing many regions linked to disease to be determined or mapped by exclusion (Nelen, M. et al., 1996. *Nat. Genet.* 13:114–116; Comuzzie et al., 1997. *Nat. Genet.* 15:273–276; Marshall, E. 1997. *Science.* 277:1752–1753). To date, some 1339 genes associated with human disease have been chromosomally mapped (Genome Database, Johns Hopkins University). However, when any long sequences are compared between two randomly chosen alleles in the human population, approximately two variations are found for every 1000 bp (Rowen, L. et al., 1997. *Science.* 278:605–607). Thus in a large human population any 1000 bp would be expected to display many sequences differing from the canonical sequence. Some of these sequence variants may affect physiological functions such as tumor suppression, xenometabolism, DNA repair, or control of cell death and division.

It seems logical that if a subpopulation, by virtue of an inherited mutation, were at risk of a form of death for which the rest of the population were not at risk, then the age-dependent death rate for that subpopulation would be increased relative to the mean. Any incremental increase in the age-dependent death rate creates the expectation that the fraction of the human population at risk must decline with increasing age. Herein we consider a hypothetical tumor suppressor gene in which inherited gene-inactivating mutations would define the population at risk for a lethal disease such as pancreatic cancer. How we calculate our age-dependent expectations requires some explanation.

To make our estimates we have employed Knudson's (Knudson, A., 1971. *Proc. Natl. Acad. Sci. USA.* 68:820–823) multistage model for carcinogenesis as extended by Herrero-Jimenez et al. (1998. *Mut. Res.* 400: 553–578). In this model, two mutations occurring at rates $r_i$ and $r_j$ in somatic cells are necessary to inactivate both copies of a first 'gatekeeper' tumor suppressor gene, 'GK', resulting in an 'initiated' cell that will grow as an adenoma. An inactivating mutation inherited in a first gatekeeper gene 'GK' would almost certainly lead to the disease early in life. An example of such a condition is familial adenomatous polyposis (FAP) in which members of the same family develop colon cancer early in life because of inherited mutations inactivating one allele of the adenomatous polyposis coli (APC) gene (Kinzler, K. and Vogelstein, B., 1996. *Cell.* 87:159–170).

We have hypothesized that as the cells continue to grow and die in a growing adenoma, the eventual stochastic loss of inherited heterozygosity in a second gatekeeper tumor suppressor gene 'A' occurs at rate $r_A$. This third somatic genetic event gives rise to a triple mutant which by rapid growth and further genetic changes creates a lethal carcinoma (see FIG. 1). An inactivating mutation inherited in one allele of gene A, the second gatekeeper, would not lead to disease until the two alleles of the first gatekeeper are lost and the adenoma has grown to a size making loss of heterozygosity for gene A in any one adenoma cell likely. A person inheriting such a mutation in A might or might not acquire the three rate-limiting events before dying of some other cause. Therefore a subpopulation inheriting a mutation in either allele of gene A would be at risk of a late onset cancer. In the example below, heterozygotes in the second gatekeeper allele constitute the subpopulations at risk for 'sporadic' cancers (FIG. 1; Herrero-Jimenez, P. et al., 1998. *Mut. Res.* 400:553–578).

The identification of genes in which polymorphisms (usually defined as alleles present at an arbitrarily chosen level, typically 1% or more, of the population) represent a genetic risk for disease has become a very important area in human genomics (Agundez et al. 1997. *Age Ageing*. 26:147–151; 1997; Daly et al., 1997. *Environ. Health. Perspect.* 102: 55–61; Kaiser, J., 1997. *Science.* 278:569–570). Candidate genes in which inactivating mutations could place one at an increased risk of cancer risk include tumor suppressor genes, xenometabolizing genes, DNA repair and replication genes and genes affecting the cellular kinetics of division and death in normal and adenomatous tissue. An inactivating mutation in either the first or second gatekeeper genes would create a primary risk factor for familial and sporadic cancers respectively. Mutations affecting secondary factors, such as mutation rates or cell kinetics, would increase age-dependent risk but only in persons inheriting a mutation in the first gatekeeper, GK, or the second gatekeeper, A, genes. Germinal mutations that define sporadic late onset mortality may be highly prevalent in a general population as they do not have a lethal effect until rate limiting events take place, allowing inheritance of the mutant alleles. An example of an allele that appears to be related to late onset mortality via coronary heart disease is the e4 allele of the apolipoprotein E gene which has been reported to decline in extremely aged populations (Kervinen, K. et al., 1994. *Atherosclerosis.* 105:89–95; Schachter, F. et al., 1994. *Nat. Genet.* 6:29–32).

Determination of which point mutations prevalent in the general population are associated with late onset mortality requires study of large populations in order to achieve desirable statistical precision. Such determinations require a technology that can detect differences as small as a single nucleotide change in large populations at reasonable cost. Techniques that are currently used to identify point mutations are: single-strand conformation polymorphism (SSCP) analysis (Orita, M. et al., 1989. *Proc. Natl. Acad. Sci. USA.* 86:2766–2770), restriction fragment length polymorphism (RFLP) analysis (Arnheim et al., 1985. *Proc. Natl. Acad. Sci. USA.* 82:6970–6974), micro- and mini-satellite variation (Koreth, J. et al., 1996. *J. Pathol.* 178:239–248), allele-specific hybridization-dependent techniques (Shuber, A. et al., 1997. *Human Mol. Genet.* 6:337–347), denaturing gradient gel electrophoresis (DGGE; Guldberg, P. et al., 1993. *Genomics.* 17:141–146), DNA chips (Chee et al., 1996. *Science.* 274:610–614), and direct sequencing.

Unfortunately, the utility of these techniques is limited by the costs and labor required to assay each individual in large populations. In some techniques such as SSCP or DNA chips, but not DGGE, a significant fraction of possible point mutations in a defined sequence would not be detected. In the case of direct sequencing which would detect any point mutation in a given sequence, cDNAs, not genomic sequences, are generally proposed for analyses. This strategy misses point mutations blocking normal mRNA splicing, an important point since a significant percentage (20–30%, varying among genes) of point mutations inactivating a gene appear to be within splice sites of the introns (Kat, A., 1992. Ph.D. thesis, M. I. T.).

We propose a different approach based on technology developed to observe somatically-derived point mutational spectra in human tissues. This technology has already been demonstrated to detect mutations in 100 bp sequences with a sensitivity of at least $10^{-6}$ (Khrapko, K. et al., 1997. *Nucl. Acids Res.* 25:685–693). We first separate mutant from non-mutant sequences using differential cooperative melting behavior of double-stranded DNAs (Poland, 1978; Fischer, S. and Lerman, L., 1983. *Proc. Natl. Acad. Sci. USA.* 80:1579–1583). By coupling constant denaturant capillary electrophoresis (CDCE) with high-fidelity DNA amplification (hifiPCR) (Khrapko, K. et al., 1994. *Nucl. Acids Res.* 22:364–369; Khrapko, K. et al., 1997. *Nucl. Acids Res.* 25:685–693), we could easily measure any SNP in populations of up to $10^4$ people in a single experiment within a defined target sequence. Through comparisons of randomized blood samples from the general U.S. population of newborns with those drawn from the general U.S. population of centenarians, point mutations associated with mortal disease should be identified as they are expected to markedly decrease in aged populations. When proband populations afflicted with specific diseases are available for study, these identical polymorphisms are expected to be markedly increased relative to the newborn population (Because we can easily measure point mutations well below 1% we designate these as point mutations, rather than cavil with established usage that 'polymorphism' implies a frequency of greater or equal to 1%.).

The analytical approach combining CDCE and hifiPCR has the ability to identify mutations that are associated with mortal disease with a sensitivity and statistical strength which should make it significantly more desirable than proposed massive resequencing strategies. Examining general populations (e.g., well-mixed populations) should diminish biases such as founder effects which are encountered in traditional family linkage studies. In the next section we calculate the expected differences between newborn, proband and centenarian populations for the hypothetical example of a gene in which inactivating mutations are a primary risk factor for pancreatic cancer.

Analytical Methods

Fractions at Risk of Mortal Disease: Pancreatic Cancer Example

In order to plan a search for disease-related point mutations it is very useful to have an estimate of the total fraction at risk in the general population. To aid us with such estimates, we have collected the data for mortal diseases recorded in the Vital Statistics of the United States (Census, 1900–1936; DHHS, U.S.: National Center for Health Statistics. In: Services, U.S.D.o.H.a.H. (Ed.), Vital Statistics of the United States. US Government Printing Office, Hyattsville, 1937–1992). Combined with census population data for the reporting states and counties we have been able to calculate a birthyear cohort- and age-specific function, OBS (h,t), which is the number of deaths from the observed cause at age t divided by the number of persons alive at age t in a cohort born in year h.

For each birthyear h, we posit that there exists a fraction of the population, $F_h$, at lifetime risk of the observed cause of death. Since our group is especially interested in discovering gene/environment interactions defining risk, $F_h$ is modeled as the product of the fraction of genetically-susceptible persons multiplied by the fraction of environmentally-exposed persons:

$$F_h = F_{h,genetic} \times F_{h,environmental} \qquad \text{Equation 1}$$

If everyone were exposed to the same environmental factor(s), then $$F_{h,environmental}=1 \text{ and } F_h = F_{h,genetic}.$$

However, if only a part of the population were exposed, then $F_{h,genetic}$ would be expected to be greater than $F_h$. Therefore, $F_h$ is a useful estimate of the lowest possible fraction of $F_{h,genetic}$. We have been experimenting with an algebraic approach to calculate $F_h$ and other parameters in the general multistage model of FIG. 1. In our formulation, P(t) is the probability of dying of the observed cause at age t, given that one is both at risk and is still alive at age t. Deaths that are not caused by the risk factors for the observed form of death are accounted but 'cancel out' in our derivation (Herrero-Jimenez, P. et al., 1998. *Mut. Res.* 400: 553–578). Deaths caused by the identical risk factors for the observed form of death are accounted by representing the fraction of the sum of the deaths due to these factors from the observed form of death as f. We have found that birthyear cohort- and age-specific function OBS(h,t) may be reasonably approximated as:

$$OBS(h, t) = \frac{F_h \cdot P(t)}{F_h \div (1 - F_h) \cdot e^{\frac{1}{f}\int P(t)dt}} \qquad \text{Equation 2}$$

when the survival rates for the observed cancer is small.

P(t), the age-dependent probability of the observed form of death within the group at risk, we have found to be usefully represented through algebra first suggested by (Moolgavkar, S. et al., 1988. *Risk. Anal.* 8:383–392), somewhat extended by (Herrero-Jimenez, P. et al., 1998. *Mutat. Res.* 400:553–578) and further corrected (Herrero-Jimenez, P. et al., 1999).

$$P(t) = 2\tau^2 r_i r_j \sum_{a=0}^{t} N_a a\left(\frac{\alpha-\beta}{\alpha}\right) \frac{d\left(1 - e^{-r_A \cdot \left(\frac{\alpha}{\alpha-\beta}\right)^2 \cdot 2^{(\alpha-\beta)(t-a)}}\right)}{d(t-a)} \qquad \text{Equation 3}$$

where in addition to the terms defined in FIG. 1 we use a to represent age at the time of initiation, t to represent age at death from the observed cause and Na to represent the number of cells in a tissue at risk.

We use X(h,t) to represent the fraction of the surviving general population still at risk of death from pancreatic cancer as the population ages:

$$X(h, t) = \frac{F_h}{F_h \div (1 - F_h) \cdot e^{\frac{1}{f}\int P(t)dt}} \qquad \text{Equation 4}$$

Any inherited mutation that creates the risk fraction $F_h$ should be selected against as each birthyear cohort ages. This means that at t=0, X(h,t)=$F_h$, and that, as the population at risk dies somewhat faster than the general population X(h,t) will decrease with increasing age, t.

Figure 2A:
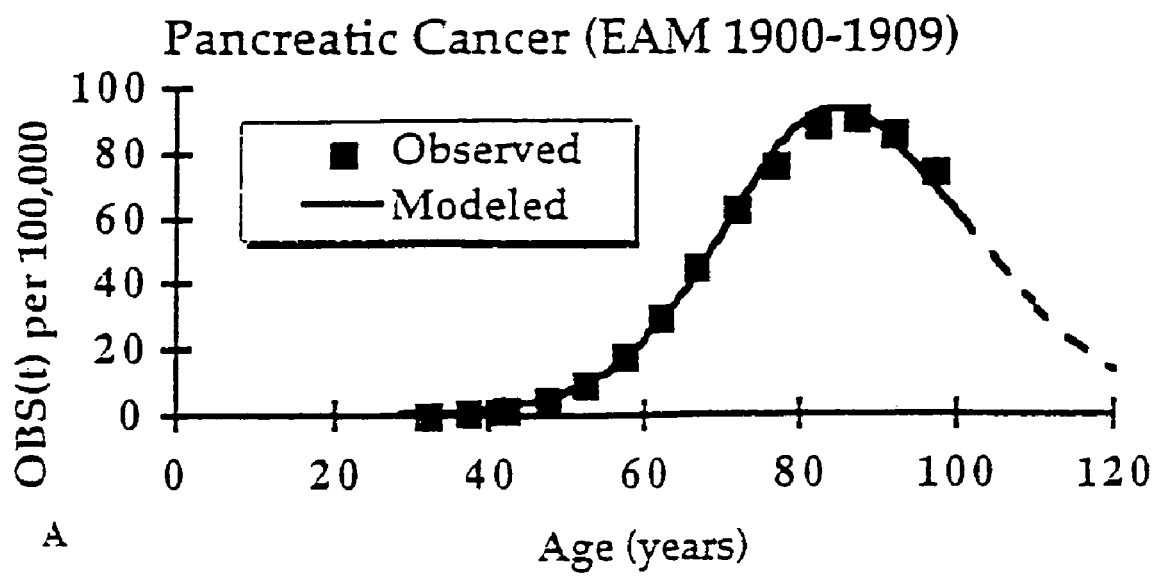
FIG. 2A is a graph that demonstrates the age-dependent pancreatic cancer mortality, OBS(h,t), for European-American males born in the 1900–1909. Solid squares are actual data. The smooth line is the model suggested by Herrero-Jimenez et al (1998. *Mut. Res.* 400:553–578).

OBS(h,t) and X(h,t) for European-American males born between 1900 and 1909 who died of pancreatic cancer are shown in FIG. 2A. The mortality rate is low until it rises monotonically from the early 40s, reaches a maximum at 85, and decreases to a much lower value for centenarians. The fraction at risk for the cohort, $F_h$, is calculated to be 22%, which defines X(h,t) for the cohort at birth when t=0. X(h,t) remains at approximately 22% until age 60 then decreases to a value of about 4.4% at age 100 (see FIG. 2B). In short, while 22% of the population had a risk of pancreatic cancer at age 0, only some 4.4% of surviving centenarians would still be at risk. Note that only 3.3% of the population born in 1900–09 actually died of pancreatic cancer. One of the strengths of using OBS(h,t) to calculate F(h) is that it does not depend on the actual fraction of a birth cohort dying of the observed disease. F(h) defines the fraction of a birthyear cohort which would die from pancreatic cancer in an imaginary world in which pancreatic cancer were the only form of death, i.e., F(h) is the fraction of the cohort population that could potentially die from pancreatic cancer.

2.2. Distribution of Inactivating and Silent Mutations in Genes

In the example of pancreatic cancer, $F_h$, derived from the data of FIG. 2A and Equation 2 is about 0.22. This suggests that at least 22% of the population carries a pancreatic cancer disease-related gene (monogenic hypothesis). These allelic variants could consist of frameshifts, stop codons, splice site changes, inactivating missense mutations, large additions or deletions. Point mutations would be represented in all these classes of mutation except for large additions and deletions. In addition to expressed mutations one would expect to see a set of silent (cryptic) mutations, mostly missense or "wobble" in nature when they fall in the exons but of all kinds when they fall in introns.

The numerical distribution of allelic variants would be expected to contain a few point mutations (e.g., polymorphisms) present at high frequencies in the population, among many other point mutations present at lower frequencies. This quantitative distribution of mutations over a DNA sequence must also be considered when planning point mutation studies in populations.

To acquaint ourselves with such a distribution of known rare point mutations inactivating a typical human gene, we examined the set of all such known mutations inactivating the Hprt gene (in exons and neighboring splice sites) in human cells. Mutations in this gene and DNA-mediated tranformations were studied in the early 1960s by Szybalska and Szybalski (1962). About a dozen hotspots were found to account for about 50% of all Hprt mutations (Kat, A. et al., 1993. *Proc. Natl. Acad. Sci. USA.* 90:6424–6428). The fraction of individual mutations range from about 0.1% to greater than 10% of the total observed mutations, each of which inactivated the Hprt gene. Applying this example to the point mutations creating risk of pancreatic cancer, we would expect that at least 22% of the population would carry such an inactivating mutation in one allele of the gene. But we would expect to find the mutant as a hotspot in only 11% of the population if we inspected the sequences of exons and splice sites. Expecting these to be found in ten different point mutations, an average point mutation would be expected in about 1.1% of the newborn population. Accompanying these hotspots, which inactivate the gene, would be multiple mutations that have no effect on gene expression (silent or cryptic mutations).

Silent inherited point mutations in the general population have been observed in the APC gene by many laboratories (Fodde, R. et al., 1992. *Genomics*. 13:1162–1168; Nagase, H. et al., 1992. *Hum. Mutat.* 1:467–73; Powell, S. et al., 1992. *Nature*. 359:235–237; Dobbie et al., 1994. *Eur. J. Cancer.* 30A:1709–1713; Groden, J. et al., 1991. *Cell.* 66:589–600). We have collected these reports and, in summary, find that there are 15 silent polymorphic mutations distributed throughout the APC gene cDNA. The frequencies of each SNP range from 1 to 40% of all alleles sequenced.

With our suggested technological approach, using 10,000 mixed blood samples, any rare point mutation with a frequency as low as 0.05% could be observed with reasonable precision. Such a result would arise from 10 individuals each carrying one mutant allele and the 95% confidence limits on such an expectation are 5–18. In a gene for which mutations may lead to increased risk of death after age 50, i.e., cancer, diabetes, or atherosclerosis, individual silent point mutations are expected to be approximately at equal fractions with inactivating polymorphisms in newborns. These fractions of silent, point mutations would not be expected to change in probands or centenarian populations.

2.3. Single Genetic Risk Factors: Monogenic Diseases

Some disease risks are defined by inheritance of an inactivating mutation of either allele of one and only one gene. We refer to these as monogenic risks and in our formulation, $F_h = F_{genetic} \times F_{environmental}$. An example was illustrated in FIG. 1 in which gene 'A' heterozygotes represents the subpopulation at risk for a sporadic cancer type. All gene inactivating point mutations in gene 'A' at birth would contribute to the estimate of $F_h$, the fraction at risk among newborns. Using the initial value afforded by the estimate of $F_h$, and the values of X(h,t) from FIG. 2B, we have calculated the expected number of rare point mutations as a function of age in randomly selected populations of 10,000 persons.

Newborn Population Born in 1998 $X(h,t)=X(1998, 0)=F_h=0.22$
10,000 individuals sampled
2200 individuals would be expected to carry a disease-related allele
1100 individuals would be expected to carry a detectable disease-related polymorphism in the exons and splice sites of the gene
110 individuals would have a particular detectable inactivating polymorphism at an average allele frequency of $5.5 \times 10^{-3}$
110 individuals would have a particular silent polymorphism at an average allele frequency of $5.5 \times 10^{-3}$ Proband Population X=1
10,000 individuals sampled; all would be expected to carry a disease-related allele
5000 individuals would be expected to carry a detectable disease-related polymorphism in the exons and splice sites of the gene
500 individuals would have a particular detectable inactivating polymorphism at an average allele frequency of $2.5 \times 10^{-2}$
110 individuals would have a particular silent polymorphism at an average allele frequency of $5.5 \times 10^{-3}$ Centenarian Population $X(h,t)=X(1895, 100+)=0.044$
10,000 individuals sampled
440 individuals would be expected to carry a disease-related allele
220 individuals would be expected to carry a detectable disease-related polymorphism in the exons and splice sites of the gene
22 individuals would have a particular detectable inactivating polymorphism at an average allele frequency of $1.1 \times 10^{-3}$
110 individuals would have a particular silent polymorphism at an average allele frequency of $5.5 \times 10^{-3}$ 2.4. Multiple Independent Genetic Risk Factors: Multigenic Disease A single disease may also arise as a result of inherited mutations at any one of several independent loci. Two examples of disease that may have similar clinical presentations but are actually comprised of a mutation in any one of several genes are autosomal dominant polycystic kidney disease (ADPKD) (Mochizuki, T. et al., 1996. *Science*. 272:1339–1342) and maturity-onset diabetes of the young (MODY) (Velho and Froguel, 1997).

Were inactivating mutations in any one of a set of five genes, independently capable of creating a risk for pancreatic cancer, then on average, the frequency of these mutant hotspots would be expected to be decreased by a factor of five relative to the monogenic case considered above. We represent this case for multigenic risk by, $F_h = F_{h,A} \cup F_{h,B} \cup F_{h,C}$ . . . where $F_{h,A} = F_{genetic\,'A'} \times F_{environmental\,'1'}, F_{h,B} = F_{genetic\,'B'} \times F_{environmental\,'2'}$, etc. Inspection of the case of pancreatic cancer risk defined in this way illustrates that now mutant fraction detection as low as 0.1% is essential for a sample size on the order of 10,000. X(A) denotes the surviving fraction at risk for a disease contributed by gene 'A', one specific gene of the possible 5 genes, 'A', 'B', 'C', 'D', 'E', in which an inherited inactivating allele create a risk for pancreatic cancer. One may, as in the example of monogenic inheritance above, calculate expected values for the newborn, proband and centenarian populations. While we omit the arithmetic exercise here the results are included in Table 1.

2.5. Multiple Interacting Risk Factors: Polygenic Disease

A disease may be caused by the combination of inherited mutations in two or more genes. Such diseases appear to include schizophrenia (Portin, P. and Alanen, A., 1997. *Acta. Psychiatr. Scand.* 95:73–80), and non-insulin dependent diabetes mellitus (Galli, J. et al., 1996. *Nat. Genet.* 12:31–37; Velho and Froguel, 1997). We use the case of 2 separate genes and the data for pancreatic cancer as an illustration. In our formulation, we represent the polygenic case by $F_h = F_{h,A} \cap F_{h,B}$. The geometrical mean of the mutant fractions, from genes 'A' and 'B', jointly creating a risk represented by F=0.22 is just $(0.22)1/2$ or 0.47. Therefore, in our example, 47% would be expected to carry inactivating polymorphisms in one of genes 'A' or 'B'. The expectations for newborns, proband and centenarians can be worked out as above for a monogenic risk factor. Again we omit the arithmetic and provide the results in Table 1.

2.6. Expected Values

In order to plan a study of point mutations in the general population one requires estimates of both the expected values and their dispersion for various possible biological situations such as those considered above. We provide in Table 1 our estimates of the number of individuals along with their 95% confidence limits (±2 standard deviations) in a populations of 10,000 for the situations of monogenic, multigenic and polygenic risk factors for pancreatic cancer. Table 1 also indicates the associated allele frequency for each of the cases. These statistical limits are calculated for one point mutation coprising some 10% of the set of expressed (important) mutations. The use of several point mutations in each gene or the sum of all point mutations showing age-dependent changes greatly increases the resolving power of the studies, as taught herein. We use examples of five and two risk factor genes involved in multigenic disease and polygenic disease models, respectively.

Table 1. Expected number of individuals and the related allele frequency (AF) for inactivating and silent polymorphisms in the calculated situations of monogenic, multiple independent (multigenic disease) and multiple interacting (polygenic disease) risk factors in pancreatic cancer.

|  | Monogenic inactivating | Monogenic silent | Multigenic inactivating | Multigenic silent | Polygenic inactivating | Polygenic silent |
|---|---|---|---|---|---|---|
| Newborn individuals | 110 ± 21 | 110 ± 21 | 22 ± 9 | 22 ± 9 | 235 ± 31 | 235 ± 31 |
| Proband individuals | 500 ± 45 | 110 ± 21 | 100 ± 20 | 22 ± 9 | 500 ± 45 | 235 ± 31 |
| Centenarian individuals | 22 ± 9 | 110 ± 21 | 4 ± 4 | 22 ± 9 | 175 ± 26 | 235 ± 31 |
| Newborn AF | $5.5 \times 10^{-3}$ | $5.5 \times 10^{-3}$ | $1.1 \times 10^{-3}$ | $1.1 \times 10^{-3}$ | $1.2 \times 10^{-2}$ | $1.2 \times 10^{-2}$ |
| Proband AF | $2.5 \times 10^{-2}$ | $5.5 \times 10^{-3}$ | $5 \times 10^{-3}$ | $1.1 \times 10^{-3}$ | $2.5 \times 10^{-2}$ | $1.2 \times 10^{-2}$ |
| Centenarian AF | $1.1 \times 10^{-3}$ | $5.5 \times 10^{-3}$ | $2 \times 10^{-4}$ | $1.1 \times 10^{-3}$ | $8.8 \times 10^{-3}$ | $1.2 \times 10^{-2}$ |

2.7. Effect of Population Sample Size

There are a number of plans afloat to collect blood samples and study point mutation numbers in the general population. Some have suggested that as few as a few hundred donors would be a sufficient sample to define important polymorphisms. Many have suggested 1000 as a compromise between the recognition that 'larger samples are, better' and the practical limits imposed by the costs of 'sequential sequencing' even in the biggest labs working on sequencing the human genome. In order to apply the thinking of this paper in this discussion about appropriate sample size, we here consider the expected variations in experiments involving 1000 vs. 10,000 blood donors drawn randomly from a much larger population.

FIGS. 3A–3F shows the expected number ±2SD given population sizes of 1000 and 10,000 for the hypothetical situations of monogenic, multigenic (n=5) and polygenic (n=2) risks in pancreatic cancer analyzed for populations of 10,000 in the preceding section. It is clear by inspection that a sample of 1000 would permit discrimination among newborn, proband and centenarian populations for a polymorphism occurring at the expected frequency at the 95% confidence level for the case of simple monogenic inheritance but not for multigenic or polygenic risk factors.

These confidence limits apply to the case of one and only one SNP compared among the three groups. In a scan of 500–1000 bp of human DNA some 5–10 separate, inactivating point mutations would be expected, greatly increasing the ability to recognize the involvement of the gene in a mortal disease.

A further consideration relates to the population size needed to study harmful mutations which are also recessive deleterious mutations. In such cases, for each gene carrying recessive deleterious mutations, the sum of their frequencies would be about 2%. About 1% would be observed in scanning exons and splice sites of a protein encoding gene, and the frequencies of individual point mutations would be about 0.1% or less. In such cases, studies in populations of 100,000 or more individuals would be required to observe statistically significant age dependent decline of harmful alleles which are also recessive deleterious alleles.

2.8. Can One Get 10,000 Centenarian Samples?

Figure 4:
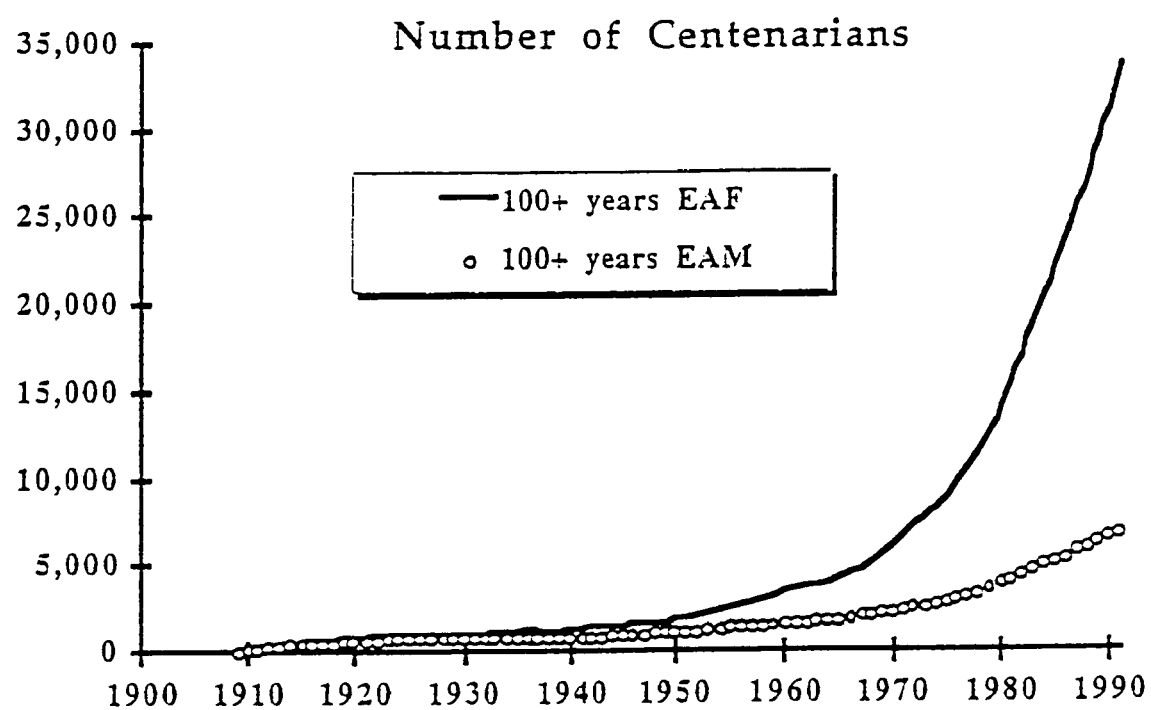
FIG. 4 is a graph that demonstrates that increasing numbers of European-American females (EAF) and European-American males (EAM) reach 100+years of age in the US, by year (Census, 1900–1936; DHHS, U.S.: National Center for Health Statistics. In: Services, U.S.D.o.H.a.H. (Ed.), Vital Statistics of the United States. US Government Printing Office, Hyattsville, 1937–1992).

The historical profile of survival for persons of extreme old age is plotted in FIG. 4 for the U.S. population of European Americans Females (EAF) and Males (EAM) from 1910–1991 (for 1910–1933 only 20–48 US states that submitted data to the death registry are included; Census, 1900–1936; DHHS, U.S.: National Center for Health Statistics. In: Services, U.S.D.o.H.a.H. (Ed.), Vital Statistics of the United States. US Government Printing Office, Hyattsville, 1937–1992). Both the male and female '100+' groups are increasing rapidly and indicate that there are more than 40,000 centenarians alive today in the U.S.

Figure 2B:
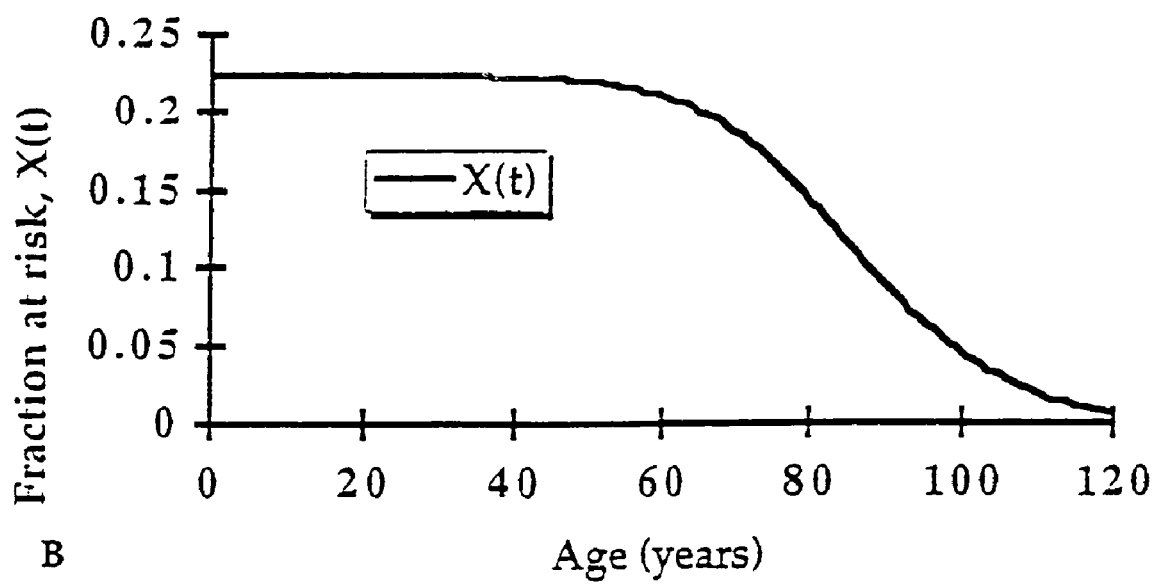
FIG. 2B is a graph that demonstrates the expected age-dependent surviving fraction at risk, X(h,t), for pancreatic cancer in this general population.
Figures 3A, 3B, 3C, 3D, 3E, 3F:
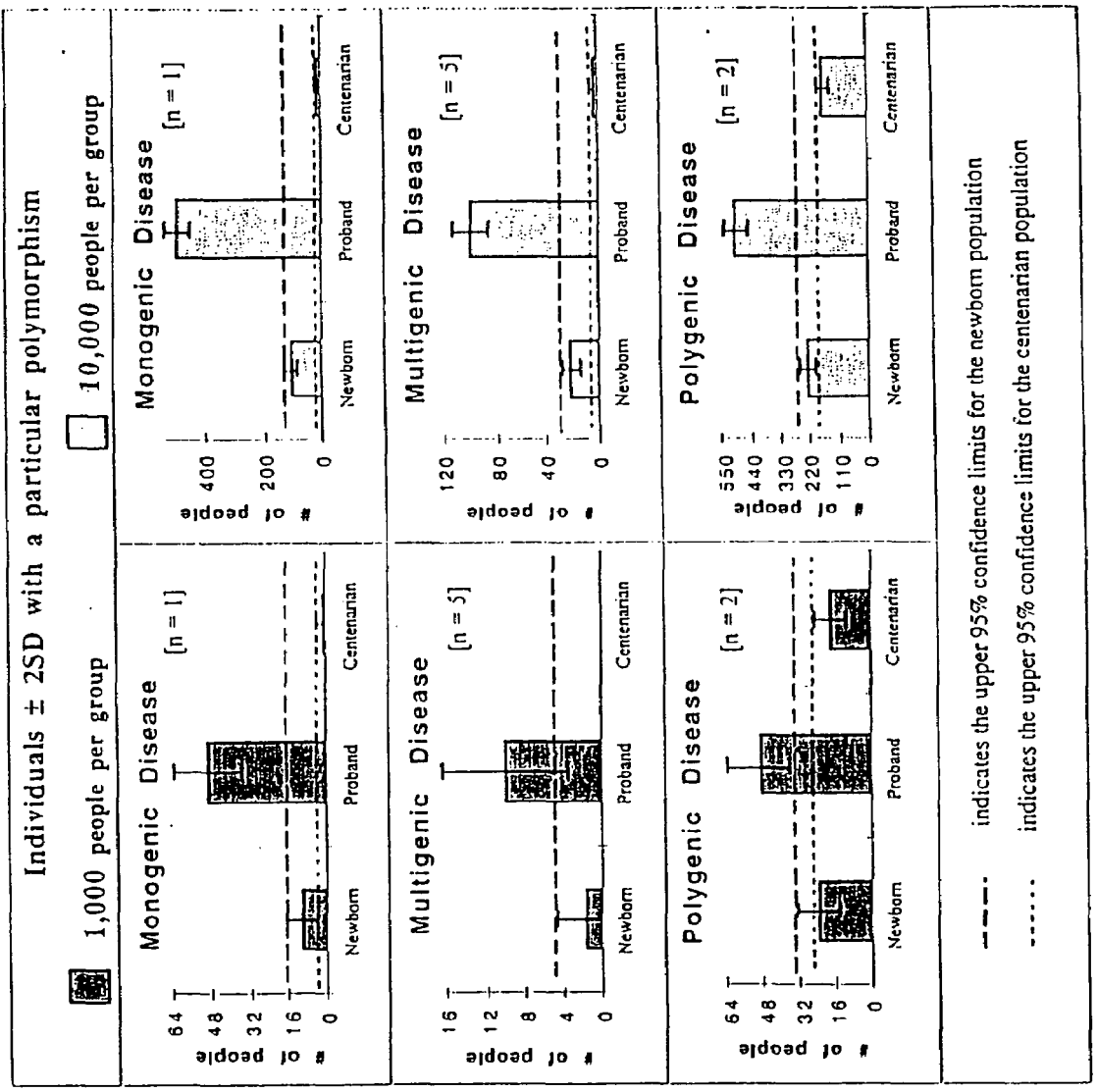
FIGS. 3A–3F are histograms which show the expected number of individuals±2SD with a particular polymorphism given population sizes of 1000 (FIGS. 3A–3C) and 10,000 (FIGS. 3D–3F) for the hypothetical situations of monogenic (FIGS. 3A and D), multigenic (n=5.

As shown in FIG. 2B, the fraction still at for pancreatic cancer risk among European American males after the age of 100 ($X(h,t)=X$ (1895, 100+)) is 0.044. Since there were about 5000 such individuals alive, 5000×0.044=220 of these centenarians would still be at risk of death by pancreatic cancer.

2.9. Consideration of Blood Sample Size

In order to determine allelic frequencies in a population with desirable statistical precision, the number of cells sampled per person must be large enough to reduce numerical variation and reasonably constant among all samples. One microliter of blood contains 1000–5000 white blood cells (McDonald, G. et al., 1970. Atlas of Haematology. E&S Livingstone Limited, London; Rifkind, R. et al., 1976. Fundamentals of hematology. Year Book Medical Publishers, Chicago). This is around 10–50 times more than the minimum number of 100 cells necessary to reduce variation for an allele present in only one person of the total pooled sample to an acceptable ±20%. A sample size comprising 1000 cells is sufficient to reduce numerical variation to less than 6.3% (95% confidence limits).

One need not create a separate mixed sample of 10,000 or more blood samples for each DNA sequence to be studied. We have improved the technique of using biotin labeled probes to isolate desired restriction fragments from human genomic DNA samples such that a 10,000 fold purification is obtained and leaves the remaining DNA sample available for many further extractions for other sequences (Li-Sucholeiki and Thilly, 1999, in press). We estimate that 1 milliliter samples containing at least 1 million WBCs from each of 10,000 persons could provide enough material to study a set of some $1 \times 10^6$ sequences of 100 or more bp each. This amount approaches that needed to study all genes in the human genome by the methods described herein.

2.10. Effect of Population Composition

Many pitfalls may be expected in the interpretation of studies of point mutations as a function of age. These are generally beyond the scope of this article but apply to all such studies, independent of the analytical approach used. For instance, newborns in 1998 may not reasonably approximate the ethnic distribution of the newborns of 1898 from which the centenarians of 1998 are drawn. Thus if a small recent immigrant population represented as 1% of the newborns were to carry a particular point mutation in 50% of their alleles the newborn population en toto would appear to have a SNP fraction of 0.5%. Assuming that the allele frequency were very low ($<10^{-4}$) in the older extant population, a significant difference between newborns and centenarians would be seen for this single point mutation. However, and this point cannot be overemphasized, our approach examines two or more rare point mutations within the same gene. For a conclusion that a gene has an important role in mortality, two or more different point mutations must decrease in the newborn/centenarians comprising, for instance, the set of all nonsense point mutations.

2.11. Point Mutations Linked to Other Risk Defining Polymorphisms

Cohorts with disease or lack of disease may be derived from a common or limited number of founders in the history of the human populations. Since the causal allele for disease or lack of disease can remain genetically linked for tens to hundreds of generations (Myant, N. et al., 1997. *Genomics*. 45:78–87), detection of an altered allele frequency within the proband population could indicate either the presence of a causal point mutation, or the presence of a point mutation that remains linked to an extragenic inherited mutation.

We would like to point out that the study of multiple point mutations in the same gene permits discrimination between these two possibilities. A change in frequency of a single point mutation among populations as a result of linkage can be differentiated from causality by comparing the frequencies of multiple point mutations that are expected to affect gene function among the study populations. If the frequency of one and only one point mutation changes between any two study populations, then linkage must be suspected as the cause. However, if multiple inactivating point mutations throughout the gene show similar changes in frequencies between any two populations, then the conclusion the gene in question plays a causal role in mortality is justified.

3. Discussion

We teach here that the use of a technology designed for in mutational spectrometry in human tissues, can be usefully employed in the task of defining rare point mutations which create risk for mortal disease. The technical advantages offered would make it possible to study sequences within any gene in samples drawn from 10,000 or more persons.

We also employed our recent extension of the Knudson-Moolgavkar multi-stage model of carcinogenesis to the data for age-dependent birthyear cohort-dependent mortality for pancreatic cancer. We intended in this exercise to suggest ways in which the observation of certain point mutations decreased frequencies in aging populations could be used to identify genes involved in the pathology of cancer and other age-dependent diseases.

Our suggested use of CDCE/hifiPCR in a methodical comparison of newborn, proband and extremely aged human populations is expected to permit identification of point mutations arising at frequencies as low as 0.005% with reasonable precision where 100,000 persons are sampled. Multiple point mutations in the same gene, several of which must decrease in the extremely aged and increase in the proband, would support a hypothesis that mutations in the gene itself create a subpopulation at risk. On the other hand, a decrease in the frequency of one and only one point mutation in a gene in the centenarian populations, while inactivating polymorphisms remain unchanged, would suggest linkage to a nearby allele defining risk for the observed disease. An interesting point is that a laboratory using this technology could compare newborn to centenarian point mutation spectra without prior knowledge of the physiological function of a DNA sequence studied. A finding of several point mutations decreasing in centenarians would identify that sequence as coding for a gene which affects longevity.

The methodology is also applicable to nonmortal diseases by identifying populations at risk through other phenotypic means, such as protein expression levels or enzyme activities. It is clear that the determination of the genetic variants within human populations which define risk of early death or which can confer sensitivity to environmental chemicals or pharmaceuticals will play an important role in both epidemiology and environmental health research.

EXAMPLE 2

Summary

The relationship between molecular mechanisms of mutagenesis and the actual processes by which most people get cancer are still poorly understood. One missing link is a physiologically-based but quantitative model uniting the processes of mutation, cell growth and turnover. Any useful model must also account for human heterogeneity for inherited traits and environmental experiences.

Such a coherent algebraic model for the age-specific incidence of cancer has been developing over the past fifty years. This development has been spurred primarily by the efforts of Nordling (1953. *Brit. J. Cancer*. 7:68–72), Armitage and Doll (1954. *Brit. J. Cancer*. 8:1–12), and Knudson and Moolgavkar (1992. *JNCI*. 84:610–618), whose work defined two rate-limiting stages identified with initiation and promotion stages in experimental carcinogenesis. Unfinished in these efforts was an accounting of population heterogeneity and a complete description of growth and genetic change during the growth of adenomas.

In an attempt to complete a unified model we present herein the first means to explicitly compute the essential parameters of the two-stage initiation—promotion model using colon cancer as an example. With public records from the 1930s to the present day, we first calculate the fraction at primary risk for each birth year cohort and note historical changes. We then calculate the product of rates for 'n' initiation mutations, the product of rates for 'm' promotion mutations and the average growth rate of the intermediate adenomatous colonies from which colon carcinomas arise.

We find that the population fraction at primary risk for colon cancer risk was historically invariant at about 42% for the birth year cohorts from 1860 through 1930. This was true for each of the four cohorts we examined (European- and African-Americans of each gender). Additionally, the data indicate an historical increase in the initiation mutation rates for the male cohorts and the promotion mutation rates for the female cohorts. Interestingly, the calculated rates for initiation mutations are in accord with mutation rates derived from observations of mutations in peripheral blood cells drawn from persons of different ages. Adenoma growth rates differed significantly between genders but were essentially historically invariant.

The model in its present form has also allowed us to calculate the rate of LOH or LOI in adenomas to result in the high LOH/LOI fractions in tumors. But it has not allowed us to specify the number of events, 'm' required during promotion.

Introduction

Colon cancer mortality rates are very low but rise exponentially from childhood to about age 60. The rates rise rapidly and approximately linearly from age 60 to 85, reach a maximum around age 90 and decreases significantly by ages 100–104. This is true both for males and females and for persons of European (FIGS. 5A and 5B) or non-European descent (FIGS. 6A and 6B; primarily African-Americans) recorded as dying of intestinal cancer in the United States from 1930 to the present day.

Seeking a quantitative model to account for these observations we posit that sporadic colon cancer arises in a subpopulation at "primary" risk as a result of inherited and/or environmental risk factors. Within this subpopulation, we apply the concepts of a three-stage carcinogenesis process: initiation, promotion and progression. Initiation is modeled as the accumulation of 'n' genetic events in any normal cell, giving rise to the first cell of an adenoma. In the surviving, slowly growing, adenoma, we model promotion as the acquisition of 'm' genetic events transforming any adenoma cell into a carcinoma cell. Progression is assumed to have a duration of less than three years and is modeled as occurring in zero years. Thus, the fact that colon cancer rates are low until late middle age is interpreted as the time required for a slowly growing adenoma to acquire one cell with the necessary genetic event(s) for growth as a carcinoma. The delay to onset of disease would be the average time necessary for an adenoma to produce a carcinoma.

The monotonic rise in cancer rates from childhood to age 80 is seen as a natural increase in the number of initiated cells as a function of age from birth. The early exponential rise is interpreted as a result of both the exponential increase of parenchymal cells from infancy to puberty and the exponential increase in an adenoma's cell number with time. The linear increase to high cancer rates is seen as a result of a linear increase in initiated cells as a function of age after puberty and a consequence of the constant number of stem cells in adults. These concepts, although somewhat extended by us (Herrero-Jimenez P. et al., 1998. *Mut. Res.* 400: 553–787), are common to the traditions of quantitative modeling of the carcinogenesis process.

We departed from previous work in our use of the maximum in the age-specific cancer mortality rates. This apparent maximum in the cancer mortality rate in old age was initially recognized but dismissed as an error of diagnosis and/or reporting in the elderly. Cook, Doll, and Fillingham (1969. *Int. J. Cancer.* 4:93–112), however, specifically reasoned that a true maximum in the age-dependent mortality rate would be expected if there were a distinct subpopulation at risk. By virtue of cancer risk, such a subpopulation would have a higher overall death rate than a subpopulation which had no risk of cancer. As a birth year cohort aged, there would be a smaller remaining fraction at risk and thus the observed cancer mortality rate in the surviving population could reach a maximum and decline. They also considered it possible that the apparent maximum and subsequent decline resulted from errors of diagnosis and reporting, but noted that "Visual inspection of the graphs show that when curvature is present, it usually occurs throughout the whole range of ages examined, and no relationship was found between the amount of downward curvature and the difficulty of diagnosis . . . ".

We returned to this question with a much larger data set, permitting analysis of birth year cohort specific age dependence of recorded cancer mortality for the entire American population of European and African descent over a period of more than sixty years (U.S. Department of Health and Human Services, Vital Statistics of the United States, (1937–1992), Volume II-Mortality Part A, US Government Printing Office, Hyattsvile, Md.; U.S. Bureau of the Census, Mortality Statistics, (1900–1936), Special Reports, Washington Government Printing Office). We have the advantage of observing mortality rates in the extremely aged in the last few decades in which the advent of government-sponsored health care for the elderly has reduced uncertainty as to the cause of death. These recent data confirm the suspicion of Cook et al. that a true maximum in cancer death rates exists. We have built on this confirmation to derive a more comprehensive model for age-specific cancer mortality rates in human populations.

We explicitly address the fact that the mortality rates are dependent on the effectiveness of treatment and on the accuracy of post-mortem diagnoses. We have assessed the former by examining the historical changes in the reported survival rates for colon cancer. With regard to underreporting, it is true that early in the twentieth century many deaths in the most elderly were reported as deaths by "old age" or "senility." However, the fraction of total deaths with such uninformative diagnoses has decreased steadily in the extremely aged throughout this century (U.S. Department of Health and Human Services, Vital Statistics of the United States, (1937–1992), Volume II-Mortality Part A, US Government Printing Office, Hyattsvile, Md.; U.S. Bureau of the Census, Mortality Statistics, (1900–1936), Special Reports, Washington Government Printing Office). As in the case of survival rates, we have used historical records on the number of uninformative diagnoses to estimate the level of underreporting for each age and birth year cohort.

We also have the advantages created by new understanding of the genetic changes leading to cancers in humans. We are persuaded that the somatic genetic evidence supports a model in which the loss of two active APC alleles is sufficient and necessary for initiation of most sporadic colon cancers (Powell, S. et al., 1992. *Nature.* 359:235–237; Levy, D. et al., 1994. *Cancer Res.* 54:5953–5958). However, our derived model is general for 'n' initiation mutations to permit facile testing of other hypotheses. Curiously, many mutations recorded in malignant tumors, such as in the ras proto-oncogenes or the TP53 gene, do not appear to be a part of the initiation or promotion processes as they appear to arise in sectors, but not the totality, of tumors in which they are measured. The absence of these mutations in every carcinoma cell suggests that they are not among the rate-limiting steps in normal tissue cells or adenomas which define the age-specific mortality rates modeled here. These post-adenomatous mutations may be considered important steps in tumor progression which, for our purposes, is considered a relatively rapid process of less than three years duration.

Building on our quantitative model for promotion we have also addressed the fact that early colon carcinomas and adenomas demonstrate marked loss of heterozygosity (LOH) for informative loci on all chromosomes, on average 22% (Vogelstein, B. et al., 1989. *Science.* 244:207–211; Vogelstein, B. et al., 1988. *N. Engl. J. Med.,* 319:525–32; Garcia-Patiño, E. et al., 1998. *Cancer Genet. Cytogenet.* 104:119–123; Resta, N. et al., 1998. *Cancer Res.* 58:4799–4801; Uhrhammer, N. et al.,1999. *Oncol. Rep.* 6:655–658; Ragnarsson, G. et al., 1999. *Br. J. Cancer.* 79:1468–1474). In a single study, loss of genomic imprinting (LOI) in colorectal carcinomas for a single marker was found to be 44% (Cui, H. et al., 1998. *Nat. Med.* 4:1276–1280). We use our model for 'm' promotion mutations to explore plausible mechanisms to account for these high LOH and LOI fractions.

We have placed most mathematical derivations in an appendix but have not hesitated to place the algebraic statements necessary to understanding the logic of the model in the text along with explanations of their physical meanings. The primary data sets from which all of our calculations arise are available through our website http://cehs4.mit.edu for the use of all researchers.

Materials: Population Data and Known Physiological Parameters

I. Primary Population Data Sets

A. Mortality Data

Annual age-specific mortality data for the U.S. population were obtained from the U.S. Department of Health and Human Services (Vital Statistics of the United States, (1937–1992), Volume II-Mortality Part A, US Government Printing Office, Hyattsvile, Md.) and the U.S. Bureau of the Census (Mortality Statistics, 1900–1936) (U.S. Bureau of the Census, Mortality Statistics, (1900–1936), Special Reports, Washington Government Printing Office). Population values were provided by the Duke Center for Demographic Studies for the years 1950 to 1992. For previous years, we derived population estimates directly from census counts for those states and counties reporting to the national death registries. Combined, these data sets permitted calculation of the age specific mortality rate for each birth year, 'h', designated OBS(h,t) for "OBServed" colon cancer mortality rate.

$$OBS(h, t) = \frac{\text{recorded deaths from intestinal cancer from birth cohort } H \text{ at age } t}{\text{recorded populations size from birth cohort } h \text{ at age } t} \quad \text{equation 5}$$

FIGS. 5A, 5B, 6A and 6B summarized the age-specific colon cancer mortality records for the birth years between 1840 and 1930 for European and Non-European-Americans respectively. The age-specific mortality data were grouped in 5-year intervals 0–4,5–9, . . . , 90–94, 95–99, 100+. The mean age of these groups is approximately 2.5, 7.5, . . . , 97.5 and 102.5 and accounts for our use of these ages herein. To simplify presentation of data, we have summed deaths and populations of individuals born in the same decade. The 1830s denotes persons born in 1830–1839 and so forth.

Intestinal cancer records are available since 1930, as opposed to 1958 for colon cancer when specific diagnosis became available. We used these data to approximate colon cancer deaths; deaths by cancer of the small intestine represented only 3% of the total number of deaths from intestinal cancer in the period during which colon cancer was specifically recorded (U.S. Department of Health and Human Services, Vital Statistics of the United States, (1937–1992), Volume II-Mortality Part A, US Government Printing Office, Hyattsvile, Md.).

The population numbers for individuals described as "non-white" would include persons of Native American and Asian heritage as well as African heritage. However, the U.S. demographics during the period when the term "non-white" was used as a descriptive term was more than 75% of African descent (U.S. Department of Health and Human Services, Vital Statistics of the United States, (1937–1992), Volume II-Mortality Part A, US Government Printing Office, Hyattsvile, Md.).

B. Survival Data & Estimates

For each birth year cohort h and each age t within each cohort there is an associated relative 5-year survival rate for colon cancer S(h,t). S(h,t) represents the probability of surviving those causes linked to colon cancer.

$$S(h, t) = \frac{(\text{recorded colon cancer survivors at age } t + 5, \text{ diagnosed at age } t)}{(\text{recorded diagnoses of colon cancer at age } t) \times (\text{survival rate for all forms of death, age } t + 5)} \quad \text{equation 6}$$

Here, we use the relative survival rate rather than the observed survival rate, recognizing that individuals who were diagnosed with colon cancer could have died of an unrelated form of death within the 5-year period after diagnosis.

Naturally, improvements in colon cancer diagnosis and therapy have contributed to a historically increasing value of S(h,t). An important complication, however, is that at ages greater than 75 there is a diminishing probability that either early diagnosis will be accomplished and/or that rigorous forms of therapy will be applied. Unfortunately, the data set for these values is incomplete and our effort proceeds with some approximations.

Eisenberg et al. (Eisenberg, H. et al., Cancer in Connecticut: Survival Experience, 1935–1962, Hartford, Conn., Connecticut State Department of Health, ©1968) have summarized the age-specific relative survival rates for 1935 to 1959 within the state of Connecticut for both males and females up to ages 65–74, and estimated for ages greater than 75. The NCI Monograph No. 6 (Cutler, S. and Ederer, F. (eds), End Results and Mortality Trends in Cancer; NCI Monograph No. 6, National Cancer Institute, Bethesda, Md., ©1961) summarized similar relative survival rates for 1950 to 1957 for both males and females, including both a larger set of hospital registries, and relative survival rates for untreated individuals. The Cancer Patient Survival Report Number 5 (Axtell, L. et al. (eds), Cancer Patient Survival; Report Number 5, National Cancer Institute, Bethesda, Md., ©1976) extended this work to the period of 1950 to 1972, including survival rates for patients of both European and African descent. Gloeckler et al. similarly reports the relative survival rates for the period of 1973 to 1975 by age, gender, and race. Last, the SEER Cancer Statistics Reviews (Miller, B. et al., (eds), SEER Cancer Statistics Review: 1973–1990, National Cancer Institute, Bethesda, Md., ©1993; Ries, L. et al., (eds), SEER Cancer Statistics Review: 1973–1994, National Cancer Institute, Bethesda, Md., ©1997; Ries, L. et al., (eds), SEER Cancer Statistics Review: 1973–1996, National Cancer Institute, Bethesda, Md., ©1999) have recorded the 5-year relative survival rates for 1983 through 1991.

Beart et al. (1995. J. Amer. Coll. Surg. 181:225–236) have reported the age-specific relative survival rates for 1983, although gender and race were not specified. Beart's overall survival estimates for the early 1980s were about 10% lower than as reported by SEER (Ries, L. et al., (eds), SEER Cancer Statistics Review: 1973–1996, National Cancer Institute, Bethesda, Md., ©1999). Consequently, for the 1980s, we chose to use SEER's reported survival rates decreased by 5% to represent the average of SEER and Beart et al.

Reported survival rates did not account for those deaths of individuals first diagnosed with cancer at the time of death. The percentage of 'incidences at autopsy' is 1–2% for the 1990s [personal communication, L.A.G. Ries, SEER]. For diagnostic years 1935–79 the percentage of 'incidences at autopsy' for the state of Connecticut was generally 1–3%, but was shown to increase as a function of age (Heston, J. et al. (eds), Forty-five years of Cancer Incidence in Connecticut: 1935–79, National Cancer Institute, Bethesda, Md., ©1986).

Survival rates are approximately constant between ages 40 and 75 in recent decades (Ries, L. et al., 1983. *JNCI.* 70:693–707; Miller, B. et al., (eds), SEER Cancer Statistics Review: 1973–1990, National Cancer Institute, Bethesda, Md., ©1993; Ries, L. et al., (eds), SEER Cancer Statistics Review: 1973–1994, National Cancer Institute, Bethesda, Md., ©1997; Ries, L. et al., (eds), SEER Cancer Statistics Review: 1973–1996, National Cancer Institute, Bethesda, Md., ©1999). However, Beart, R. et al. (1995. *J. Amer. Coll. Surg.* 181:225–236) extended the survival data to 80 years and found survival rates decreased significantly from 70–79 and >80 years of age. Survival rates appear to decrease even further in extreme old age when colon cancer is more often detected in an advanced stage. In persons over 80 years of age, only 2.4% of all colon tumors were treated by surgery and chemotherapy, compared to 26.3% for persons less than 50 year olds (Beart, R. et al., 1995. *J. Amer. Coll. Surg.* 181:225–236). As an estimate, we use a survival rate for centenarians of 3–4%, the survival rate for untreated tumors for 75+ year olds (Cutler, S. and Ederer, F. (eds), End Results and Mortality Trends in Cancer; NCI Monograph No. 6, National Cancer Institute, Bethesda, Md., ©1961.) We interpolate between this estimate and the other data to approximate the survival for any unspecified ages.

FIGS. 7A and 7B illustrate these points for European-American females born between the 1840s and 1930s. The data recorded by year of diagnosis in FIG. 7A are converted into age-specifi relative survival values by year of birth in FIG. 7B. Where values were unknown, estimates were interpolated. Survival rates reported for the age ranges "under 45" and "above 75," are plotted at ages 40 and 80, respectively, as these are approximately the average ages of individuals dying of colon cancer in these cohorts. S(h,t) increases steadily with historical time which creates a steady age specific increase in S(h,t) for any particular birth year cohort, but which still decreases markedly in extreme old age.

Table 2 summarizes the relative survival rates by year of diagnosis, using averages for those years for which more than one value were available. Averages were weighted according to the numbers of patients examined in each study. To estimate relative survival rates for Non-European-Americans, we referred to the African-American survival rate data set for the 1950s through the 1990s, as African-Americans comprised more than 75% of the Non-European population. Estimates for the 1940s and 1930s cohorts of Non-Europeans were interpolated assuming that the change in the survival rate for European-Americans was proportional to the change in the survival rate of Non-European-Americans during this period. No estimates were allowed to drop below the reported survival rates for untreated individuals (Cutler, S. and Ederer, F. (eds), End Results and Mortality Trends in Cancer; NCI Monograph No. 6, National Cancer Institute, Bethesda, Md., ©1961).

TABLE 2

Summary of the relative survival rates by year of diagnosis

| | \multicolumn{6}{c}{Ages:} | | | | | |
|---|---|---|---|---|---|---|
| | 0–44 | 45–54 | 55–64 | 65–74 | 75+ | 100+ |
| 1990s | | | | | | |
| EAM | 0.58 | 0.62 | 0.65 | 0.66 | 0.59 | 0.03 |
| EAF | 0.59 | 0.65 | 0.62 | 0.64 | 0.60 | 0.04 |
| NEAM | 0.51 | 0.54 | 0.55 | 0.52 | 0.45 | 0.03 |
| NEAF | 0.55 | 0.53 | 0.56 | 0.53 | 0.46 | 0.04 |

TABLE 2-continued

Summary of the relative survival rates by year of diagnosis

| | Ages: | | | | | |
|---|---|---|---|---|---|---|
| | 0–44 | 45–54 | 55–64 | 65–74 | 75+ | 100+ |
| 1980s | | | | | | |
| EAM | 0.49 | 0.59 | 0.59 | 0.60 | 0.57 | 0.03 |
| EAF | 0.58 | 0.56 | 0.56 | 0.57 | 0.55 | 0.04 |
| NEAM | 0.44 | 0.49 | 0.49 | 0.47 | 0.37 | 0.03 |
| NEAF | 0.52 | 0.54 | 0.53 | 0.43 | 0.41 | 0.04 |
| 1970s | | | | | | |
| EAM | 0.47 | 0.48 | 0.48 | 0.48 | 0.44 | 003 |
| EAF | 0.58 | 0.50 | 0.50 | 0.48 | 0.46 | 0.04 |
| NEAM | 0.42 | 0.46 | 0.45 | 0.38 | 0.32 | 0.03 |
| NEAF | 0.53 | 0.50 | 0.45 | 0.50 | 0.37 | 0.04 |
| 1960s | | | | | | |
| EAM | 0.50 | 0.45 | 0.45 | 0.44 | 0.37 | 0.03 |
| EAF | 0.50 | 0.48 | 0.48 | 0.47 | 0.42 | 0.04 |
| NEAM | 0.29 | 0.42 | 0.31 | 0.29 | 0.25 | 0.03 |
| NEAF | 0.36 | 0.46 | 0.38 | 0.30 | 0.34 | 0.04 |
| 1950s | | | | | | |
| EAM | 0.42 | 0.46 | 0.40 | 0.38 | 0.32 | 0.03 |
| EAF | 0.46 | 0.46 | 0.46 | 0.42 | 0.38 | 0.04 |
| NEAM | 0.28 | 0.37 | 0.25 | 0.32 | 0.18 | 0.03 |
| NEAF | 0.44 | 0.36 | 0.33 | 0.24 | 0.15 | 0.04 |
| 1940s | | | | | | |
| EAM | 0.27 | 0.33 | 0.29 | 0.21 | 0.17 | 0.03 |
| EAF | 0.34 | 0.34 | 0.35 | 0.28 | 0.24 | 0.04 |
| NEAM | 0.18 | 0.26 | 0.18 | 0.18 | 0.09 | 0.03 |
| NEAF | 0.30 | 0.27 | 0.25 | 0.16 | 0.10 | 0.04 |
| 1930s | | | | | | |
| EAM | 0.30 | 0.27 | 0.20 | 0.09 | 0.00 | 0.03 |
| EAF | 0.25 | 0.17 | 0.18 | 0.11 | 0.07 | 0.04 |
| NEAM | 0.20 | 0.22 | 0.12 | 0.07 | 0.04 | 0.03 |
| NEAF | 0.22 | 0.13 | 0.13 | 0.07 | 0.04 | 0.04 |
| Untreated | | | | | | |
| Males | 0.00 | 0.10 | 0.11 | 0.07 | 0.03 | |
| Females | 0.11 | 0.07 | 0.07 | 0.07 | 0.04 | |

*Reported as Other and Untreated [20]

C. Reporting Data: Estimates of Error

It is obvious that the numerator defining OBS(h,t) in Equation 5 will be affected by the probability that an actual colon cancer mortality is recorded as such. It is equally obvious that there are no records of inadequate diagnosis per se. In our previous attempt et al. (1998. *Mut. Res.* 400: 553–787), we faced this problem with regard to the completeness of the mortality records for the extremely aged and found that we could improve our estimate of mortality to some extent by noting the number of deaths in a cohort without any adequate diagnosis as a function of age. For instance, in centenarians we noted this number was about 20% in the 1930s for European-American males but decreased to less than 5% by the 1950s (Herrero-Jimenez P. et al., 1998. *Mut. Res.* 400:553–787). Thus we have inspected the historical record for the number of deaths with vague or unrecorded diagnoses for all ages, genders, and ethnic groups, for each birth year cohort analyzed. These data create a matrix for each demographic group defining an upper estimate of the probability of accurately recording the cause of death as the function R(h,t).

$$R(h, t) = \frac{\text{recorded deaths from specified causes from birth cohort } h \text{ at age } t}{\text{all recorded deaths from birth cohort } h \text{ at age } t} \quad \text{equation 7}$$

Figure 8:
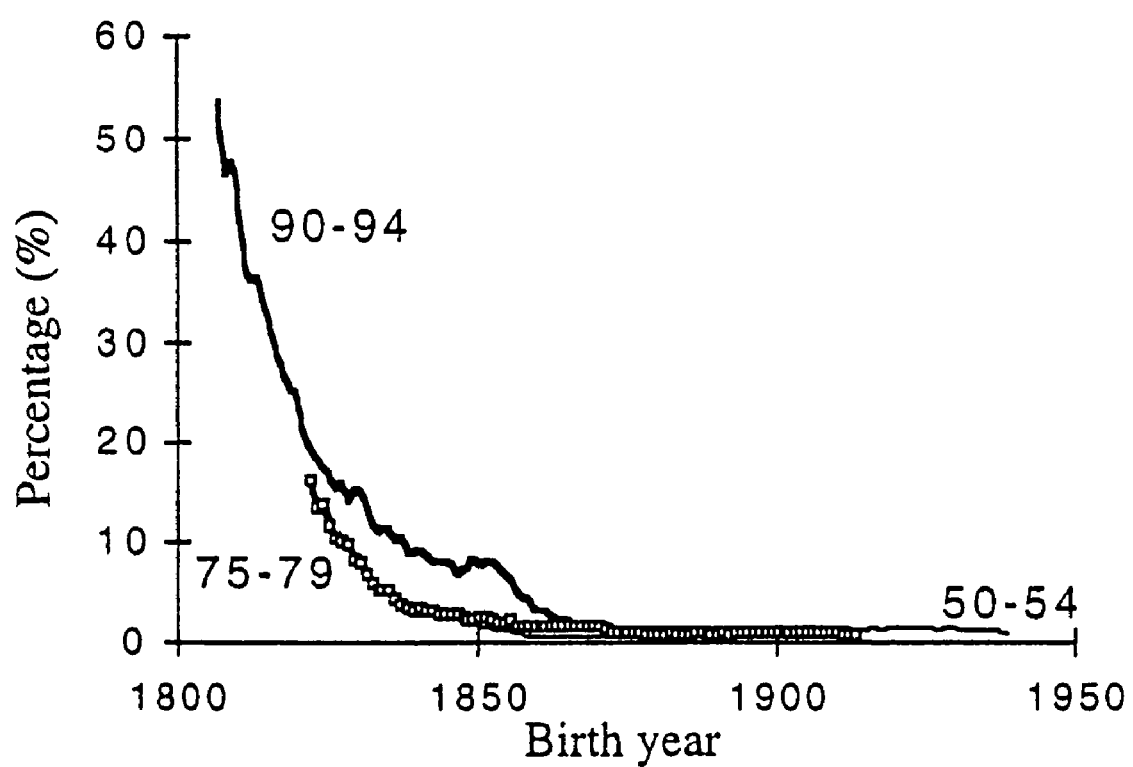
FIG. 8 is a graph demonstrating the percentage of all deaths with vague diagnoses for European-American males of ages 50–54, 75–79, and 90–94 as a function of their year of birth.

FIG. 8 shows the percentage of all deaths with vague diagnoses plotted as a function of the birth year for several age groups of European-American males. The assumption here is that the proportion of colon cancer deaths among all deaths with unrecorded diagnoses is about the same as the proportion of colon cancers among all deaths with recorded diagnoses.

Application of this assumption still underestimates the true colon cancer mortality fraction. Since about 50% of present deaths are recorded as due to cardiovascular or cerebrovascular causes, small overestimates in these diagnoses would lead to large underestimates of mortality from any other specific disease.

Furthermore, a diagnosis of colon cancer may be in error, particularly if a mass in the colon were a secondary tumor from another organ. This kind of error has been addressed in a number of studies in which pathological samples were reviewed. Colon cancer was actually found to be somewhat over-reported in death certificates primarily because of inclusion of a portion of rectal tumors (Percy, C. et al., Cancer Mortality in the U.S., 1950–1957, Appendix III, National Cancer Institute, Bethesda, Md., ©1982).

D. Mortality data Adjusted for Historical and Age-Specific Survival Probability and Reporting Error: Definition of OBS*(h,t).

We can now use these available data to improve our estimates of actual occurrence rates of colon cancer. We are persuaded that the amended data set is of sufficient accuracy to permit application of the mathematical analyses we employ. Our models are, however, explicit and allow exploration of the effect of errors in survival or reporting data on the estimation of parameters.

FIGS. 9A, 9B, 10A and 10B recast the data of FIGS. 5A, 5B, 6A and 6B using all of our estimates of S(h,t) and R(h,t) with OBS(h,t) to define a new function OBS*(h,t).

$$OBS^*(h,t) = OBS(h,t) \div [R(h,t)(1-S(h,t))] \quad \text{Equation 8}$$

These figures are our best estimates of what colon cancer mortality rates would have been in a world with accurate diagnosis and recording but no therapy of any kind. In a sense it is a reconstruction of "incidence" data in a world with accurate diagnosis but without effective therapy.

Figure 5A:
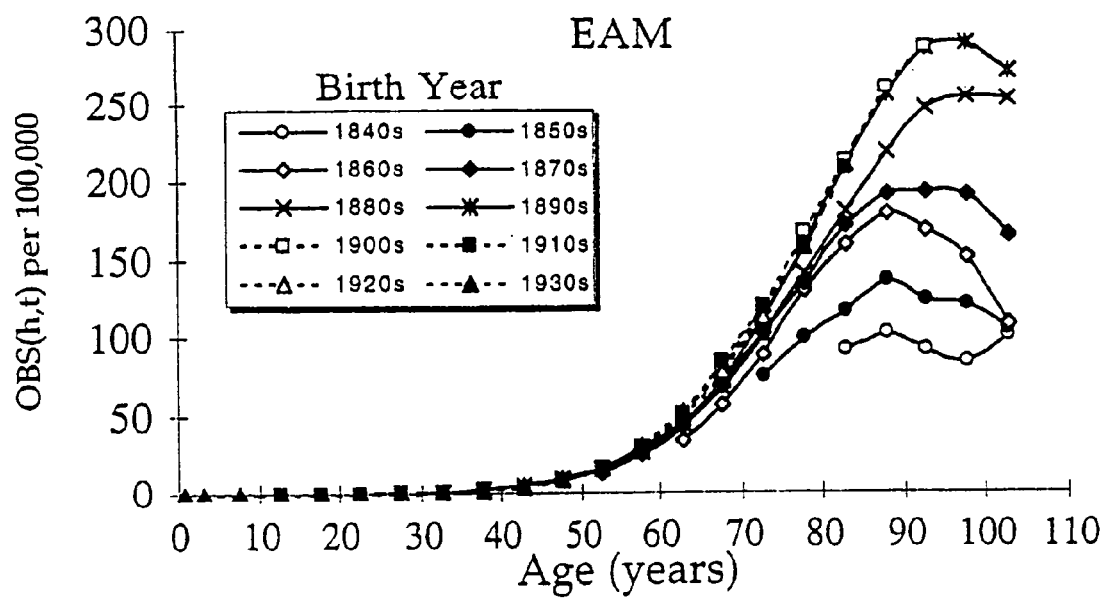
FIGS. 5A and 5B are graphs of intestinal cancer age- and birth year-specific mortality curves for EAM (FIG. 5A) and EAF (FIG. 5B; data recorded 1930–1992).
Figure 5B:
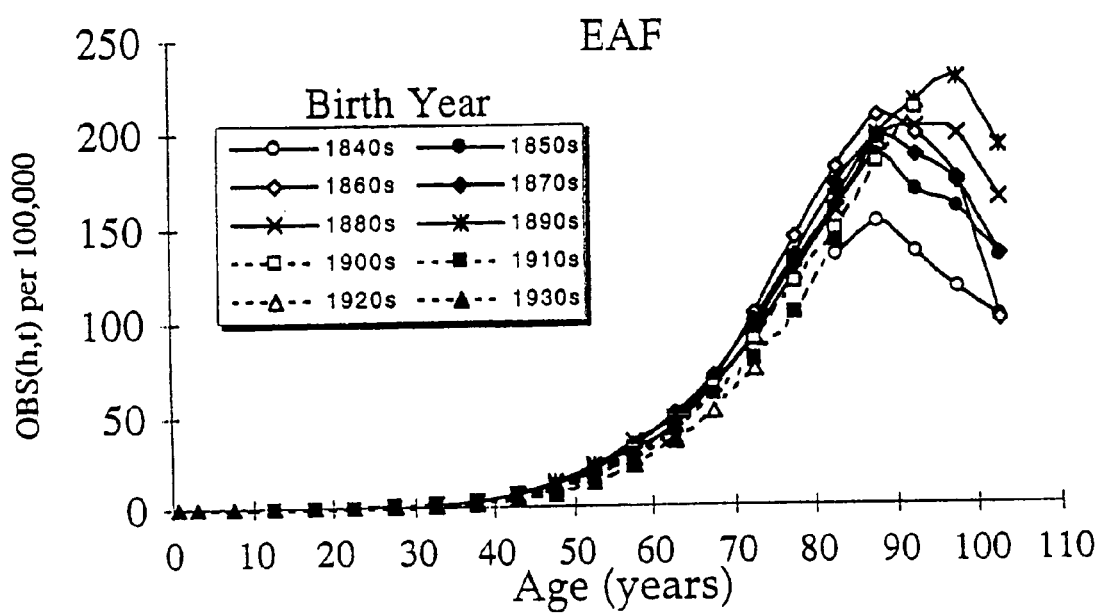
Figure 6A:
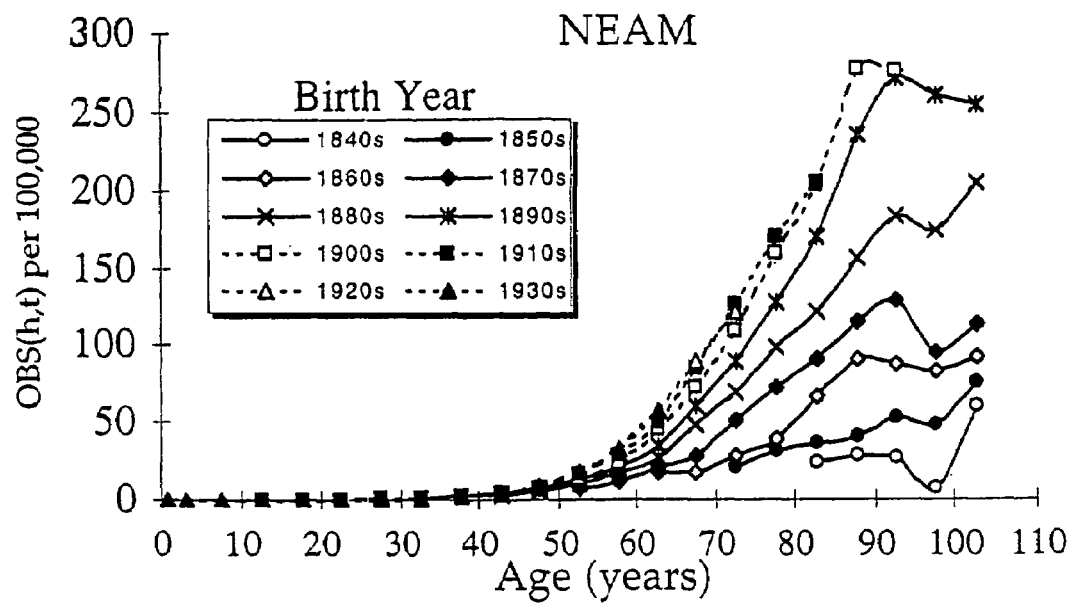
FIGS. 6A and 6B are graphs of intestinal cancer age- and birth year-specific mortality curves for Non-European-American males (NEAM.
Figure 6B:
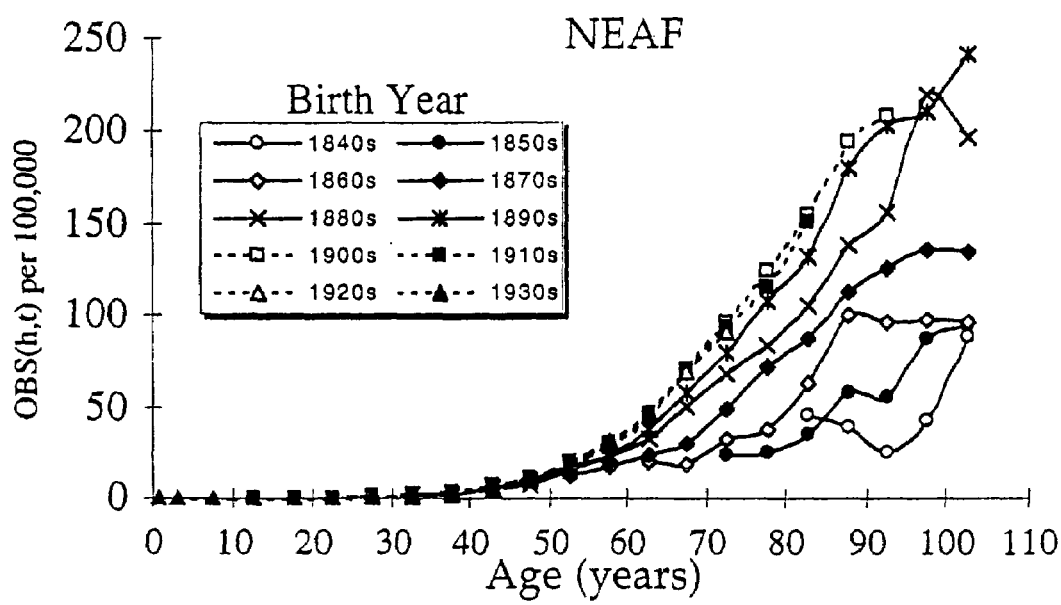
Figure 9A:
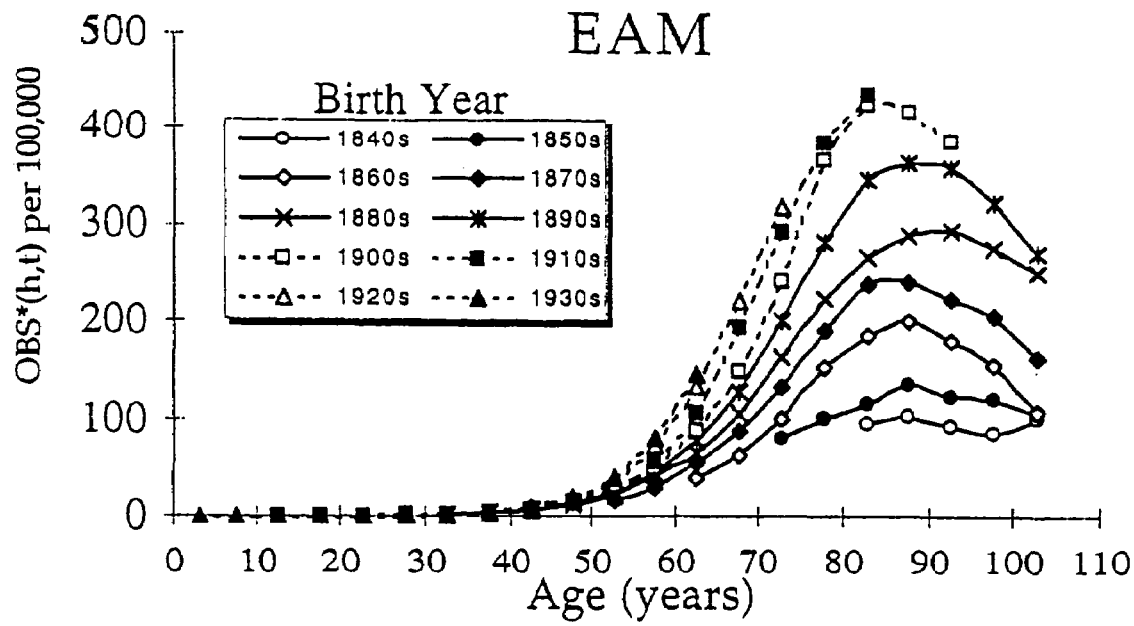
FIGS. 9A and 9B are graphs of colon cancer age- and birth year-specific mortality curves adjusted for historical changes in under-reporting and survival rates among European-American males (FIG. 9A) and European-American females (FIG. 9B). OBS*(h,t)=OBS(h,t)÷[R(h,t) (1−S(h,t))]
Figure 9B:
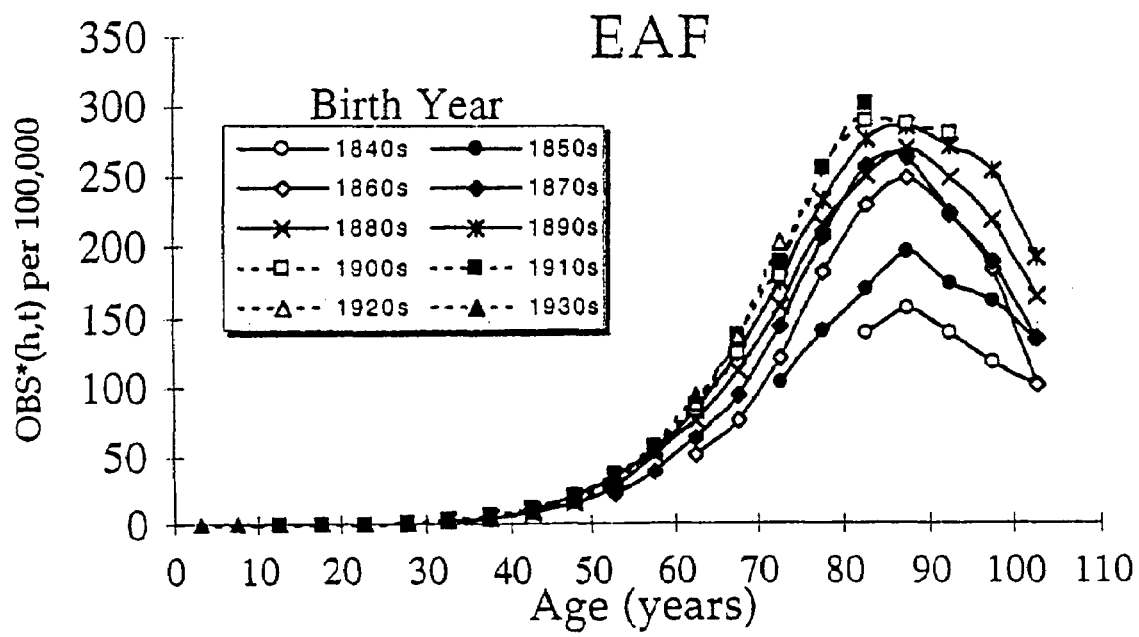

An example of the importance of accounting for survival and reporting error may be noted by comparing the function OBS(1880s,t) for the EAM cohort of FIG. 5A to the function OBS*(1880s,t) for the same cohort in FIG. 9A. In the former, OBS(h,t) appears to reach a stable maximum plateau by age 90, but in the latter, OBS*(h,t) shows a clear maximum declining through age 102.5. A similar effect may be noted by comparing within the NEAF cohort OBS(1870s, t) to OBS*(1870s,t).

E. Known Physiological Parameters.

Cell Kinetic Rates

One of our goals is to evaluate mutation rates per cell division from the cancer mortality data. For this we require cell kinetic parameters. In our previous effort (Herrero-Jimenez P. et al., 1998. Mut. Res. 400:553–787), we employed an estimate of 45 minutes for the length of mitosis in vivo. This was not based on actual in vivo observations but relied on observations on the length of mitoses in vitro. It appears that this was a significant underestimate. Wright, N. et al. (1973. Gut. 14:603–606) reports that the duration of mitosis for the small intestine is 1–1.5 hours in vivo. Likewise, Weinstein, W. et al. (1973. Gastroenterology. 64:A137/820) found that the mitotic time for the human jejunum is 1.4 to 2.2 hours in vivo (no data were found for normal colon). This suggests that we overestimated our kinetic rates by a factor of 2. The lengths of mitosis and apoptosis may additionally differ among normal transition cells, adenoma and carcinoma cells. Our treatment here assumes they are in fact the same for these three cases.

However, we also mistakenly assumed that the window of detection for mitosis when looking at a tissue section on a slide was twice the length of mitosis (Herrero-Jimenez P. et al., 1998. Mut. Res. 400:553–787), when in fact it is simply the length of mitosis. These two factors fortuitously negated each other, so that the values for the cell kinetic parameters in adenomas and carcinomas we have previously reported are, accidentally, correct. Our estimate of the cell division rate in colon adenomas, $\alpha$, is 9 divisions per year and the cell division rate in early colon carcinomas, $\alpha c$, is about 29. We find the cell death rate in colon adenomas, $\beta$, and early carcinomas, $\beta c$, to be approximately equal, $\beta \approx \beta c \approx 9$. We did need to correct for an error in estimating the division and death rate of normal colon epithelium, t. Only half of the cells would undergo division, since one half are non-dividing terminal cells. The actual estimate for it would be twice our previous estimate of 1.5 of divisions or deaths per year (Herrero-Jimenez P. et al., 1998. Mut. Res. 400:553–787). The turnover rate of normal colon epithelial cells is thus approximately 3.

Cell Number

In order to estimate mutation rates, we also needed to know the number of colonic epithelial cells as a function of age. We estimated that the volume of an organ increases proportionally to the mass of an average individual. Since the colon is approximately a cylindrical tube, we inferred that the number of colonic epithelial cells is proportional to body mass to the two-thirds power.

Figure 11A:
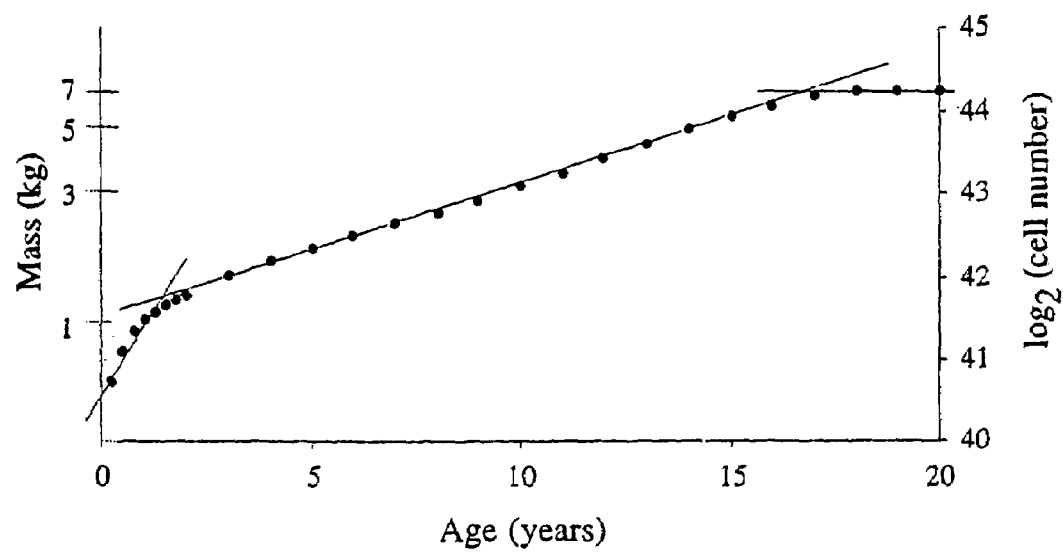
FIGS. 11A and 11B are graphs of the mass of males (FIG. 11A) or females (FIG. 11B) as a function of age (Hamill, P. V., et al., *Am. J. Clin. Nutr.*, 32(3), 607–629 (1979)).
Figure 11B:
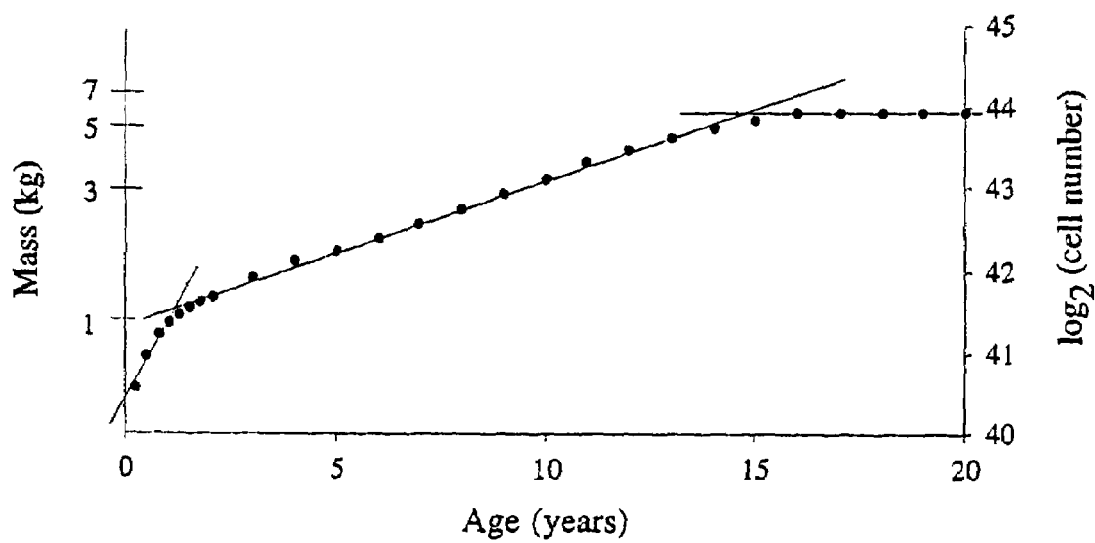

FIGS. 11A and 11B show the masses of average males and females respectively as a function of age. For both males and females, body mass increases exponentially from age 1.5 years to 14.5 years in females and 16.5 years in males. A higher constant rate is obtained for growth between birth and age 1.5 years.

From FIGS. 11A and 11B, we estimated the growth rates of males and females from the slope of the log2 of the mass of average individuals for the age intervals 0–1.5 and 1.5–14.5 for females and 1.5 to 16.5 for males. These estimated growth rates for mass were then multiplied by 2/3 to obtain our estimates for the growth rates of colonic epithelial cells.

| Ages | Growth rate (mass) | Growth rate (colonic cells) |
|---|---|---|
| Males | | |
| 0–1.5 | 1.23 | 0.82 |
| 1.5–16.5 | 0.159 | 0.106 |
| Females | | |
| 0–1.5 | 1.17 | 0.78 |
| 1.5–16.5 | 0.167 | 0.111 |

The number of colon epithelial cells as a function of age, $N_a$, can therefore be written as a discontinuous function based upon the number of colonic epithelial cells in an adult, $N_{max}$. We illustrate this with the values for males.

$$N_{a,males} = \begin{cases} N_{max} = \text{cells in adult organ} & a > 16.5 \\ N_{max} \div 2^{0.106(16.5-a)} & 1.5 < a \le 16.5 \\ N_{max} \div 2^{0.106(15)+0.82(1.5-a)} & 0 \le a \le 1.5 \end{cases} \quad \text{Equation 9}$$

The number of colon cells in a female follows by similar reasoning.

One should also account for the fact that the weight of an average female is about 80% that of a male at age 18 (Hamill, P. et al., 1979. *Am. J. Clin. Nutr.* 32:607–629). The estimate in Herrero-Jimenez et al. (1998. *Mut. Res.* 400: 553–787) for the number of cells in a colon, $N_{max}=8.5\times10^{10}$ cells, made no distinction as to the gender. As a better approximation, we have used herein an estimate of $9.1\times10^{10}$ colonic cells in an adult male colon and $7.9\times10^{10}$ in an adult female.

Somatic Mutation Rates in Humans

Figure 12:
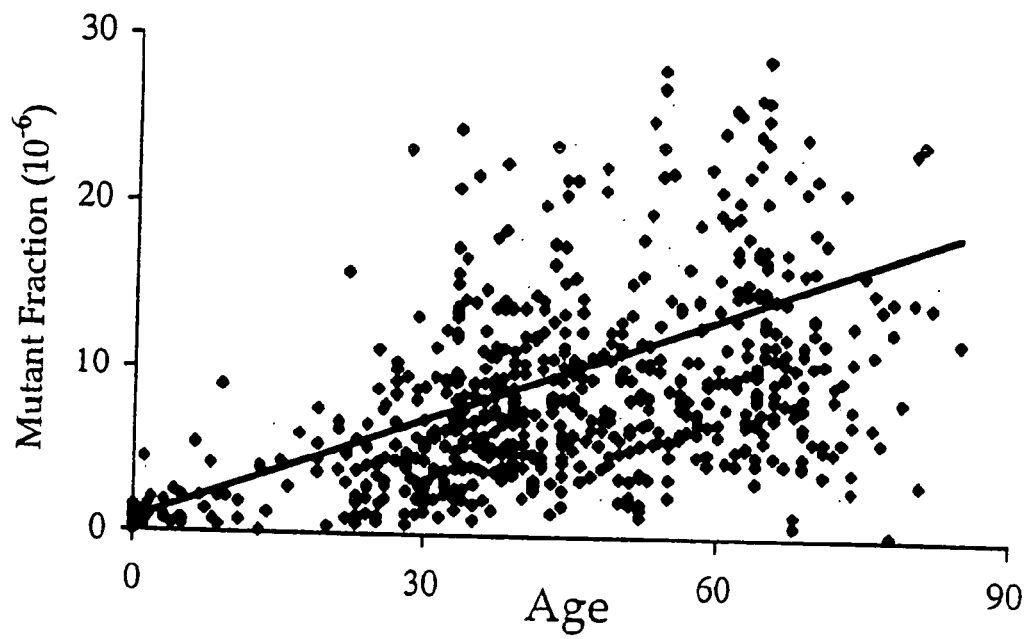
FIG. 12 is a plot of the mutant fraction of the Hprt locus as a function of age (n=740); the slope of the line is $2.1 \times 10^{-7}$ Hprt mutations per cell year.

We have compiled all published reports of the age-specific mutant fraction at the Hprt locus in human peripheral T cells (Bigbee, W. et al., 1998. *Mut. Res.* 397:119–36; Branda, R. et al., 1993. *Mut. Res.* 285:267–79; Davies, M. et al., 1992. *Mut. Res.* 265:165–71; Finette. B. et al., 1994. *Mut. Res.* 308:223–31; Henderson, L. et al., 1986. *Mutagenesis.* 1: 195–200; Hirai, Y. et al., 1995. *Mut. Res.* 329: 183–96; Hou, S. et al., 1995. *Mol. Mutagen.* 25:97–105; Huttner, E. et al., 1995. *Mut. Res.* 348:83–91; Liu, Y. et al., 1997. *Environ. Mol. Mutagen.* 29:36–45; McGinniss, M. et al., 1990. *Mut. Res.* 240:117–26; Tates, A. et al., 1991. *Mut. Res.* 253:199–213). Observations with absolute cloning efficiencies less than 20% were excluded to eliminate this form of bias. FIG. 12 shows these mutant fractions as a function of age. These data show a similar distribution around the mean for all age groups, 0–9, 10–19, etc. up to age 75 after which the number of persons with relatively high mutant fractions appears to decline markedly. Using all of the data from ages 0–75, we calculate a constant rate of Hprt loss of $2.1\times10^{-7}$ mutations per stem cell year or about $0.7\times10^{-7}$ mutations per stem cell division. This estimate assumes 3 stem cell divisions per year for pluripotent cells. In human B-cell cultures, the observed spontaneous rates of mutation at the Hprt locus ranges from 0.5 to $2.5\times10^{-7}$ mutations per cell division (Gennett, I. and Thilly, W., 1988. *Mut. Res.* 201:149–60; Oller, A. and Thilly, W., 1992. *J. Mol. Biol.* 228:813–26; Chen, J. and Thilly, W., 1996. *Mut. Res.* 357(1–2), 209–17). These in vivo and in vitro estimates are in reasonable agreement and represent loss of an active gene copy by point mutations and large deletions but not by recombination.

Two estimates of LOH rates in humans differ significantly. Grist et al. (1992. *Mut. Res.* 266:189–196) reported that the sum of all pathways for loss of heterozygosity of the HLA-A locus in peripheral T-cells precursors was about $6.6\times10^{-7}$ events per cell year or $2.2\times10^{-7}$ per stem cell division. However, Fuller et al. (1990. *Br. J. Cancer.* 61, 382–384) and Jass, J. and Edgar, S. (1994. *Pathology.* 26:414–417) report observations which allowed us to calculate rates of colon unicryptal LOH of about $2\times10^{-5}$ per stem cell year or about $7\times10^{-6}$ LOH events per colonic stem cell division, 30 times higher than LOH rates seen in blood cells. A crypt's negative phenotype for O-acetylation of sialic acid presumably by loss of an active allele of O-acetylate transferase was used as the LOH assay.

Methods: Logical and Mathematical Approaches

A. The Number of Subpopulations at Risk.

The data of FIGS. 5A, 5B, 6A and 6B comprise all recorded deaths from intestinal cancers which we use as an approximation to colon cancer. When survival and under-reporting are accounted, as in FIGS. 9A, 9B, 10A and 10B, it is clear by inspection that these functions reach a maximum in old age. This repeated observation is consistent with expectation for a population in which only some fraction is at lifetime risk of colon cancer. While recognizing that other explanations for such a maximum may be devised we build our analysis on the validity of the subpopulation at risk assumption and the certain knowledge that human populations display a high degree of genetic heterogeneity.

These data do not, however, separate deaths in families with familial adenomatous polyposis coli (FAPC) from deaths in families with hereditary nonpolyposis colon cancer (HNPCC or Lynch syndrome) or from deaths by "sporadic" colon cancer. "Sporadic" cancers themselves are undifferentiated with regard to the possibility that there are independent pathways of genetic changes leading to several different kinds of sporadic colon cancer.

We posit that there could be multiple pathways to cancer in any particular organ. The potential for and rate of transit of these pathways would be determined by unknown but ascertainable alleles of tumor suppressor genes and genes which effect the rates of genetic changes and cell kinetic rates in normal tissues and preneoplastic colonies (adenomas). These alleles would be distributed throughout the entire population.

Figure 13:
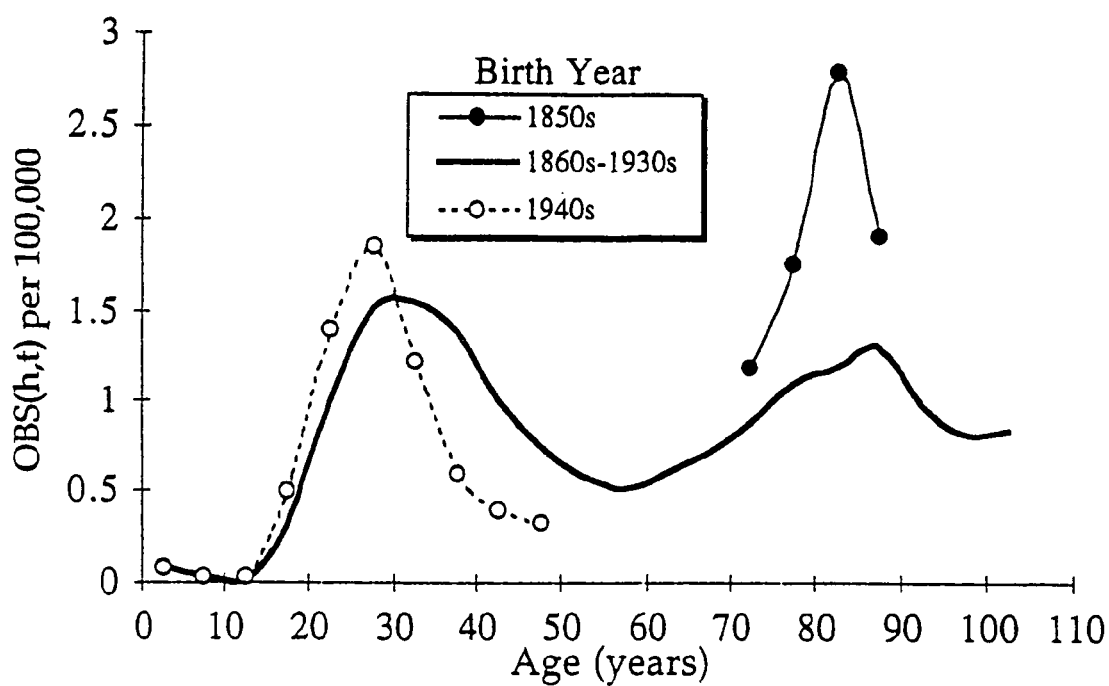
FIG. 13 is a graph demonstrating testicular cancer age- and birth year-specific mortality for EAM.

There are cancers of organs for which such a treatment assuming multiple pathways is obviously required. In FIG. 13, we show OBS(h,t) for death by testicular cancer in which two populations are clearly evident, one with all deaths occurring between ages 15 and 40 and a second group in which deaths begin to be observed after age 50. Mortality data lump the deaths from multiple independent pathways together perforce.

To begin deconvolution of the existing mortality data for colon cancer, we note that however many possible pathways to mortal colon cancer inherent in a particular individual, death can be caused by only one.

Thus we may stipulate that the number of colon cancer deaths must be the sum of the deaths caused by each of the potentially multiple pathways:

$$OBS(h,t)=OBS1(h,t)+OBS2(h,t)+OBS3(h,t)+ \quad \text{Equation 10}$$

In the case of colon cancer, we know that mortality from FAPC and HNPCC families is numerically small and occurs earlier in life than the sporadic form(s) of the disease. For the time being we neglect their real but numerically small contribution to total colon cancer mortality.

Some 80% of colorectal adenomas in FAPC individuals have been found to lack an operative APC allele. It appears, therefore, that sporadic colon cancers have a common initiation pathway, loss of the two inherited operative alleles of the tumor suppressor gene APC (Powell, S. et al., 1992. *Nature.* 359:235–237).

It is also tempting to assume that the genetic change(s) needed in the promotion of a sporadic colon adenoma cell to a carcinoma cell would be the same for all individuals, but this assumption is without any evidentiary support and unnecessary for the analyses attempted below.

Assumption of a Single Subpopulation at Risk

These points being noted, we initially treat the colon mortality data as if there were one and only one pathway to colon cancer. If there are multiple pathways to sporadic cancer, our derivations of parameters such as the number of mutations required in initiation and promotion, their rates and the growth rate of adenomas are, perforce, a weighted average among the multiple pathways.

B. The Sizes of Subpopulations at Risk.

1. Primary versus Secondary Risk Factors

Here the term "primary risk" requires careful definition. We imagine that there are persons who by virtue of their genetic inheritance and environmental experience are at risk of death by sporadic colon cancer. It is possible that the entire population has the same genetic risk but not the same environmental experience. Conversely, it is possible that a common environmental experience is shared by all persons only a fraction of whom carry an inherited risk factor. The key postulate is that persons who do not inherit and experience these primary risk factors cannot develop colon cancer in a full lifespan of up to, say, 125 years. Primary genetic and environmental risk factors for sporadic colon cancer have not yet been identified and are, therefore, hypothetical (The primary genetic risk factors for two forms of familial colon cancer, FAPC and Lynch syndrome (HNPCC), are an inactive allele of the APC gene or of a mismatch repair gene respectively) (Kinzler, K. et al., 1991. *Science.* 253:661–5; Leach, F. et al., 1993. *Cell.* 75:1215–25).

Within subpopulations at primary risk, variations in mutation rates and cell kinetic rates are to be expected. When an inherited condition or environmental experience lowers the expected age of death relative to all persons at primary risk, we define it as a secondary risk factor. For instance, persons with mutation rates only twofold higher than average would be expected to develop cancers much earlier in life than persons with average mutation rates within the subpopulation with the same primary risk factors (Herrero-Jimenez P. et al., 1998. *Mut. Res.* 400:553–787). Inherited or environmental factors affecting mutation rates or adenomatous growth rate would, by this definition, be secondary risk factors.

2. Algebraic Approach to Definition of Primary Risk Fraction

We are seeking an algebraic way to express the relationship between the age-specific colon cancer mortality for any birth year cohort, OBS(h,t), and the primary and secondary, inherited and environmental factors which would be expected to influence it.

We define the population fraction at primary risk within a birth year cohort as F(h,t) where 'h' is the historical birth year and 't' is age (The calculation of this function and its historical changes is an important goal of our analytic effort.). The interaction of inherited and environmental primary risk factors is represented as:

$$F(h,t) = F(h,t)_{genetic} \times F(h,t)_{environmental} \text{ (see FIG. 14)} \quad \text{Equation 11}$$

We assume that there is little historical variation in the fraction of the population inheriting primary genetic risk factors, i.e., F(h,t)genetic=G is a constant. Thus, any real change in F(h,t) with 'h' would be ascribed to historical changes in the environmental primary risk factor, F(h,t) environmental. Environmental risk factors for some cancers have obvious and well recorded historical variations, e.g., cigarette smoking and lung cancer (Harris, J., 1983. *JNCI.* 71:474–478) (We believe, but leave for the future formal argument, that cigarette smoking is a primary environmental risk factor.).

Since historical changes in environmental factors would rarely reach all of the population simultaneously, primary environmental factors can vary significantly within the lifetimes of some birth year cohorts, e.g., the cohorts for whom manufactured cigarettes were not available until middle age. At this stage of model development, however, we still treat F(h,t) as invariant within a birthyear cohort in the case of colon cancer, so that:

$$F(h,t) \, F_h = G \times E_h \quad \text{Equation 12}$$

The idea of a fraction of the population with both inherited and environmental risk factors for colon cancer is logically straightforward. That fraction is represented as $G \cdot E_h$. But it follows that there also exist three other distinct subpopulations: those that have neither risk factor, $(1-G)(1-E_h)$, those that have the environmental but not the inherited risk, $(1-G) E_h$, and those that have the inherited but not the environmental risk, $G(1-E_h)$. This point is illustrated in a Venn diagram, FIG. 14. Each of these subfractions has potentially different age-specific death rates and this complication is now addressed.

3. Definition and Summation of Causes of Mortality.

We hold it to be self-evident that the total number of deaths of persons within an age interval in any historical year is the sum of the number of deaths from all possible causes. Thus, we have defined the total recorded mortality rate, TOT(h,t), as the sum of the rate of colon cancer deaths, OBS(h,t), the rate of deaths from connected causes sharing the same primary genetic and/or environmental risk factors as colon cancer, CON(h,t), and the rate of deaths from causes independent of the primary genetic or environmental causes of colon cancer, IND(h,t) (Herrero-Jimenez P. et al., 1998. *Mut. Res.* 400:553–787). We have represented this concept as:

$$TOT(h,t) = OBS(h,t) + CON(h,t) + IND(h,t) \quad \text{Equation 13}$$

The historical record defines estimates of TOT(h,t) and OBS(h,t) whereas the values of CON(h,t) and IND(h,t) are unknown.

Related to this statement is the recognition that for each of these categories of mortality there are related age-dependent probabilities. These are not simply equal to the recorded mortality fractions, a misimpression unintentionally conveyed in Herrero-Jimenez et al. (1998. *Mut. Res.* 400:553–578). Rather, these probabilities are abstract, age-dependent functions which we here more carefully define:

$P_{OBS}(h,t)$=probability that a person born in year 'h' with both primary genetic and environmental risk of colon cancer would die of colon cancer at age 't' given no treatment and no competing forms of death (population at risk: $G \cdot E_h$, FIG. 14). Unreported colon cancer deaths are included in this category.

Figure 14:
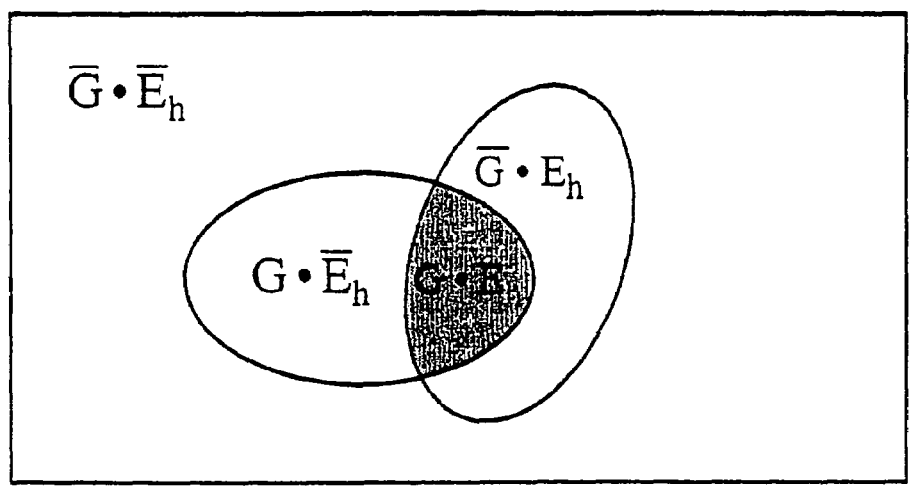
FIG. 14 is a Venn diagram representation of population at risk, F(h,t), as the intersection of the population at genetic primary risk (G) and the population at environmental primary risk ($E_h$).

$P_{CON}(h,t)$=probability that a person born in year 'h' with either primary genetic and/or environmental risk of colon cancer would die of any disease other than colon cancer connected to either or both of these risks at age 't', given no treatment and no competing independent forms of death (populations at risk: $\overline{G} \cdot E_h$, $G \cdot E_h$, $\overline{G} \cdot E_h$. FIG. 14).

$P_{IND}(h,t)$=probability that a person born in year 'h' with neither a primary genetic nor environmental risk of colon cancer would die of any other cause at age 't' (all populations at risk: FIG. 14).

In particular it should be noted that OBS*(h,t) represents the observed recorded colon cancer mortality rate for individuals born in year 'h' who were still alive at age 't' in an abstract world without therapeutic treatment. $P_{OBS}(h,t)$ is the expected colon cancer mortality rate for an individual belonging to the group $F_h$ who is still alive at age 't', also given no medical intervention. OBS*(h,t) will suffer from errors in reporting and diagnosis not accounted by our use of R(h,t). But $P_{OBS}(h,t)$, the derived mortality probability for persons in the subpopulation $G \cdot E_h$ represents all colon cancer deaths whether they are diagnosed and/or reported accurately or not in an abstract world where S(h,t)=0.

The term for the actual probability of death from colon cancer for a person at risk of birth year cohort h and age t would be the probability of dying of colon cancer in the absence of treatment, $P_{OBS}(h,t)$, multiplied by the probability that treatment has not been successful (1–S(h,t)). Similar arguments can be introduced for the connected and independent forms of mortality so that the probability of not surviving a 'connected' disease would be $(1-S_{CON}(h,t))$ and of an 'independent' form of death, $(1-S_{IND}(h,t))$.

4. Probability of Being Alive at Age t, $p_{NOT}(h,t)$.

We assume that a person at primary risk of colon cancer can die from colon cancer, a 'connected' disease caused by either the inherited and/or environmental risk factors, or a cause independent of the primary risk factors for colon cancer. This permits us to write an explicit statement for the probability, $P_{NOT}(h,t)$, that a person within the risk group $F_h$ has not yet died from any cause at any age between birth and age 't'.

$$P_{NOT}(h, t) = \quad\quad\quad \text{Equation 14}$$
$$e^{-\int_0^t [P_{OBS}(h,t)(1-S(h,t))+P_{CON}(h,t)(1-S_{CON}(h,t))+P_{IND}(h,t)(1-S_{IND}(h,t))]dt}$$

This expression is important because in considering the probability of death by colon cancer at age 't', one required physical condition is that the individual not be already dead. In the terminology of probability and analysis, we are writing equations for the conditional probability of colon cancer given the fact that the individual is not dead. In considering the diminution of the subpopulation $F_h = G \cdot E_h$, we are using a probability model of sampling without replacement.

5. Observed Colon Cancer Mortality Rate at Age t, OBS(h, t).

In Herrero-Jimenez et al. (1998. *Mut. Res.* 400:553–787) we derived an equation relating the observed mortality rate, OBS(h,t) to the expected mortality rate POBS(h,t). Our model accounted for the fact that there could be forms of death other than colon cancer which depend on either the inherited or environmental risk factors for colon cancer. The sum of all deaths by these possibilities within the group at risk for colon cancer was represented as simply CON(h,t) in a previous stage of model development (Herrero-Jimenez P. et al., 1998. *Mut. Res.* 400:553–787).

But amending our previous model, we have had to make two changes. The first is to include unreported colon cancer deaths in the term OBS*(h,t) rather than CON(h,t) by virtue of the use of R(h,t). The second was to differentiate between the diseases related to either but not both of the inherited or the environmental risk factors. To do this we introduce the term CON1(h,t) to account for the former and CON2(h,t) for the latter. We illustrate these risk factors using the population descriptors from FIG. 14 in Table 3.

TABLE 3

| Forms of death for which designated subpopulations are at risk.= | | | |
|---|---|---|---|
| $GE_h$ | $\bar{G}E_h$ | $G\bar{E}_h$ | $\bar{G}\bar{E}_h$ |
| OBS | | | |
| CON | CON1* | CON2* | |
| IND | IND | IND | IND |

*All forms of death in either CON1 or CON2 are included in the entire set of connected forms of death, CON.

Amended to better account for the effects of survival, S(h,t), underreporting error, R(h,t), and the four distinct populations introduced above (FIG. 14), the complete equation for OBS(h,t) may be written as follows:

$$OBS(h, t) = [B_h \cdot (G \cdot E_h) \cdot (1 - S(h, t)) \cdot R(h, t) \cdot P_{OBS}(h, t) \cdot \quad \text{equation 15}$$
$$P_{NOT}(h, t)] \div [B_h \cdot G \cdot E_h \cdot P_{NOT}(h, t) + (1 - G) \cdot E_h \cdot$$
$$e^{-\int_0^t [P_{CON1}(h,t)(1-S_{CON1}(h,t))+P_{IND}(h,t)(1-S_{IND}(h,t))]dt} +$$
$$G \cdot (1 - E_h) \cdot$$
$$e^{-\int_0^t [P_{CON2}(h,t)(1-S_{CON2}(h,t))+P_{IND}(h,t)(1-S_{IND}(h,t))]dt} +$$
$$(1 - G) \cdot (1 - E_h) \cdot e^{-\int_0^t P_{IND}(h,t)(1-S_{IND}(h,t))dt}]$$

OBS(h,t) is simply the number of persons within a birth cohort 'h' who are recorded as dying of colon cancer at age 't' divided by the number of all persons in the cohort still alive at that age.

The numerator, the number of deaths from colon cancer at age 't', is the product of the number of persons in the cohort at birth, $B_h$, the fraction at primary risk, $(G \times E_h)$, the fraction of individuals with colon cancer that do not survive, (1–S (h,t)), the estimated fraction of colon cancer deaths accurately recorded, R(h,t), the fraction expected to die of colon cancer in the absence of treatment, $P_{OBS}(h,t)$, and the fraction of $(G \times E_h)$ not already dead from any cause, $P_{NOT}(h,t)$.

The denominator, the number of persons still alive at age 't', is the product of the number of persons in the cohort at birth, $B_h$, and the sum of the fractions of all subpopulations still alive, whether at risk of colon cancer or not.

Since the terms for number of persons born to a cohort, $B_h$, and the term accounting for survival from causes unrelated to colon cancer risk factors, $e^{-\int P_{IND}(h,t)(1-S_{IND}(h,t))dt}$, are present as factors in the numerator and all terms of the denominator, they cancel out. By next dividing the numerator and denominator by $e^{-\int [P_{OBS}(h,t)(1-S(h,t))+P_{CON}(h,t)(1-S_{CON}(h,t))]dt}$, we convert this equation into a more manageable form:

$$OBS(h, t) = [(G \cdot E_h) \cdot (1 - S(h, t)) \cdot R(h, t) \cdot P_{OBS}(h, t)] \div \Big[G \cdot E_h + (1 - G) \cdot E_h \cdot$$

$$e^{\int_0^t [P_{OBS}(h,t)(1-S(h,t)) + P_{CON}(h,t)(1-S_{CON}(h,t)) - P_{CON1}(h,t)(1-S_{CON1}(h,t))]dt} + G \cdot$$

$$(1 - E_h) \cdot$$

$$e^{\int_0^t [P_{OBS}(h,t)(1-S(h,t)) + P_{CON}(h,t)(1-S_{CON}(h,t)) - P_{CON2}(h,t)(1-S_{CON2}(h,t))]dt} + (1 -$$

$$G) \cdot (1 - E_h) \cdot e^{\int_0^t [P_{OBS}(h,t)(1-S(h,t)) + P_{CON}(h,t)(1-S_{CON}(h,t))]dt} \Big]$$

equation 16

The algebraic elimination of the term for the probability of independent forms of death is extremely important since there is no satisfactory way of determining its value from public mortality records.

However, terms for deaths from "connected" diseases caused by the primary genetic and/or environmental colon cancer risk factors are similarly undefined in the public health record. To move beyond this clear absence of data we resort to our first, and possibly worst, algebraic approximation.

6. Accounting for Deaths by Causes Connected to Primary Risks. The Function $f_h$.

We introduce a new term, f(h,t), the ratio of colon cancer deaths to all deaths actually caused by either the inherited or environmental risk factors for colon cancer or both. We clearly don't know what the "connected" diseases are and therefore have no way of knowing what $P_{CON}(h,t)$, $P_{CON1}(h,t)$, $P_{CON2}(h,t)$, $S_{CON}(h,t)$, $S_{CON1}(h,t)$ or $S_{CON2}(h,t)$ might be. Therefore we are forced to assume pro tempore that this fraction, f(h,t), is constant for all ages within a birth year cohort but may vary among birth year cohorts. We may imagine that CON1 and CON2 include other forms of cancer and that these might therefore have an age dependence and survival probability similar to that of colon cancer. But they might include some portion of cardiovascular deaths due to unknown but shared environmental risk factors. In balance, we think this approximation is not grossly improper: the relative age dependence of colon cancer mortality is not greatly different from the major causes of human mortality, vascular disease and other major cancers.

Equation 17 defines the approximation using f(h,t) in the context of Equation 16:

$$(1 - G \cdot E_h) \cdot e^{\frac{1}{f(h,t)} \int_0^t P_{OBS}(h,t)(1-S(h,t))dt} \approx$$

$$\begin{bmatrix} (1 - G) \cdot E_h \cdot e^{\int_0^t [P_{OBS}(h,t)(1-S(h,t)) + P_{CON}(h,t)(1-S_{CON}(h,t)) - P_{CON1}(h,t)(1-S_{CON1}(h,t))]dt} + \\ G \cdot (1 - E_h) \cdot e^{\int_0^t [P_{OBS}(h,t)(1-S(h,t)) + P_{CON}(h,t)(1-S_{CON}(h,t)) - P_{CON2}(h,t)(1-S_{CON2}(h,t))]dt} + \\ (1 - G) \cdot (1 - E_h) \cdot e^{\int_0^t [P_{OBS}(h,t)(1-S(h,t)) + P_{CON}(h,t)(1-S_{CON}(h,t))]dt} \end{bmatrix}$$

equation 17

The approximation of Equation 17 distributes the effects of differential death rates among the three populations not at risk for colon cancer. As with $E_h$, we recognize that f(h,t) may vary within the lifetimes of the birth year cohorts analyzed. But for the time being we must be satisfied with treating it as a constant weighted average for each cohort, such that f(h,t)=f.

It is helpful to recall that the sum of all four subpopulation fractions is equal to one:

$$[(1-G) \times E_h] + [G \times (1-E_h)] + [(1-G) \times (1-E_h)] =$$
$$1 - (G-E_h) = (1-F_h)$$

Equation 18

Combining Equations 16, 17 and 18, we create the relatively simple expression:

$$OBS(h, t) = \frac{F_h \cdot (1 - S(h, t)) \cdot R(h, t) \cdot P_{OBS}(h, t)}{F_h + (1 - F_h) \cdot e^{\frac{1}{f_h} \int_0^t P_{OBS}(h,t)(1-S(h,t))dt}}$$

Equation 19 for which all values are known save for $F_h$, $f_h$ and $P_{OBS}(h,t)$ shown in bold face.

7. Explicit Terms for Primary Risk Factors, $F_h$ and $f_h$, for a Given Number of Initiation Mutations, 'n'.

In our previous effort $F_h$ and $f_h$ were estimated using a maximum likelihood method and the general equation derived therein for OBS(h,t) (Herrero-Jimenez P. et al., 1998. *Mut. Res.* 400:553–787). This obliged us to estimate $F_h$ and $f_h$ using an algebraic formula which included three additional unknown terms for mutation and cell kinetic rates. We were unsatisfied with this computational condition and thus sought a strategy to explicitly calculate the unknown parameters. We thus sought to derive explicit terms for $F_h$ and $f_h$ for any number of initiation mutations, 'n' (These two terms are inherently independent of the number of promotion mutations, 'm'.).

Our first tactic was to introduce a simpler function for $P_{OBS}(h,t)$. This function followed the original logic of Nordling (Nordling, C., 1953. *Brit. J. Cancer.* 7:68–72) who noted that the age dependence of phenomena requiring n mutations in the same cell in a cell population of constant size would rise as a function of age to the power of (n−1):

Nordling $P_{OBS}(h,t) = \kappa_h t^{n-1}$

Equation 20

Here, $\kappa_h$ is a constant proportional to the product of the 'n' mutational rates and the number of cells at risk. It is, in fact, the rate of initiation, a fact we shall use in deriving estimates of initiation mutation rates. We modified this model by including a time delay, $\Delta_h$, the average latency time between initiation of a normal cell and the promotion of any adenoma cell into a malignant form. The modified model becomes:

$$\text{Modified Nordling } POBS(h,t) = \kappa_h \, (t-\Delta_h)n-1(t>\Delta_h) \quad \text{Equation 21}$$

Substituting Equation 21 into Equation 19, we notice that for a given value of 'n', there are four unknown parameters: $\kappa_h$, $\Delta_h$, $F_h$, and $f_h$.

$$OBS(h,t) = \frac{F_h \cdot (1-S(h,t)) \cdot R(h,t) \cdot \kappa_h \cdot (t-\Delta_h)^{n-1}}{F_h + (1-F_h) \cdot e^{\frac{1}{f_h} \int_0^t \kappa_h \cdot (t-\Delta_h)^{n-1}(1-S(h,t))dt}} \quad (t>\Delta_h) \quad \text{Equation 22}$$

To explicitly solve for any or all of these four unknown terms, we needed to find four independent equations. This has, in fact, now been accomplished.

8. Parameters Determined by Inspection: ($F_h \kappa_h$) and $\Delta_h$.

$\Delta_h$ and ($F_h \kappa_h$) were determined for each birth year cohort by inspection from the mortality data corrected for survival and under-reporting, OBS*(h,t), as recorded in FIGS. 9A, 9B, 10A and 10B. To accomplish these estimations, we approximated the OBS*(h,t) for values up to the age tmax when OBS*(h,t) reaches a maximum. The equation is suitable for any number of initiation mutations, n.

$$OBS^*(h,t) \approx F_h P_{OBS}(h,t) = F_h \kappa_h \, (t-\Delta_h)^{n-1}(t_{max}>t>\Delta_h) \quad \text{Equation 23}$$

Figure 15:
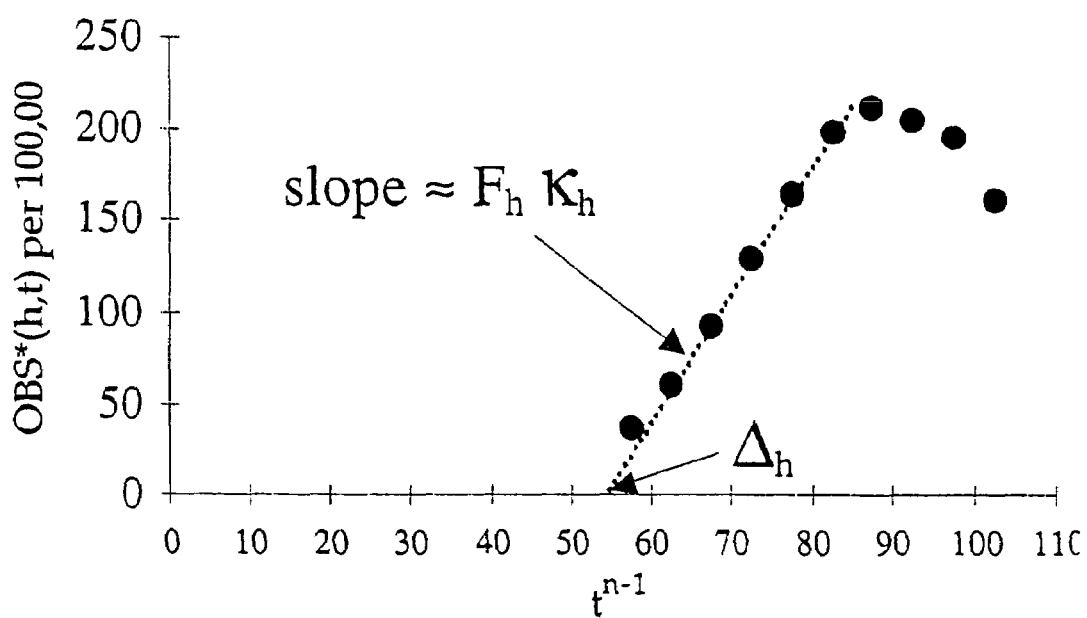
FIG. 15 is a graph estimating parameters ($F_h$, $\kappa_h$) and $\Delta_h$ for the n=2 model in EAM 1870s.

This formulation is essentially that first suggested by Nordling (1) who did not have data for extreme old age and thus could not have recognized the maximum. For example, in the case of n=2, OBS*(h,t) would have a value of zero up to t=$\Delta_h$ and then rise linearly with slope ($F_h \kappa_h$). The x-intercept of the line is $\Delta_h$. As OBS*(h,t) approaches its maximum at $t_{max}$, the approximation fails. FIG. 15 shows the calculations for European-American males born in the 1870s.

$\Delta_h$ and ($F_h$, $\kappa_h$) can be similarly determined by inspection for all other values of n by simply plotting OBS*(h,t) versus tn−1. For the general model with 'n' initiation mutations, $\Delta_h$ is simply the x-intercept of the linear portion of the plot of OBS*(h,t) versus tn−1. $\kappa_h$ and $F_h$ however cannot at this stage be explicitly determined; their product, ($F_h$, $\kappa_h$), has been explicitly defined for $t_{max}>t>\Delta_h$:

$$(F_h \kappa_h) \approx \text{slope of linear portion of OBS*(h,t) vs.} t^{n-1} \quad \text{Equation 24}$$

9. The Use of the Area Under $OBS^R(h,t)$ to Define $F_h$ in Terms of $f_h$.

Defining the two unknowns, $F_h$ and $f_h$ required two additional independent equations. The first was supplied by the integral of the equation $OBS^R(h,t)$ vs. t from t=0 to infinity, where $OBS^R(h,t)$ represents the expected mortality rate if all deaths from colon cancer had been reported.

$$OBS^R(h,t) = OBS(h,t) \div R(h,t) \quad \text{Equation 25}$$

Figure 16:
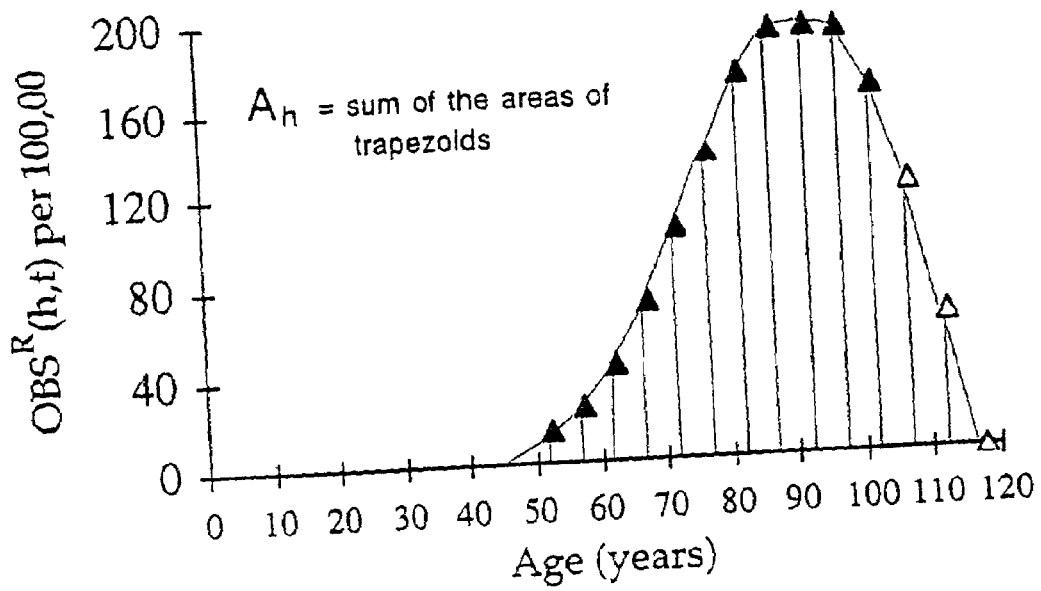
FIG. 16 is a graph demonstrating the estimation of the integral of $OBS^R(h,t)=OBS(h,t)\div R(h,t)$. Open symbols represent extrapolations of the data used for the approximation.

We used the function $OBS^R(h,t)$ as it is more easily integrated. This integral must be approximately equal to the area observed for the data of $OBS^R(h,t)$ vs. t as illustrated in FIG. 16.

We intuitively expected that this area, $A_h$, must be a function of the population at risk of contracting colon cancer, $F_h$, and the fraction of the population at risk which would actually die from colon cancer, $f_h$ as opposed to forms of death sharing inherited or environmental risk factors or both with colon cancer. This area would be independent of factors which would affect when deaths are expected, such as survival rates, mutation rates and cell kinetics rates, as well as the number of events required for initiation or promotion.

The algebraic relationship among the area under $OBS^R$ (h,t) and $F_h$ and $f_h$ is shown as Equation 26. The derivation of this equation via the explicit integration of Equation 25 is provided in the appendix. The simplicity of this result was astonishing. More practically, it provided a definition of $F_h$ as an explicit function of $f_h$ and the observed parameter $A_h$ for any cohorts studied and, for that matter, any form of cancer or other mortal disease.

$$A_h = \int_0^\infty OBS^R(h,t)\,dt = -f_h \cdot \ln(1-F_h) \quad \text{Equation 26}$$

Even with this useful observation we had not yet explicitly determined any of the unknown terms $\kappa_h$, $F_h$ or $f_h$. Equations 24 and 26 alone did not independently define all three terms. We had three unknowns and only two independent equations.

10. The Use of the Maximum Value of OBS*(h,t) to Define $F_h$ in Terms of $\kappa_h$ and $f_h$.

For our last necessary equation, we took advantage of the feature that the mortality function OBS*(h,t) reaches a clear maximum in old age as shown in FIGS. 9A, 9B, 10A and 10B. The derivative of a continuous function equals zero at a maximum. By taking the derivative of OBS*(h,t) and setting it equal to zero at t=$t_{max}$, the age at which OBS*(h,t) is a maximum, we solved for $F_h$ in terms of the other unknowns for any value of n (see appendix for derivation). This general solution is shown as Equation 27.

$$F_h = \frac{(n-1) \cdot f_h - (1-S(h,t_{max}))\kappa_h(t_{max}-\Delta_h)^n}{(n-1) \cdot f_h \cdot \left(1 - e^{-\frac{1}{f_h}\int_0^{t_{max}}(1-S(h,t))\kappa_h(t-\Delta_h)^{n-1}dt}\right) - (1-S(h,t_{max}))\kappa_h(t_{max}-\Delta_h)^n} \quad \text{equation 27}$$

Thus we had derived four independent equations using three separate features of the mortality curves, plus the direct observation of $\Delta_h$:

1. the slope of the (n−1)th root of OBS*(h,t) for Equation 20,
2. the x-intercept of the (n−1)th root OBS*(h,t), direct estimation of $\Delta h$,
3. the area under $OBS^R(h,t)$ for Equation 22 and
4. the maximum of OBS*(h,t)) for Equation 23.

Together these equations allowed us to explicitly determine two desired population risk parameters, $F_h$ and $f_h$ for any birth cohort for which these four features were defined by the data. We also solved for the physiological parameter $\kappa_h$ which we use below to estimate initiation mutation rates for any value of n. We did not use maximum likelihood methods to determine values for these primary risk factors. Rather, we solved for them explicitly after making use of the approximation of Equation 17 defining $f_h$.

This tactic allowed us to estimate the historical variable $F_h$. That should let us chart the health effects of environmental changes in populations. It is also the minimum value for G or $E_h$ for any birth year cohort since when $E_h$=1, G=$F_h$ and vice versa. Both of these properties are of clear value in exploring the genetic and environmental interactions which lead to colon cancer.

C. Explicit Terms for Secondary Risk Parameters: Initiation and Promotion Mutation Rates, and Adenomatous Growth Rates for a Given n and m.

Having found an explicit way to calculate the fraction of a birth year cohort at risk of colon cancer, we were ready to use algebraic models of tumor initiation and promotion to calculate the values of the mutation and cell kinetics rate which are posited to determine the age-specific mortality rates.

1. The product of initiation mutation rates, $(r_i\, r_j\, r_k\, \ldots\, r_n)$.

Our model for initiation with n>1 required events is based on that of Armitage and Doll (1954. *Brit. J. Cancer.* 8:1–12) in which 'n' events in any cell would create the first cell of an adenoma. We have, however, extended the physiological model to account for cell turnover in normal tissues and the organization of tissues as turnover units of constant and equal size containing Na total cells at age 'a'.

The Na total cells comprise terminal cells, transition cells and stem cells. It may be that initiated terminal cells have zero probability of forming a tumor and, if this were the case, the number of cells at risk would be reduced by ½. For the time being, we model all cells as being at risk as there are several months between terminal division and programmed death in a human colon terminal cell and a shorter period, about forty days, between divisions in a human colon adenoma cell. The stem cell and each transition cell undergo t divisions and no deaths per year. The terminal cells each "die" t times per year and do not divide. The value of t was determined to be approximately 3.

We have argued (Herrero-Jimenez P. et al., 1998. *Mut. Res.* 400:553–787) that the most probable pathway of accumulating n>1 mutations in tumor initiation is by the acquisition of all but one of the 'n' mutations in the stem cell. The stem cell then repopulates its respective turnover unit with cells carrying the (n−1) mutations, such that the nth mutation could now occur in any of these cells.

We represent the rates of the required initiation mutations as $r_i\, r_j\, r_k\, \ldots\, r_n$. The expression describing the number of newly initiated cells in year 'a' is simply:

$$\text{Initiated cells in year 'a'} = n\tau^n (\mathrm{i}r_j r_k \ldots r_n) N_a a^{n-1} \quad \text{Equation 28}$$

for the case in which the order of the n mutations is inconsequential. Expressions may also be derived for models in which a specific order of some or all initiation mutations are required.

2. The difference in division and death rates in adenomas, $(\alpha-\beta)$, and the stochastic extinction of newly initiated cells.

As recognized and algebraically treated by Moolgavkar, S. et al. (1990. *Carcinogenesis.* 11: 1271–1278), each initiated cell could die before it divides. Even small colonies have a high probability that all cells will die; only a few would be expected to survive as adenomas when the probability of cell division is only marginally greater than the probability of cell death. Given a cell division rate of a cell divisions per year and a death rate, b, for an initiated cell, the probability of non-extinction or survival is $(\alpha-\beta)/\alpha$ (Moolgavkar, S. et al., 1990. *Carcinogenesis.* 11:1271–1278). Thus the number of newly arising and surviving adenomas in year 'a' would be:

$$\text{Surviving Adenomas } (a) = \frac{(\alpha-\beta)}{\alpha} n \tau^n (r_i r_j r_k \ldots r_n) N_a a^{n-1} \quad \text{Equation 29}$$

for the case in which the order of mutations is inconsequential. In the model for promotion used below, all surviving adenomas have the property of inexorably giving rise to a lethal carcinoma via net growth and mutation. Note that the values of $\alpha$ and $\beta$ have been determined to be approximately 9 divisions or "deaths" per year, respectively (Herrero-Jimenez P. et al., 1998. *Mut. Res.* 400:553–787). The unknown terms for the rate of initiation are the product of the rates of the n initiation mutations $(r_i\, r_j\, r_k\, \ldots\, r_n)$ and the small difference between division and death rates in colon adenomas, $(\alpha-\beta)$.

3. Use of the calculated value of $\kappa_h$ to define an independent equation with two unknown terms: $(r_i\, r_j\, r_k\, \ldots\, r_n)$ and $(\alpha-\beta)$.

The combination of the data of OBS*(h,t) and Equations 20, 22 and 23 allowed explicit determination of the unknown parameter $\kappa_h$ for any cohort studied. $\kappa_h$ is Nordling's annual rate of initiation per person modified to include Moolgavkar's necessary term for surviving stochastic extinction. Here we write it for the case after Na has reached a maximum, $N_{max}$, in young adults (Herrero-Jimenez P. et al., 1998. *Mut. Res.* 400:553–787).

$$\kappa_h = \frac{\alpha-\beta}{\alpha} n \tau^n (r_i r_j r_k \ldots r_n) N_{\max} \quad \text{Equation 30}$$

Cell division and "death" rates can be acquired from actual tissue samples: t in normal tissue, and a and b in adenomas (Herrero-Jimenez P. et al., 1998. *Mut. Res.* 400:553–787). However, a value for the growth rate of an adenoma, $(\alpha-\beta)$, is small and we cannot get accurate independent estimates for the division and deaths rates in vivo to properly estimate this difference from tissue samples.

All terms in Equation 30 are known except $(r_i\, r_j\, r_k\, \ldots\, r_n)$ and $(\alpha-\beta)$, but we can make use of an interesting property of OBS*(h,t) to explicitly define $(\alpha-\beta)$ and then estimate the value of $(r_i\, r_j\, r_k\, \ldots\, r_n)$. For this, we must first extend Nordling's model for the expected mortality from the OBServed disease, $P_{OBS}(h,t)$, to account for the growth rate of an adenoma.

4. The expected mortality rate from the OBServed disease, $P_{OBS}(h,t)$, within the group at risk, $F_h$.

In our three-stage carcinogenesis model, we assumed that the third stage, progression, occurs rapidly and can be effectively modeled as occurring in zero years. Therefore, the expected mortality from the OBServed disease simply equals the probability of initiation at age 'a' (Equation 29) times the probability of promotion occurring at a later age 't'.

Our model for the second stage of the three-stage carcinogenesis model, promotion, is again based on that of Armitage and Doll (1954. *Brit. J. Cancer.* 8:1–12) in which 'm' particular events in any cell of the adenoma would create the first cell of a carcinoma. We first considered the simplest case for which a single genetic event could turn an adenoma cell into a carcinoma cell. Using the Poisson approximation, the probability of at least one cell undergoing promotion at age 't' in an adenoma that was initiated at age 'a' is:

$$\frac{d\left(1 - e^{\left(-r_A \cdot \left(\frac{\alpha}{\alpha-\beta}\right)^2 \cdot \frac{(2^{(\alpha-\beta)(t-a)}-1)}{\ln 2} \cdot \frac{\alpha_c-\beta_c}{\alpha_c}\right)}\right)}{d(t-a)}$$ Equation 31

The exponential represents the expected number of cells in the adenoma to have undergone promotion and survived stochastic extinction, (t−a) years after initiation. Here, $r_A$ represents the promotion mutation rate per cell division, and $(\alpha_c-\beta_c)\div\alpha_c$ represents the probability of a promoted cell colony surviving stochastic extinction, given cell division and death rates per year of $\alpha c$ and $\beta c$ respectively. The remaining terms in Equation 31 describe the total number of cell divisions, or chances for promotion, that have occurred within the adenoma. We have extended our previous approximation (Herrero-Jimenez P. et al., 1998. *Mut. Res.* 400:553–787) for the total number of cell divisions to more accurately account for cell divisions from cells that have died (see Appendix for derivation). Combining the probability of initiation from Equation 29 with the probability of promotion from Equation 31, we get that the expected mortality from the observed disease within the group at risk is (m=1 case illustrated):

$$P_{OBS}(h, t) = n\,\tau^n (r_i r_j r_k \ldots r_n)\frac{\alpha-\beta}{\alpha}\int_0^t aN_a \frac{d\left(1 - e^{-(-r_A \cdot (\frac{\alpha}{\alpha-\beta})^2 \frac{(2^{(\alpha-\beta)(t-a)}-1)}{\ln 2} \frac{\alpha_c-\beta_c}{\alpha_c})}\right)}{d(t-a)} da$$ Equation 32

Obviously, an individual could develop more than one adenoma within a lifetime, so we necessarily accounted for all possible adenomas initiated at any age between birth and 't', by integrating across all ages. We can now use OBS*(h,t) to explicitly define $(\alpha-\beta)$ and then estimate the value of $(r_i r_j r_k \ldots r_n.)$ 5. The growth rate of adenomas, $(\alpha-\beta)$.

Figure 17:
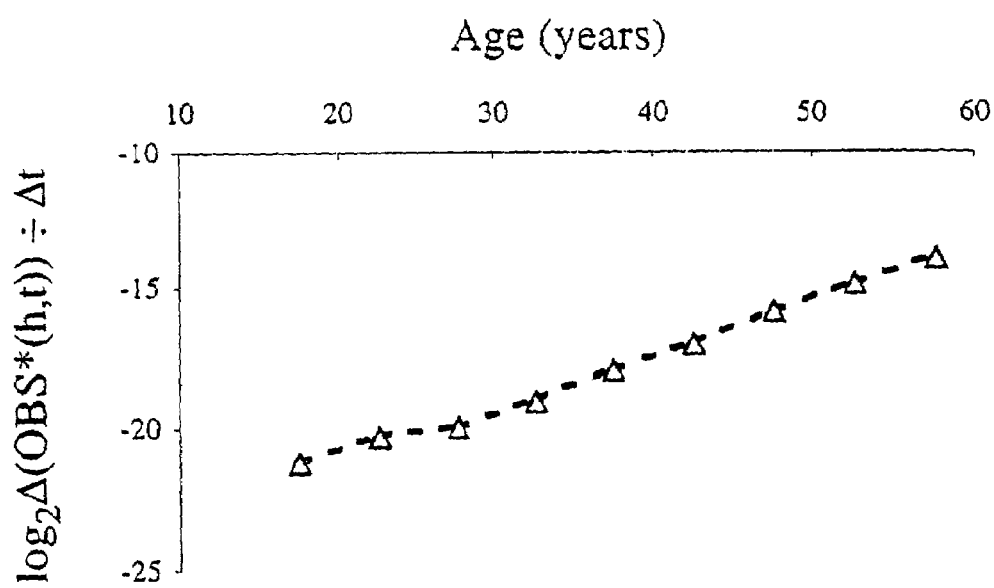
FIG. 17 is a graph demonstrating the determination of (α–β) from the slope of log 2 Δ(OBS*(h,t))÷Δt. Data used are for EAM born in the 1920s, ages 17.5 to 57.5.

Our incorporation of the concept of an intermediate colony, an adenoma, into Nordling's carcinogenesis model allowed us to write the expected mortality rate, $P_{OBS}(h,t)$, for those individuals within the group at risk, in terms of the initiation mutation rates, the promotion mutation rate, and the adenomatous growth rate. Incorporating our updated expected mortality to the estimate for OBS*(h,t) in the younger population in Equation 23, and then taking the log2 of its derivative conveniently gives a line of the form:

log2d(OBS*(h,t))÷dt=(α−β)t+constant (See Appendix)
Equation 33 from which we can easily read off the slope to get an estimate for the cell kinetic growth rate of the adenoma, $(\alpha-\beta)$. As an example, FIG. 17 shows an estimate for EAM born in the 1920s. To evaluate the derivative of OBS*(h,t) from our mortality data, we use the approximation Δ(OBS*(h,t))÷Δt d(OBS*(h,t))÷dt.

6. Explicit determination of the product of initiation mutation rates, $(r_i r_j r_k \ldots r_n)$.

The determination of the cell growth rate of an adenoma, $(\alpha-\beta)$, allowed us to calculate the product of the initiation mutation rates, $(r_i r_j r_k \ldots r_n)$ using the previously derived value of $\kappa_h$ and Equation 30. From this product, the geometric mean can be derived as $(r_i r_j r_k \ldots r_n)(1/n)$. We next make use of the approximation of the growth rate of an adenoma to determine the promotion mutation rates.

7. The average promotion mutation rates, $r_A$.

Evaluation of the average promotion mutation rate can be expressed in terms of previously defined values. The value $\Delta_h$ represented the average time between initiation and promotion. The cumulative probability of promotion in an adenoma is therefore approximately one-half, $\Delta_h$ years after its initiation. This allowed us to relate the observed delay to the average promotion mutation rate, rA, and the adenomatous growth rate, $(\alpha-\beta)$. For the case of only one necessary promotion mutation, m=1, this is:

$$\Delta_h = \frac{\log_2\left[1 + \left(r_A \cdot \left(\frac{\alpha}{\alpha-\beta}\right)^2 \cdot \frac{\alpha_c-\beta_c}{\alpha_c} \cdot \frac{1}{[\ln(2)]^2}\right)^{-1}\right]}{\alpha-\beta}$$ Equation 34

(See Appendix for derivation)

If more than one genetic event were needed to convert an adenoma cell into a carcinoma cell, m>1, we must consider additional phenomena. After the accumulation of each new promotion mutation there would arise within the adenoma a new colony of cells each containing that new promotion mutation. As in the case of a newly initiated cell, the new colony must survive stochastic extinction, such that a fully promoted cell would necessarily have undergone 'm' possible rounds of net growth and stochastic redistribution.

Each promotion event could alter either the promotion mutation rate or growth rate of the cells in this new colony. We, however, cannot deconvolute the mortality data to evaluate these rates for each of the steps of promotion independently. Still, we can relate the total delay between initiation and promotion, $\Delta_h$, to the geometrical average promotion mutation rate and the average adenomatous growth rate for those cells that made up the direct lineage between the first adenoma cell and the first cancer cell. The total expected delay between initiation and promotion, $\Delta_h$, is simply the sum of the delays between each promotion event:

$$\Delta_h = \frac{\log_2\left[1 + \left(r_A \cdot \left(\frac{\alpha}{\alpha-\beta}\right)^2 \cdot \frac{\alpha_c-\beta_c}{\alpha_c} \cdot \frac{1}{[\ln(2)]^2}\right)^{-1}\right] + (m-1)\cdot\log_2\left[1 + \left(r_A \cdot \frac{\alpha}{\alpha-\beta} \cdot \frac{1}{[\ln(2)]^2}\right)^{-1}\right]}{\alpha-\beta}$$ Equation 35

This yields us an equation for the general case of 'm' promotion mutations, assuming that the order in which the promotion mutations occur is important. Such a mutation would be expected to be an early step of promotion as it would increase the chance of an adenoma cell undergoing complete promotion within an individual's lifetime. If the order in which the 'm' mutations occurred were unimportant, the delay between initiation and promotion would then be:

$$\Delta_h = \frac{\log_2\left[1 + \left(r_A \cdot \left(\frac{\alpha}{\alpha-\beta}\right)^2 \cdot \frac{\alpha_c - \beta_c}{\alpha_c} \cdot \frac{1}{[\ln(2)]^2}\right)^{-1}\right] + \sum_{i=2}^{m} \log_2\left[1 + \left(ir_A \cdot \frac{\alpha}{\alpha-\beta} \cdot \frac{1}{[\ln(2)]^2}\right)^{-1}\right]}{\alpha - \beta}$$

Equation 36

In either case, the only parameter left unknown is the geometric average promotion mutation rate, $r_A$. Either of these equations is sufficient to evaluate this last unknown parameter, thereby completing our explicit derivation of all physiological parameters in the three-stage carcinogenesis model, $r_i$, $(\alpha-\beta)$ and $r_A$.

Results

Union of the Model with the Public Record of Colon Cancer Mortality.

A. Example of n=2 and m=1.

As a first demonstration of our algebraic representation of the three-stage carcinogenesis model, we apply the n=2, m=1 case. We chose n=2 based on the observations that loss of function of both good copies of the APC alleles were sufficient to initiate a colon adenoma (FIG. 18), and that in our previous effort (Herrero-Jimenez P. et al., 1998. *Mut Res.* 400:553–787) estimates for mutation rates were similar to mutation rates of T-cell precursor cells (Grist, S. et al., 1992. *Mut. Res.* 266:189–196). We first present m=1 as this is the simplest case.

Table 4 and FIGS. 19A, 19B, 20A and 20B summarize the results for the n=2, m=1 case, extending Herrero-Jimenez et al. (1998. *Mut. Res.* 400:553–787) by including estimates for Non-European-Americans. Initiation mutation rate $r_i$ values are reported assuming that $r_i=1/3r_j$. We base this on the observation by Grist et al. (1992. *Mut. Res.* 266:189–196) that the sum of all pathways for loss of heterozygosity of the HLA-A locus in T-cell precursors is about $6.6 \times 10^{-7}$ events per cell year, compared to a rate of $2.2 \times 10^{-7}$ for inactivation by point mutation for a single allele of the same gene.

TABLE 4

Summary of cell kinetics for colon cancer: (Mitotic time was assumed to be 90 minutes.)

| Birthyear | $F_h$ | $f_h$ | $r_i$ | $r_A$ | $\alpha - \beta$ |
|---|---|---|---|---|---|
| EAM | | | | | |
| 1840s | 0.30 | 0.11 | $4.4 \times 10^{-8}$ | $8.4 \times 10^{-8}$ | — |
| 1850s | 0.35 | 0.13 | $4.6 \times 10^{-8}$ | $8.8 \times 10^{-8}$ | — |
| 1860s | 0.38 | 0.15 | $5.6 \times 10^{-8}$ | $8.0 \times 10^{-8}$ | — |
| 1870s | 0.41 | 0.15 | $5.7 \times 10^{-8}$ | $8.2 \times 10^{-8}$ | — |
| 1880s | 0.40 | 0.21 | $5.9 \times 10^{-8}$ | $1.3 \times 10^{-7}$ | 0.19 |
| 1890s | 0.40 | 0.21 | $6.7 \times 10^{-8}$ | $8.6 \times 10^{-8}$ | 0.20 |
| 1900s | 0.39 | 0.24 | $7.0 \times 10^{-8}$ | $7.6 \times 10^{-8}$ | 0.21 |
| 1910s | 0.45 | — | $8.5 \times 10^{-8}$ | $8.1 \times 10^{-8}$ | 0.19 |
| 1920s | 0.43 | — | $7.6 \times 10^{-8}$ | $8.1 \times 10^{-8}$ | 0.21 |
| 1930s | 0.42 | — | $7.4 \times 10^{-8}$ | $8.1 \times 10^{-8}$ | 0.21 |
| EAF | | | | | |
| 1840s | 0.28 | 0.18 | $7.0 \times 10^{-8}$ | $1.6 \times 10^{-7}$ | — |
| 1850s | 0.33 | 0.18 | $7.0 \times 10^{-8}$ | $1.5 \times 10^{-7}$ | — |
| 1860s | 0.41 | 0.15 | $7.2 \times 10^{-8}$ | $1.2 \times 10^{-7}$ | — |
| 1870s | 0.39 | 0.15 | $7.3 \times 10^{-8}$ | $1.8 \times 10^{-7}$ | — |
| 1880s | 0.40 | 0.16 | $6.9 \times 10^{-8}$ | $2.5 \times 10^{-7}$ | 0.16 |
| 1890s | 0.40 | 0.17 | $7.0 \times 10^{-8}$ | $3.0 \times 10^{-7}$ | 0.16 |
| 1900s | 0.39 | 0.17 | $7.0 \times 10^{-8}$ | $2.6 \times 10^{-7}$ | 0.17 |
| 1910s | 0.39 | — | $7.2 \times 10^{-8}$ | $2.4 \times 10^{-7}$ | 0.17 |
| 1920s | 0.39 | — | $7.0 \times 10^{-8}$ | $2.6 \times 10^{-7}$ | 0.17 |
| 1930s | 0.39 | — | $7.0 \times 10^{-8}$ | $2.5 \times 10^{-7}$ | 0.17 |
| NEAM | | | | | |
| 1850s | 0.31 | 0.06 | $4.3 \times 10^{-8}$ | $5.8 \times 10^{-8}$ | — |
| 1860s | 0.35 | 0.08 | $4.3 \times 10^{-8}$ | $5.8 \times 10^{-8}$ | — |
| 1870s | 0.36 | 0.11 | $4.3 \times 10^{-8}$ | $7.1 \times 10^{-8}$ | — |
| 1880s | 0.43 | 0.13 | $4.7 \times 10^{-8}$ | $8.5 \times 10^{-8}$ | 0.19 |
| 1890s | 0.45 | 0.17 | $6.1 \times 10^{-8}$ | $7.4 \times 10^{-8}$ | 0.19 |
| 1900s | 0.43 | 0.21 | $7.0 \times 10^{-8}$ | $8.1 \times 10^{-8}$ | 0.18 |
| 1910s | 0.43 | — | $6.2 \times 10^{-8}$ | $6.8 \times 10^{-8}$ | 0.21 |
| 1920s | 0.43 | — | $6.2 \times 10^{-8}$ | $5.6 \times 10^{-8}$ | 0.23 |
| 1930s | 0.45 | — | $6.9 \times 10^{-8}$ | $8.2 \times 10^{-8}$ | 0.21 |
| NEAF | | | | | |
| 1860s | 0.41 | 0.08 | $4.8 \times 10^{-8}$ | $8.0 \times 10^{-8}$ | — |
| 1870s | 0.45 | 0.11 | $4.4 \times 10^{-8}$ | $1.5 \times 10^{-7}$ | — |
| 1880s | 0.45 | 0.13 | $4.6 \times 10^{-8}$ | $2.0 \times 10^{-7}$ | 0.17 |
| 1890s | 0.44 | 0.14 | $6.2 \times 10^{-8}$ | $2.0 \times 10^{-7}$ | 0.15 |
| 1900s | 0.45 | 0.14 | $6.4 \times 10^{-8}$ | $2.5 \times 10^{-7}$ | 0.15 |
| 1910s | 0.41 | — | $5.9 \times 10^{-8}$ | $2.6 \times 10^{-7}$ | 0.16 |
| 1920s | 0.42 | — | $5.8 \times 10^{-8}$ | $2.3 \times 10^{-7}$ | 0.17 |
| 1930s | 0.42 | — | $6.1 \times 10^{-8}$ | $1.8 \times 10^{-7}$ | 0.17 |

Comprehensive analysis of the data for birth year cohorts from 1910 onwards was not possible. Estimation of '$f_h$' was not possible for these birth year cohorts, as reasonable knowledge of how the mortality rates decreases at extreme old age is required. We were able to observe $(\alpha-\beta)$ and thereby calculate the promotion mutation rate, $r_A$, for more recent birth year cohorts. $F_h$ and $r_i$ were approximated by noting that the slope of the colon cancer rates for the later birth years did not show significant changes in their slope (FIGS. 9A, 9B, 10A and 10B), suggesting that the area under the mortality curves would be constant. If future data demonstrates that the area actually changed, this will necessarily have been due to a result of a change in f, but not in $F_h$. A change in $F_h$ would have affected both the slope and area of the age-specific colon cancer mortality rate function.

Similarly, $(\alpha-\beta)$ could not be ascertained for birth years prior to 1880 since data for the age interval 20–60 are used for this purpose and data were available to us only from the reporting year of 1930 forward. As this value appears invariant for each population cohort, other parameters were estimated assuming that the adenomatous growth rate is a constant.

B. Example of n=2, but m>1.

We were attracted to the hypothesis that m=1 because the observed value for the promotion mutation rate was similar to the rate of LOH in T-cell precursors [5, 6]. We then hypothesized that the necessary event for promotion was the loss of heterozygosity of any of an undefined set of second gatekeeper genes, such that we could define the fraction at risk by the fraction of the population heterozygous for at least one of the second gatekeeper genes.

However, this hypothesis was inconsistent with the undisputed fact that colon tumors display a very high fraction (on average 0.22) of LOH and LOI distributed over all chromosomes (Vogelstein, B. et al., 1989. *Science.* 244:207–211; Vogelstein, B. et al., 1988. *N. Engl. J. Med.*, 319:525–32; Garcia-Patiño, E. et al., 1998. *Cancer Genet. Cytogenet.* 104:119–123; Resta, N. et al., 1998. *Cancer Res.* 58:4799–4801; Uhrhammer, N. et al., 1999. *Oncol. Rep.*

6:655–658; Ragnarsson, G. et al., 1999. *Br. J. Cancer.* 79:1468–1474; Cui, H. et al., 1998. *Nat. Med.* 4:1276–1280). We therefore reconsidered the promotional events in terms of rates of LOH and LOI which would yield LOH and LOI fractions of 0.22 in colon carcinomas.

There are about 9×63=567 lineal cell divisions between a first adenoma and first carcinoma cell in colon cancer. The rate of LOH or LOI to achieve a fraction of 0.22 from events in adenomatous growth alone would be $0.22/567=3.9\times10^{-4}$ LOH or LOI events per adenoma cell division.

This estimate can be considered in terms of the geometric means of the promotional mutation rates for different values of m. Our calculations are summarized in Table 5.

TABLE 5

Calculated geometric mean of promotion mutation rates, m = 1 – 4.
Data are for European-American females born in the 1860s.
(unordered = mutations can occur in any order,
ordered = mutations must occur in one particular order)

| m | Unordered rA | Ordered rA |
|---|---|---|
| 1 | $1.2 \times 10^{-7}$ | $1.2 \times 10^{-7}$ |
| 2 | $2.5 \times 10^{-5}$ | $3.5 \times 10^{-5}$ |
| 3 | $1.4 \times 10^{-4}$ | $2.8 \times 10^{-4}$ |
| 4 | $3.3 \times 10^{-4}$ | $8.5 \times 10^{-4}$ |
| 5 | $5.4 \times 10^{-4}$ | $1.6 \times 10^{-3}$ |

For the case of ordered promotional mutations, values of m=3 and 4 yield mutation rates bracketing the LOH/LOI rate of $3.9\times10^{-4}$. For unordered promotional events, the values for m=4 and 5 bracket this value. Such calculations can be of use in considering the number of LOH plus LOI events that might be required in tumor promotion, but such considerations should not lose sight of the fact that there is no present evidence that either LOH or LOI events are required in promotion.

Discussion

Major Conclusions.

Use of the data for survival probabilities as a function of age and history have extended and confirmed our earlier interpretation based on mortality data alone: there is a true maximum in the age-specific colon cancer mortality rate for males and females in both European- and African-American subpopulations. This interpretation is essential for the development of a means to calculate the fraction at risk of colon cancer for each birth year cohort.

We have developed and used an extended Knudson-Moolgavkar model for initiation and promotion in which 'n' rare events are required for initiation and 'm' for promotion (Herrero-Jimenez P. et al., 1998. *Mut. Res.* 400:553–787). With it and the approximation of Equation 17 to account for competing forms of death sharing environmental and/or genetic risk factors with colon cancer, we have calculated birth year cohort-specific values for the fraction at primary risk, the product of initiation mutation rates, the product of promotion mutation rates, and the average growth rate of the adenomatous intermediate colony.

Since these parameters have been calculated for each birth year cohort, their historical changes may be observed. These in turn may be considered in terms of historical changes in human habits and their environment. These parameters may be compared between the two large demographic cohorts for which data are available. Similarly, the parameters for males and females may be compared.

Historical Changes in the Fraction at Risk, $F_H$.

Figure 19A:
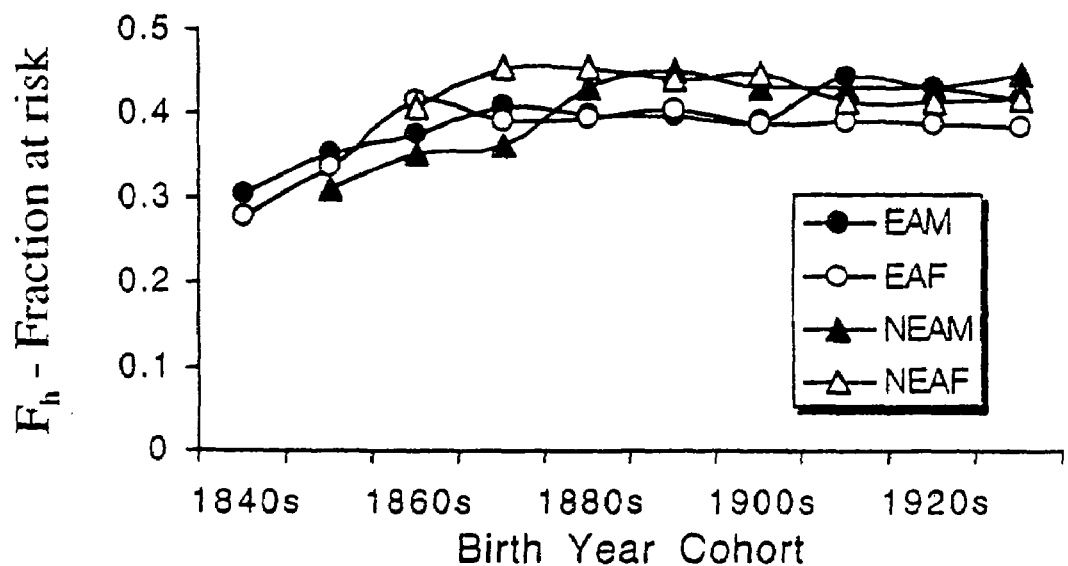
FIGS. 19A and 19B are graphs showing the fraction of EAM, EAF, NEAM and NEAF at primary risk for colon cancer, $F_h$, (FIG. 19A) and the initiation mutation rate, $r_i$ (FIG. 19B) as a function of year of birth.
Figure 19B:
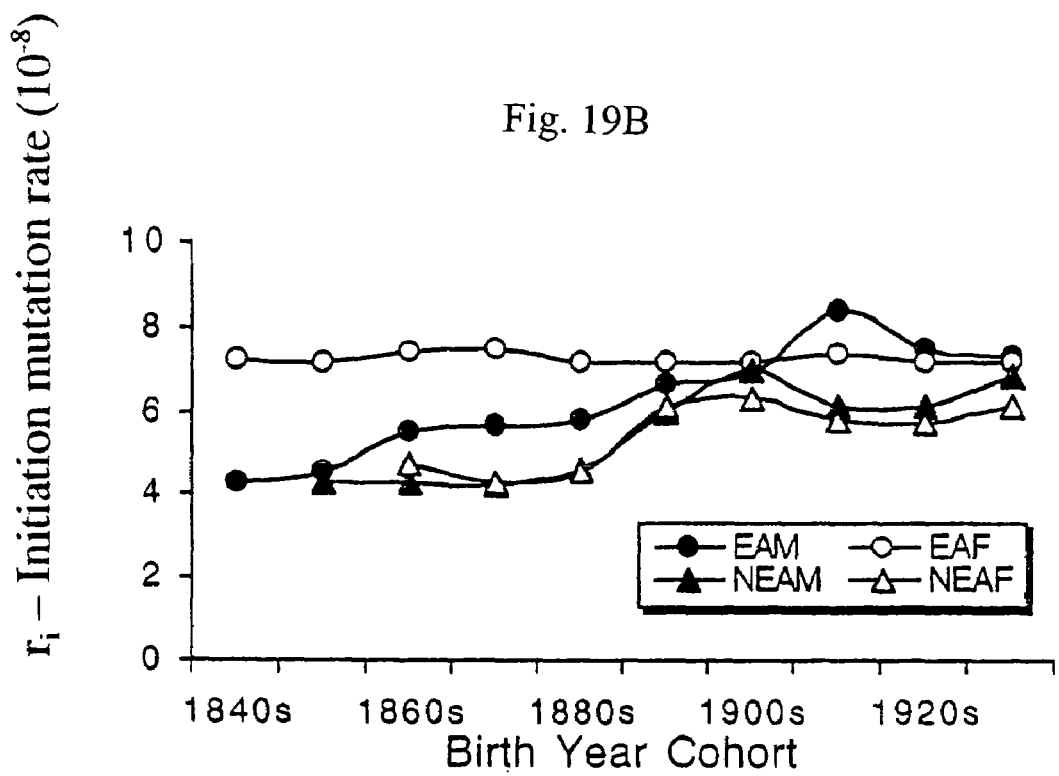

The fraction at primary risk of colon cancer has remained essentially constant for the birth year cohorts of the 1860s to the 1940s (FIGS. 19A and 19B). This is true for males and females of both European or African heritage. This fraction is about 0.4. It is possible that this fraction at risk was increasing from 0.3 for the birth cohort for the 1840s to 0.4 for the 1870s.

The constancy of this fraction during a period of marked changes in American life in nutrition, smoking habits, level of exercise, industrialization and urbanization is striking. These data suggest that none of these known environmental changes had any effect on the fraction at risk due to environmental risk factors. It might be imagined that there have been offsetting environmental changes but such arguments, absent data, violate the "law of parsimony." It should be noted that this result does not indicate that there are no environmental factors affecting age-specific colon cancer rates. Subpopulations with conditions varying significantly from the population average might have higher or lower rates depending on their circumstances.

Magnitude of the Population at Risk.

It may be surprising that the fraction at risk is as large as 40%, given that less than 5% of all deaths result from colon cancer. This result, however, emphasizes the importance and necessity of accounting for all other connected forms of death in calculating the primary risk fraction for any mortal disease.

The estimate of 0.4 represents a minimum value for the fraction at primary genetic risk. If all persons were at environmental risk, then the fraction at primary genetic risk would be 0.4.

Population Genetics of Primary Risk for Colon Cancer.

Case I: Genetic Risk is Conferred by a Dominant Mutation Non-Deleterious for Reproductive Fitness.

In this case, homozygous recessives (wild-type) would have zero genetic risk but heterozygotes and homozygous dominants would be at equal risk. For the case of monogenic risk in which heterozygous dominants and homozygous dominants have equivalent phenotypes, we will assume the dominant and recessive alleles are in Hardy-Weinberg equilibrium. The sum of heterozygotes and homozygous dominant fractions would thus be $0.4=2pq+q^2$. 'p' is the allele frequency of recessive and 'q' of dominant alleles such that p+q=1. Solving this quadratic equation for q, we find q=0.23 as the only physically possible solution since $q \leq 1$.

Thus, for the case of a dominant monogenic primary genetic risk factor, the sum of inherited alleles coding for risk would be 0.23. One should also consider the possible values of q for multigenic or polygenic genetic risks. For multigenic risk the average value of q would be less than 0.23, and for polygenic risk average q's would be on the order of 0.5 or higher.

These estimates are in the realm of possibility if there were no physiological effect on reproductive fitness for homozygous or heterozygous states. The physiological effect would be limited to a risk of death by colon cancer at advanced age. Since the average rate of gene mutations leading to gene loss is about $3\times10^{-5}$ per human generation and there have been about $10^4$ human generations, the accumulated mutant fraction of about 0.3 would be expected for the sum of a set of neutral alleles for a single gene.

A hypothesis that primary genetic risk for colon cancer is defined by any of a set of non-deleterious dominant mutations in one or several genes is thus not inconsistent with the calculated primary risk fraction of 0.4. The physiological effect of such a dominant mutation could affect initiation, promotion or progression, there being no way to differentiate among these possibilities with existing data or understanding of carcinogenesis.

Case II: Genetic Risk is Conferred by Homozygosity for a Recessive Mutation Non-Deleterious for Reproductive Fitness.

In the case where primary genetic risk for colon cancer requires inheritance of two recessive alleles of the same gene, neither of which affect reproductive fitness, the fraction of recessive homozygotes would be $q^2=0.4$ and $q=0.63$ for a monogenic disorder.

Since these recessive alleles in homozygous or heterozygous form have by our definition no effect on reproductive fitness, that they might have reached so high a fraction in present day populations if the mutation rate for a single gene were about twice the average for all gene inactivating mutations or if the risk were distributed over several different genes. As in Case I, one could not logically deduce which stage of carcinogenesis might be affected by the recessive homozygous state.

Case III: Genetic Risk is Conferred by a Recessive Mutation Deleterious for Reproductive Fitness.

A third possibility is that risk is conferred by a set of alleles in one or more genes in which homozygosity for such mutations is lethal in embryos or at least prevents reproduction. We again assume that these alleles are in Hardy-Weinberg equilibrium and that mutations leading to gene loss, average about $3\times10^{-5}$ per generation. From these assumptions we would expect the sum of mutant allele fractions for heterozygotes in any one gene to range from about 0.005 to 0.03 in the population. The actual value for any gene would depend on gene size and the presence of particularly marked mutational hotspots. For these to sum to 0.4, a multigenic model is obviously required. Forty separate genes each at a Hardy-Weinberg equilibrium value of about 1% would be a hypothesis consistent with these calculations.

A model considering a polygenic combination of deleterious recessive alleles would have to consider a very large number of genes (>1000). This consideration leads us to conclude that a combination of LOH events during promotion involving two or more genes carrying alleles deleterious for fitness is an unlikely scenario. In colon cancer, it would appear that any required event involving loss of heterozygosity would occur during promotion since the events of initiation are accounted as loss of two wild-type APC alleles, and events in progression would not be rate-limiting. One inherited condition of heterozygosity would be sufficient to account for primary risk since any number of required LOI events would presumably place all individuals at equal risk.

In summary, a primary genetic risk fraction of 0.4 or higher could be conferred by mutant alleles of one or a few genes if reproductive fitness were not affected. But 40 or so genes would seem to be required to create so high a primary genetic risk fraction if homozygosity for the mutant alleles did prevent reproduction. In the former case, the original alleles occurring as hotspot mutations would have arisen and been fixed multiple times throughout human history. In the latter case, selection against ancient deleterious mutations would leave only relatively recent mutations. In large present day populations, such as those of Asia, Africa and Europe, these would be expected to be distributed over very large numbers of families.

The implications of a minimum primary genetic risk fraction of 0.4 and the consideration of the cases considered here have obvious application in designing a means to find the gene or genes hypothetically carrying such risks.

The Factor Accounting for Connected Risks, $F_H$.

As may be seen in Table 4, $f_h$ increases markedly in historical time for three of the four cohorts and has a maximum value of 0.24 in the most recent European-American male cohort for which $f_h$ may be calculated. Values for males are generally higher than for females.

This factor accounts for both underdiagnoses, underreporting, and deaths of persons at risk of colon cancer by other diseases which share the genetic and/or environmental risk factor(s). Underdiagnoses and underreporting should have decreased from 1930 to 1992. The increasing value of $f_h$ is probably in part accounted for by this trend. On the other hand, the low value of $f_h$ derived from the populations born in this century suggests that the genetic and/or environmental risk factors for colon cancer are responsible for a significant fraction of other deaths. Given that colon cancer accounts for somewhat less than 5% of all deaths and that the value of $f_h$ is about 0.2, one must consider that risks for colon cancer are associated with as much as 25% of all deaths. So large a fraction could comprise all cancer deaths; alternately, the genetic or environmental risk factors for colon cancer could contribute to a large fraction of vascular disease.

As noted in the text, $f_h$ is an approximation forced upon us by ignorance of any forms of death sharing risks with colon cancer. It is the shakiest part of our modeling effort and represents an area in which more theoretical work is needed.

Mutation Rates in Initiation.

Our estimates of the rate of the first initiation mutation for the condition n=2 varies from 4 to $8\times10^{-8}$ over all four gender and ethnic cohorts for the birth year cohorts from the 1840s to 1940s. In making these estimates, we have relied on Grist et al. (1992. *Mut. Res.* 266:189–196) who estimated that the ratio of the loss of an active gene by primary mutation was approximately one third the rate of allelic loss by LOH. Thus, $r_j=3\ r_i$ has been used to calculate $r_i$ after the product $r_i r_j$ was calculated. These values are remarkably similar to observed rates of spontaneous mutations for gene inactivation in human cell culture observed to be about $10^{-7}$ per cell division. They are almost identical to an estimate of about $0.7\times10^{-7}$ per stem cell division derived from the age dependent Hprt mutant fractions in human peripheral T cells assuming three stem cell divisions per year (FIG. 12) (Bigbee, W. et al., 1998. *Mut. Res.* 397:119–36; Branda, R. et al., 1993. *Mut. Res.* 285:267–79; Davies, M. et al., 1992. *Mut. Res.* 265:165–71; Finette. B. et al., 1994. *Mut. Res.* 308:223–31; Henderson, L. et al., 1986. *Mutagenesis.* 1:195–200; Hirai, Y. et al., 1995. *Mut. Res.* 329:183–96; Hou, S. et al., 1995. *Mol. Mutagen.* 25:97–105; Huttner, E. et al., 1995. *Mut. Res.* 348:83–91; Liu, Y. et al., 1997. *Environ. Mol. Mutagen.* 29:36–45; McGinniss, M. et al., 1990. *Mut. Res.* 240:117–26; Tates, A. et al., 1991. *Mut. Res.* 253:199–213).

We are persuaded that these values are consistent with a model of loss of the first APC allele in colonic stem cells at a rate of about $7\times10^{-8}$ per stem cell division and a rate of LOH for the second allele at a rate of about $2.1\times10^{-7}$ per stem or transition cell division.

So close are these calculated values to observed human in vivo mutation and LOH rates that we will assume n=2 for colon cancer initiation until contradictory evidence is discovered. The mutation rate for European-American Females is essentially invariant at $7\times10^{-7}$ with historical time. But the data suggest a significant increase in mutation rates in both male cohorts from a steady value of $4 \times 10^{-7}$ from the 1840s through 1880s to over $6 \times 10^{-7}$ from the 1840s through the 1940s. African-American Females appear to show a steady increase from $4 \times 10^{-7}$ in the 1840s to the 1900s when it reaches the rate of $7 \times 10^{-7}$ seen in European-American Females.

Mutation Rates in Promotion.

We have no idea how many genetic changes are required for promotion in colon cancer and thus must consider the value for the geometric mean of the mutation rates for m=1, 2, 3 . . . . as our estimate of $r_A$.

These genetic changes could be gene "activation" missense mutations, gene inactivation events, LOH for an inherited heterozygous state, or loss of imprinting of a gene by other mechanisms (LOI). These processes could involve point mutations, recombination, chromosomal and or chromosomal segment loss. As noted above, we believe, on the basis of population genetics, there could be one and only one promotional LOH event in the case of an inherited recessive allele deleterious for fitness in the inherited homozygous state.

For the case m=1, the estimated value of $r_A$ is about $2 \times 10^{-7}$ per cell division for females and $8 \times 10^{-8}$ in males a value which is approximated by LOH in human T cells in vivo or gene inactivation of a somewhat larger than average gene. It is much lower than the colonic stem cell LOH rate of $7 \times 10^{-6}$ derived from Fuller et al. (Fuller, C. et al., 1990. Br. J. Cancer. 61, 382–384) and Jass, J. and Edgar, S. (1994. Pathology. 26:414–417). These ideas address the case of a monogenic condition. If any of multiple genes were involved, then activation of any of several proto-oncogenes might also be considered a numerically reasonable hypothesis.

For the case of m>1, the estimate of $r_A$ rises with m as indicated in Table 4. As in our previous effort (Herrero-Jimenez P. et al., 1998. Mut. Res. 400:553–787) it is clear that for m=1 no increase in promotional mutation rates above those seen in normal human T cells need be invoked to account for the age-specific colon cancer rates in humans. For m=2, a recombination rate somewhat higher than $7 \times 10^{-6}$ would be required.

Curiously, the historical estimate of this promotion mutation assuming m=1 is remarkably constant for both European and African-American males at about $8 \times 10^{-8}$. For both European-American and African-American females it appears to have risen significantly from the mid-ninetieth century to a constant level of about $2.5 \times 10^{-7}$ since the 1890s.

The differences between the genders and similarities between the ethnic groups may give us some reason to place confidence in these results. This would lead us to ask what environmental changes affected all women beginning in the 1860s that was completed by the 1890s which might conceivably have affected promotional mutation rates. On the other hand, the differences, while apparent, may have arisen by the action of unknown biases in reporting or diagnosis which were in some way gender specific. Given the economic differences of the ethnic groups, however, one would have expected such biases to effect comparison between ethnic groups. Such differences, do not appear at all.

Adenomatous Growth Rates.

These values are extraordinarily constant at about 0.2 for males and 0.17 for females over the entire historical period analyzed. The gender specific differences appear to be real and constant over a century of birth year cohorts. There appear to be no differences between the two ethnic groups. It would appear that the many environmental changes during the century observed have had no effect on the colon adenomatous net growth rate.

It is worth noting that these net adenomatous growth rates of 0.2 and 0.17 doublings per year are remarkably similar to the net growth rates of children which are about 0.16 (FIGS. 11A, 11B). Net colon carcinoma growth rates are about 20 doublings per year which may be compared to the net growth rate of the human fetus of some 54 doublings per year.

These similarities give a quantitative basis for the idea that the genetic steps of carcinogenesis recreate the conditions of fetal and postnatal growth in reverse. "Oncogeny recapitulates ontogeny" sums up this idea. In this scenario, the mutations permitting adenomatous growth take the cell back to the growth rates of children while the additional change(s) creating a carcinoma cell permit the more rapid growth rate of fetal life.

It is necessary to note that the observations of a, b and t were made in adult colons. It would be interesting to know if t changes in neonatal and childhood growth. Actually, we do not even know at this point if childhood growth involves an increase in the number of stem cells, an increase in the size of turnover units or both. The turnover rate in normal adult colons is about 3 divisions per year and in colonic adenomas about 9 divisions per year. But in colon carcinomas the death rate is approximately the same as in adenomas, about 9 per year, while the division rate rises to 29 per year (Despite this higher division rate, one should note that the average time between carcinoma cell divisions is about 13 days, far longer than the one day division times of cells in culture.).

High LOH and LOI Levels in Human Colon Carcinomas.

The fraction of humans showing LOH or LOI for a particular reporter locus is generally about 0.22. Since this high fraction would not be produced in adenomatous growth at the LOH rate observed in human T cells of about $2 \times 10^{-7}$ mutations per cell division, we considered what rate of LOH/LOI would be necessary to achieve such a fraction. This rate was calculated out to be about $4 \times 10^{-4}$ per cell division. This represents an estimated 2000 fold greater rate than observed in normal human lymphoid cells in vivo and in vitro and about 60 fold higher than estimated for colon stem cell LOH rates. So high a rate would accommodate a value of m=4 LOH/LOI events required for promotion (Table 5).

These calculations yield the LOH or LOI rates per cell division if all of the LOH and LOI observed in carcinomas occurred during the growth of adenomas leading to a single initial carcinoma cell.

Even if this high LOH and LOI rate occurred in colon adenomas, it would not necessitate the conclusion that the number of promotional events were 3 or 4 or that LOH or LOI were involved in promotion. Even if the LOH/LOI rates increased to $4 \times 10^{-4}$ in adenomas, the necessary promotion event might still be a single point mutation occurring at a rate of $2 \times 10^{-7}$ per cell division.

A comment on a common error in this matter of high LOH/LOI levels in tumors is in order. Some cancer researchers have used only the number of net doublings in adenomatous growth to account for an LOH/LOI fraction of 0.22. This would be the log2(adenoma cell number at the end of promotion), which is or about 17. But one requires the total number of linear divisions between the first adenoma and first carcinoma cell for this calculation. This number is about 567.

Robustness of the Model

In order to calculate the parameters of our three-stage carcinogenesis model for several birth year cohorts, maximum likelihood techniques were avoided by making several approximations. We recognize that these approximations might have led to an inadequate determination of the actual values.

Survival data were obtained by observations from a small, possibly unrepresentative population (Eisenberg, H. et al., Cancer in Connecticut: Survival Experience, 1935–1962, Hartford, Conn., Connecticut State Department of Health, ©1968; Cutler, S. and Ederer, F. (eds), End Results and Mortality Trends in Cancer; NCI Monograph No. 6, National Cancer Institute, Bethesda, Md., ©1961; Axtell, L. et al. (eds), Cancer Patient Survival; Report Number 5, National Cancer Institute, Bethesda, Md., ©1976; Ries, L. et al., 1983. *JNCI*. 70:693–707; Miller, B. et al., (eds), SEER Cancer Statistics Review: 1973–1990, National Cancer Institute, Bethesda, Md., ©1993; Ries, L. et al., (eds), SEER Cancer Statistics Review: 1973–1994, National Cancer Institute, Bethesda, Md., ©1997; Ries, L. et al., (eds), SEER Cancer Statistics Review: 1973–1996, National Cancer Institute, Bethesda, Md., ©1999; Beart, R. et al., 1995. *J. Amer. Coll. Surg.* 181:225–236). Table 6 shows the effects of a 10% error in the estimate of the relative survival on the calculated parameters for one cohort, European-American females born in the 1880s. It is clear by inspection that the population risk parameters, $F_h$ and $f_h$, as well as the initiation mutation rate, $r_i$, would not be seriously affected by this range of errors. However, the terms for adenomatous growth rate and mutation during promotion are more sensitive to this type of error. Additionally, the reported survival data excluded diagnoses of colon cancer first detected at autopsy. This primarily occurs in the elderly, and may lead to a larger error in the estimated survival in the elderly. Table 5 shows the effects of a 10% error in the estimate of survival for individuals older than 75. Again by inspection, the population risk parameters $F_h$ and $f_h$ would not be seriously affected by such an error.

TABLE 6

Percentage Change in Parameter Estimates Given Errors in Data Sets
(Data for European-American females born in the 1880s were used.)

|  | $F_h$ | $f_h$ | $r_i$ | $r_A$ | $(\alpha-\beta)$ |
|---|---|---|---|---|---|
| +10% error in S(h, t) | −0.9 | +1.2 | −1.5 | −12.4 | +4.0 |
| −10% error in S(h, t) | +0.1 | −0.1 | +1.8 | +8.9 | −4.0 |
| +10% error in S(h, 75+) | −1.1 | +1.5 | +9.3 | −19.8 | 0 |
| −10% error in S(h, 75+) | +2.0 | −2.6 | −10.8 | +29.1 | 0 |
| +10% error in slope | +11.1 | −12.9 | −4.7 | 0 | 0 |
| −10% error in slope | −5.5 | +7.4 | +2.6 | 0 | 0 |
| +10% error in $A_h$ | −9.0 | −2.8 | +22.1 | −48.8 | 0 |
| −10% error in $A_h$ | +5.2 | −11.2 | −11.7 | +95.7 | 0 |
| +10% error in $A_h$ | +3.0 | +6.0 | +3.5 | 0 | 0 |
| −10% error in $A_h$ | +0.8 | −11.0 | −5.50 | 0 | 0 |
| +5 years in $t_{max}$ | +10.9 | −12.6 | −17.0 | 0 | 0 |
| −5 years in $t_{max}$ | +1.4 | −1.7 | +17.2 | 0 | 0 |
| +10% error in $\alpha-\beta$ | 0 | 0 | −4.7 | −38.0 | 0 |
| −10% error in $\alpha-\beta$ | 0 | 0 | +5.4 | +95.7 | 0 |

We also tested the robustness of our approach by determining how much an error in any one of the several observations derived from the raw mortality data by inspection would affect estimates of the parameters (Table 6). At this stage of model development and application, they alert us to the uncertainty of our estimates of the promotional mutation rate, $r_A$, while indicating a general robustness with regard to estimates of all other derived parameters.

Generality of the Model for Other Cancers

We have begun analysis of the data for other cancers and find the primary data sets to be as well-behaved as those for colon cancer (http://cehs4.mit.edu). The application of the general model has led to preliminary estimates of adenomatous growth rates and mutation rates similar to those observed in colon cancer. However, the estimates of the fraction at risk are not historically constant for cancers of the lung, stomach and brain, nor for leukemia and lymphoma. The fraction at risk, $F_h$, for stomach cancer has shown a monotonic decline for the historical period studied while all others have shown an increase relative to the birth year cohorts of the early to mid nineteenth century.

The form of the function of OBS(h,t) is remarkably similar among cancers, but some cancers such as testicular cancer (FIG. 13), Hodgkin's disease, bone cancer and breast cancer all appear to consist of two clearly separate groups at risk requiring independent modeling for each group as in Equation 13.

Further Development of the General Model

The general model represented by Equations 22 and 34 lends itself to further useful manipulation and application. These could include modeling of diseases such as HNPCC which are caused by inheritance of heterozygosity for a recessive but powerful mutator allele for any of a set of genes involved in mismatch repair. Epidemiologists express themselves in terms of "relative risk." It should be straightforward to combine this concept with the general model developed here. A ratio of OBS*(h,t) functions would represent a "relative risk" comparison between populations differing in mutation rates, adenomatous growth rates, etc. Similarly one could now use this approach to set up a quantitative model for probabilities of recurrent cancer in persons surviving a first cancer assuming therapeutic measures had no effect on that probability.

Appendix (Example 2)

$$A_h = \int_0^\infty OBS^R(h, y)dt$$

$$= \int_0^\infty \frac{F_h \cdot (1 - S(h, t)) \cdot P_{OBS}(h, t)}{F_h + (1 - F_h) \cdot e^{-1/f_h \int_0^t (1-S(h,t)) \cdot P_{OBS}(h,t)dt}} dt$$

$$= \int_0^\infty \frac{F_h \cdot (1 - S(h, t)) \cdot P_{OBS}(h, t) \cdot e^{-1/f_h \int_0^t (1-S(h,t)) \cdot P_{OBS}(h,t)dt}}{F_h \cdot e^{-1/f_h \int_0^t (1-S(h,t)) \cdot P_{OBS}(h,t)dt} + (1 - F_h)} dt$$

In order to permit integration, we introduce the variable v such that:

$$v = -1/f_h \int_0^t (1 - S(h, t)) \cdot P_{OBS}(h, t) dt$$

$$\frac{dv}{dt} = -1/f_h \cdot (1 - S(h, t)) \cdot P_{OBS}(h, t) \cdot e^{-1/f_h \int_0^t (1-S(h,t)) \cdot P_{OBS}(h,t) dt}$$

This expression is Equation 26 in context. Note that by first dividing R(h,t) from OBS(h,t), we have avoided needing to characterize R(h,t), which is itself not explicitly integrable.

The use of the maximum value of OBS*(h,t) to define $F_h$ in terms of $\kappa_h$ and $f_h$.

Our third equation in our explicit derivation of the fraction at risk, $F_h$, came from the observation that the mortality curves adjusted for survival and underreporting reached a maximum. Using Equations 19 and 21, we note that:

$$OBS^*(h, t) = \frac{F_h \cdot \kappa_h \cdot (t - \Delta_h)^{n-1}}{F_h + (1 - F_h) \cdot e^{\frac{1}{f_h} \int_0^t (1-S(h,t)) \kappa_h (t-\Delta_h)^{n-1} dt}}$$

$$\frac{F_h \cdot \kappa_h \cdot (t - \Delta_h)^{n-1}}{F_h + (1 - F_h) \cdot e^{l(t)}}$$

Evaluating the derivative at age $t = t_{max}$, where the derivative of OBS*(h,t) equals 0, we observe:

$$\frac{dOBS(h, t)}{dt}\bigg|_{t_{max}} =$$

$$\frac{(n-1) \cdot F_h \cdot \kappa_h \cdot (t_{max} - \Delta_h)^{n-2} \cdot (F_h + (1 - F_h) \cdot e^{l(t_{max})})}{(F_h + (1 - F_h) \cdot e^{l(t_{max})})^2} -$$

$$\frac{F_h \cdot \kappa_h \cdot (t_{max} - \Delta_h)^{n-1} \cdot \frac{dl(t)}{dt}\big|_{t_{max}} \cdot (1 - F_h) \cdot e^{l(t_{max})}}{(F_h + (1 - F_h) \cdot e^{l(t_{max})})^2} = 0$$

Evaluating common terms this simplifies to:

$(n-1) \cdot f_h \cdot (F_h \cdot e^{-l(t_{max})} + (1-F_h)) - (1 - S(h, t_{max})) \cdot \kappa_h (t_{max} - \Delta_h)^n (1 - F_h) = 0$ Solving for the fraction at risk, $F_h$, creates Equation 27.

$$F_h \cdot [(n - 1) \cdot f_h (1 - e^{-l(t_{max})}) - (1 - S(h, t_{max})) \cdot \kappa_h \cdot (t_{max} - \Delta_h)^n] =$$

$$(n - 1) \cdot f_h - (1 - S(h, t_{max})) \cdot \kappa_h \cdot (t_{max} - \Delta_h)^n$$

$$F_h = \frac{(n - 1) \cdot f_h - (1 - S(h, t_{max})) \cdot \kappa_h \cdot (t_{max} - \Delta_h)^n}{(n - 1) \cdot f_h (1 - e^{-l(t_{max})}) - (1 - S(h, t_{max})) \cdot \kappa_h \cdot (t_{max} - \Delta_h)^n}$$

$$F_h = \frac{(n - 1) \cdot f_h - (1 - S(h, t_{max})) \cdot \kappa_h \cdot (t_{max} - \Delta_h)^n}{(n - 1) \cdot f_h \cdot \left(1 - e^{-\frac{1}{f_h} \int_0^{t_{max}} (1-S(h,t)) \kappa_h (t-\Delta_h)^{n-1} dt}\right) -}$$

$$(1 - S(h, t_{max})) \kappa_h \cdot (t_{max} - \Delta_h)^n$$

The expressed mortality rate from the OBServed disease, $P_{OBS}(h,t)$, within the group at risk, $F_h$.

Calculation of the Number of Total Cell Divisions in an Adenoma, (T-a) Years after its Initiation To properly evaluate the promotion mutation rate in terms of mutations per cell division, we need to know the total number of cell divisions that an adenoma would have undergone between the age at initiation, a, and the age at promotion, t.

First, we consider the number of cells in the adenoma. The initial number of cells in a surviving adenoma is not one, but $\alpha/(\alpha - \beta)$. (This is because of the stochastic redistribution of surviving cells among all initiated adenomas into the surviving adenomas.) The colony also grows at a rate of $(\alpha - \beta)$ per year, such that the number of cells in the adenoma after (t-a) years is:

$$\frac{\alpha}{\alpha - \beta} \cdot 2^{(t-a)(\alpha-\beta)}$$

Since the division and death rates of an adenoma are approximately equal, we can divide a year into a periods. We can then write an equation for the number of cells in the adenoma as a function of the number of these periods that have elapsed, $\delta$:

$$\frac{\alpha}{\alpha - \beta} \cdot 2^{[\alpha(t-a)]\frac{(\alpha-\beta)}{\alpha}} = \frac{\alpha}{\alpha - \beta} \cdot 2^{\delta \frac{(\alpha-\beta)}{\alpha}}$$

The number of total cell divisions havinf occurred in the adenoma can then be related to the number of cells. In order to have a colony of a certain size, $N_{adenoma}$, we recognize that there must have been ($N_{adenoma} \div 2$) divisions within the last period of possible division:

$$\frac{\alpha}{\alpha - \beta} \cdot \frac{2^{\delta \frac{(\alpha-\beta)}{\alpha}}}{2}$$

Consequently, the total number of cell divisions is the sum of the number of divisions needed to give each of the intermediate sizes of the adenoma up to the last period, $\delta$:

$$\sum_{i=1}^{\delta} \frac{\alpha}{\alpha - \beta} \cdot \frac{2^{i \cdot \frac{(\alpha-\beta)}{\alpha}}}{2} = \sum_{i=1}^{\alpha(t-a)} \frac{\alpha}{\alpha - \beta} \cdot \frac{2^{i \cdot \frac{(\alpha-\beta)}{\alpha}}}{2}$$

This summation can be solved explicitly as:

$$\frac{\alpha}{\alpha - \beta} \cdot \frac{2^{\beta/\alpha}(2^{(\alpha-\beta)(t-a)} - 1)}{2^{(\alpha-\beta)/\alpha} - 1}$$

We actually find that taking the integral instead of the summation above gives us a reliable and easier to remember estimate:

$$\left(\frac{\alpha}{\alpha - \beta}\right)^2 \cdot \frac{(2^{(\alpha-\beta)(t-a)} - 1)}{2 \ln 2}$$

Last, we recognize that for every division, each of the two daughter cells can acquire the promotion mutation. Therefore, the number of opportunities for promotion after (t−a) years is just twice the total number of divisions:

$$\left(\frac{\alpha}{\alpha-\beta}\right)^2 \cdot \frac{(2^{(\alpha-\beta)(t-a)}-1)}{\ln 2}$$

as included in Equation 21.

The Growth Rate of Adenomas (α−β)

In order to estimate the initiation and promotion mutation rates (Equations 26 and 30), we need to know the average growth rate of an adenoma. While the division and death rates, α and β respectively, can be determined in vivo, the difference (α−β) could not, as it is too small to estimate with any useful precision. The adenomatous growth rate can, however, be estimated directly from the mortality gurves. We will illustrate this using the case (n=2, m=1). The calculated adenomatous growth rate is approximately the same for all other cases.

For ages below 54 years, we can estimate the adjusted observed mortality rate OBS*(h,t) as:

$$OBS^*(h,t) = OBS(h,t) \div [R(h,t)(1-S(h,t))] \approx F_h P_{OBS}(h,t)$$

where $$P_{OBS}(h,t) = 2\tau^2 r_1 r_2 \frac{\alpha-\beta}{\alpha} \int_0^t a N_a \frac{d\left(1 - e^{-r}A \cdot \left(\frac{\alpha}{\alpha-\beta}\right)^2 \cdot \frac{2^{(\alpha-\beta)(t-a)}-1}{\ln 2} \cdot \frac{\alpha_c - \beta_c}{\alpha_c}\right)}{d(t-a)} da$$

As a first approximation, we assumed a constant number of cells in the target tissue. For clarity, we group those parameters that do not vary with age (e.g., $F_h$ is calculated in $C_1$):

$$OBS^*(h,t) = C_1 \int_0^t a \frac{d(1 - e^{-C_2 \cdot (2^{(\alpha-\beta)(t-a)}-1)})}{d(t-a)} da$$

To help us solve this integral, we recognize that $e^x \approx 1+x$ when x is small. This yields:

$$OBS^*(h,t) \approx C_1 \int_0^t a \frac{d(1 - (1 - C_2 \cdot (2^{(\alpha-\beta)(t-a)}-1)))}{d(t-a)} da$$

$$\approx C_1 C_2 \int_0^t a \frac{d(2^{(\alpha-\beta)(t-a)}-1))}{d(t-a)} da$$

$$\approx C \int_0^t a[2^{(\alpha-\beta)(t-a)}(\alpha-\beta)\ln 2] da$$

$$\approx \frac{C}{(\alpha-\beta)\ln 2}[2^{(\alpha-\beta)t} - t(\alpha-\beta)\ln 2 - 1]$$

where we combined the two constants, $C_1 C_2 = C$. If we now take the derivative of OBS*(h,t), we observe:

$$\frac{d(OBS^*(h,t))}{dt} \approx C[2^{(\alpha-\beta)t} - 1] \approx C2^{(\alpha-\beta)t}$$

The $\log_2$ of dOBS*(h,t)÷dt is a function of t whose slope is the adenomatous growth rate, α−β:

$$\log_2 \frac{d(OBS^*(h,t))}{dt} \approx (\alpha-\beta)t + \log_2(C)$$

This approximation is valid only when $2 \cdot [(\alpha-\beta)t]^{-1} \gg 1$, so when estimating the adenomatous growth rate, one needs to be careful not to use data from the age groups below age 14.

We likewise approximated the adenomatous growth rate accounting for cell number increases during childhood. When we calculated the derivative of OBS*(h,t) using the data for t>17.5, we see that:

$$\frac{d(OBS^*(h,t))}{dt} \approx C\left[2^{(\alpha-\beta)t} - \frac{2^{16.5(\alpha-\beta)}}{2 - 2^{-16.5(\alpha-\beta)}(1 + 16.5\ln 2(\alpha-\beta))}\right] \approx C2^{(\alpha-\beta)t}$$

Figure 18:
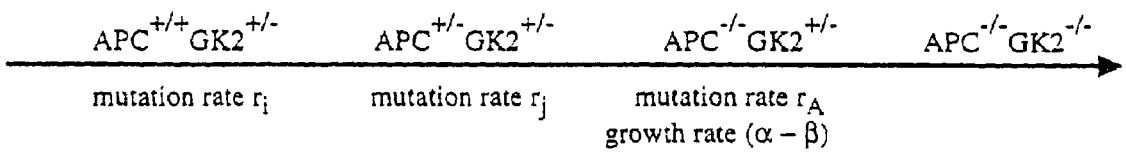
FIG. 18 is a schematic demonstrating a model for sporadic colon cancer for the case in which n=2 and m=1. Initiation is modeled as the loss of function of either APC allele followed by loss of heterozygosity of the second allele. Promotion is modeled as loss of heterozygosity for any of a set of second gatekeeper genes. Primary genetic risk in this example is defined as inherited heterozygosity for any second gatekeeper gene for colon cancer.

The log2 of this function plotted vs. t is also a straight line as shown in FIG. 18. The slope of this function is (α−β).

The average Promotion Mutation Rates, $r_A$, (m=1)

In calaculating the promotion mutation rate, $r_A$, for the case where only one mutation was required for the promotion of an adenoma cell, we used the approximation that the cumulative probability would be one-half after $\Delta_h$ years, where $\Delta_h$ represents the average time between initiation and promotion. Using Equation 21, this means:

$$\frac{1}{2} = 1 - e^{-r}A \cdot \left(\frac{\alpha}{\alpha-\beta}\right)^2 \cdot \frac{1}{\ln 2} \cdot \frac{\alpha_c - \beta_c}{\alpha_c} \cdot (2^{(\alpha-\beta)\Delta_h} - 1)$$

$$\Delta_h = \frac{\log_2\left[1 + \left(r_A \cdot \left(\frac{\alpha}{\alpha-\beta}\right)^2 \cdot \frac{1}{[\ln(2)]^2} \cdot \frac{\alpha_c - \beta_c}{\alpha_c}\right)^{-1}\right]}{\alpha-\beta}$$

However, the assumption that the cumulative probability is approximately one-half at the average time between initiation and promotion is true only if the distribution for the probability of promotion can be approximated by a normal distribution. As (α−β) increases, the actual distribution can no longer be approximated to be a normal distribution. In this case, we can use the exact calculation to evaluate the expected value for the time between initiation and promotion. Expected value for a continuous random variable, in our case the time between initiation and promotion, t−a, is defined as:

$$\Delta_h = \int_{-\infty}^{\infty} (t-a) P[t-a] d(t-a)$$

We evaluate the expected time between initiation and promotion to be:

$$\Delta_h = \int_0^{\infty} (t-a) \frac{d\left(1 - e^{-r_A \cdot \left(\frac{\alpha}{\alpha-\beta}\right)^2 \cdot \frac{1}{\ln 2} \cdot \frac{\alpha_c - \beta_c}{\alpha_c} \cdot (2^{(\alpha-\beta)(t-a)} - 1)}\right)}{d(t-a)} d(t-a)$$

$$= \frac{-e^{-r_A \cdot \left(\frac{\alpha}{\alpha-\beta}\right)^2 \cdot \frac{1}{\ln 2} \cdot \frac{\alpha_c - \beta_c}{\alpha_c}} \cdot Ei\left[r_A \cdot \left(\frac{\alpha}{\alpha-\beta}\right)^2 \cdot \frac{1}{\ln 2} \cdot \frac{\alpha_c - \beta_c}{\alpha_c}\right]}{(\alpha - \beta)\ln 2}$$

where Ei is the exponential integral function. A computational tool such as Mathematica™ (ExpIntegralEi function) or Matlab™ (exprint function) can be used to evaluate the exponential integral function.

The Average Promotion Mutation Rates, $r_A$, m>1

Figure 21:
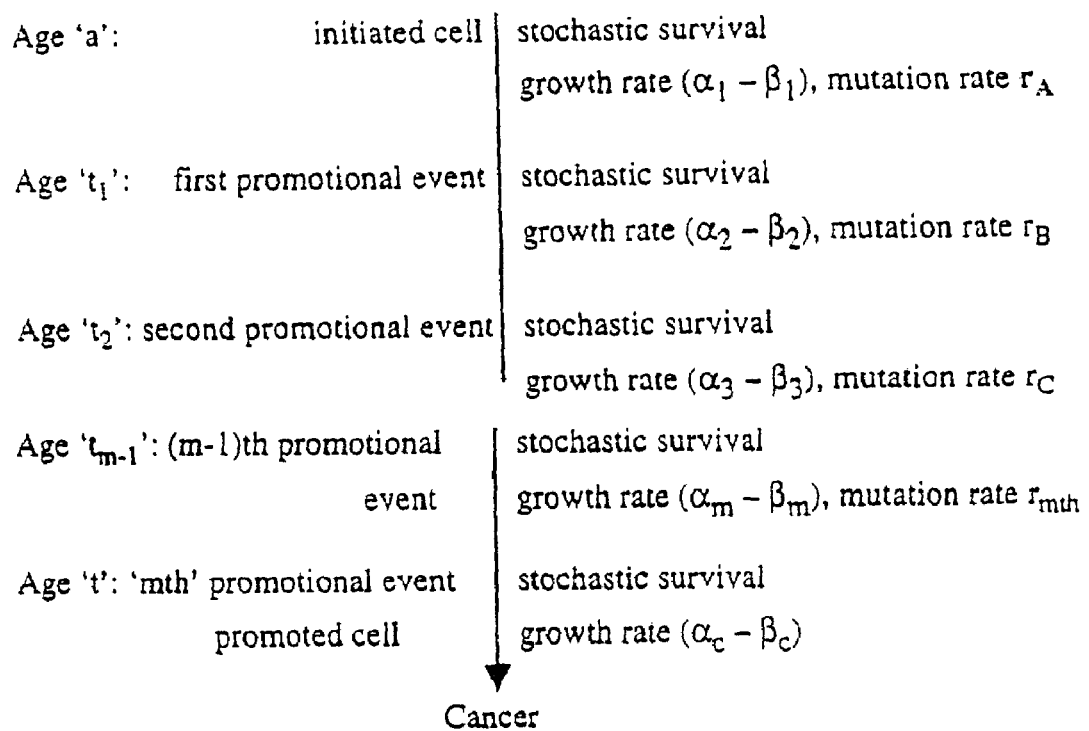
FIG. 21 is a diagram of promotion for "m" necessary events.

When a cell in an adenoma acquires the first promotional mutation, this cell has the potential to divide and become a distinct colony of cells now containing one promotional mutation. A cell within this colony is a target for a second promotional event, producing a new colony within the adenoma, now made up of cells with two promotional mutations. This process continues until a cell acquires all necessary 'm' promotional mutations, thereby producing a carcinoma cell (FIG. 21). As was the case for a newly initiated cell, we must consider the possibility that any cell that acquires a new promotional mutation could undergo stochastic extinction before developing a colony.

The adenoma itself would thus appear to be a mix of colonies of cells containing zero or more of the promotional events, and the delay in the rise of the mortality curves, $\Delta_h$, is now the sum of the average time between each promotional event.

Probability of $(m-1)^{th}$ promotion mutation by age $(t_{m-2} < t_{m-1} < t) \times$ Probability of $m^{th}$ promotion mutation at age t $$\int_a^t \frac{d\left(1 - e^{\left[-mr_A \cdot \left(\frac{\alpha_1}{\alpha_1-\beta_1}\right)^2 \cdot \frac{2^{(\alpha_1-\beta_1)(t_1-a)} - 1}{\ln 2} \cdot \frac{\alpha_2 - \beta_2}{\alpha_2}\right]}\right)}{d(t_1 - a)}$$

$$\int_{t_1}^t \frac{d\left(1 - e^{\left[(-m-1)r_B \cdot \left(\frac{\alpha_2}{\alpha_2-\beta_2}\right)^2 \cdot \frac{2^{(\alpha_2-\beta_2)(t_2-t_1)} - 1}{\ln 2} \cdot \frac{\alpha_3 - \beta_3}{\alpha_3}\right]}\right)}{d(t_2 - t_1)}$$

$$\int_{t_{m-2}}^t \frac{d\left(1 - e^{\left[-2r_{m-1} \cdot \left(\frac{\alpha_{m-1}}{\alpha_{m-1}-\beta_{m-1}}\right)^2 \cdot \frac{2^{(\alpha_{m-1}-\beta_{m-1})(t_{m-1}-t_{m-2})} - 1}{\ln 2} \cdot \frac{\alpha_m - \beta_m}{\alpha_m}\right]}\right)}{d(t_{m-1} - t_{m-2})}$$

$$\frac{d\left(1 - e^{\left[-r_m \cdot \left(\frac{\alpha_m}{\alpha_m-\beta_m}\right)^2 \cdot \frac{2^{(\alpha_m-\beta_m)(t_{m-1}-t_{m-2})} - 1}{\ln 2} \cdot \frac{\alpha_c - \beta_c}{\alpha_c}\right]}\right)}{d(t - t_{m-1})}$$

$dt_1 dt_2 dt_3 \ldots dt_{m-1}$ where the first promotion mutation occurs at any age, $t_1$, between initiation and death, the second promotion mutation occurs at any age, $t_2$, between the first mutation and death, the third promotion mutation occurs at any age, $t_3$, between the second mutation and death, and so forth until the last promotion mutation which must occur at age t. Again, we

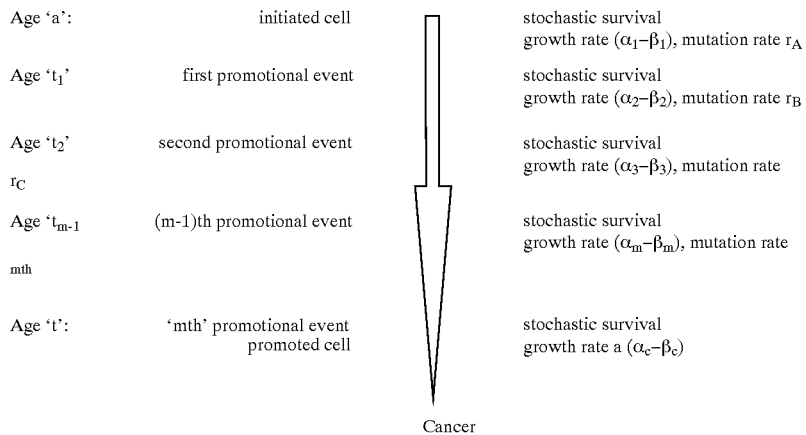

FIG. 16. Diagram of promotion for 'm' necessary events

From FIG. 16, the probability of promotion at age 't' simply follows as:

Probability of $1^{st}$ promotion mutation by age $(a<t_1<t) \times$

Probability of $2^{nd}$ promotion mutation by age $(t_1<t_2<t)$ x . . . x recognize that there are 'm' target alleles for the first promotion event, (m−1) for the second promotion event, and so forth.

We have supposed that the acquisition of a new promotional event changes either the cell kinetic rates, $\alpha_x$ and $\beta_x$, or the promotion mutation rate, $r_x$, for that cell. While we are unable to estimate each cell kinetic rate and promotion mutation rate independently for each step, we might imagine that there exists an average promotion mutation rate, $r_A$, and an average cell kinetic growth rate, $\alpha-\beta$ that describes a similar process of 'm' promotional mutations such that the total delay of onset of the disease is equivalent. The probability of promotion is now of the simpler form:

$$\int_a^{t} \frac{d\left(1 - e^{\left(-mr_A \cdot \frac{\alpha}{\alpha-\beta} \cdot \frac{(\alpha-\beta)(t_1-a)-1}{\ln 2}\right)}\right)}{d(t_1-a)}$$

$$\int_{t_1}^{t} \frac{d\left(1 - e^{\left(-(m-1)r_A \cdot \frac{\alpha}{\alpha-\beta} \cdot \frac{2^{(\alpha-\beta)(t_2-t_1)}-1}{\ln 2}\right)}\right)}{d(t_2-t_1)}$$

$$\int_{t_{m-2}}^{t} \frac{d\left(1 - e^{\left(-2r_A \cdot \frac{\alpha}{\alpha-\beta} \cdot \frac{2^{(\alpha-\beta)(t_{m-1}-t_{m-2})}-1}{\ln 2}\right)}\right)}{d(t_{m-1}-t_{m-2})}$$

$$\frac{d\left(1 - e^{\left(-r_A \cdot \left(\frac{\alpha}{\alpha-\beta}\right)^2 \cdot \frac{2^{(\alpha-\beta)(t-t_{m-1})}-1}{\ln 2} \cdot \frac{\alpha_c-\beta_c}{\alpha_c}\right)}\right)}{d(t-t_{m-1})} dt_1 dt_2 dt_3 \ldots dt_{m-1}$$

We can now explicitly estimate the average promotion mutation rate with respect to the expected time between each pair of consecutive events. Here, we solve for the average interarrival time, $\Delta_x$, between each promotional event. Again we use the approximation that the average time approximately corresponds with a cumulative probability for that promotion mutation of 0.5:

$$\Delta_1 = \frac{\log_2\left(1 + \left[mr_A \cdot \frac{\alpha}{\alpha-\beta} \cdot \frac{1}{[\ln(2)]^2}\right]^{-1}\right)}{\alpha - \beta}, \Delta_2 = \frac{\log_2\left(1 + \left[(m-1)r_A \cdot \frac{\alpha}{\alpha-\beta} \cdot \frac{1}{[\ln(2)]^2}\right]^{-1}\right)}{\alpha - \beta}$$

$$\Delta_{m-1} = \frac{\log_2\left(1 + \left[2r_A \cdot \frac{\alpha}{\alpha-\beta} \cdot \frac{1}{[\ln(2)]^2}\right]^{-1}\right)}{\alpha - \beta},$$

$$\Delta_m = \frac{\log_2\left(1 + \left[r_A \cdot \left(\frac{\alpha}{\alpha-\beta}\right)^2 \cdot \frac{1}{[\ln(2)]^2} \cdot \frac{\alpha_c-\beta_c}{\alpha_c}\right]^{-1}\right)}{\alpha - \beta}$$

The total expected delay between initiation and promotion, $\Delta_h$, is simply the sum of the delays between each promotion mutations. For m>1:

$$\Delta_h = \frac{\sum_{i=2}^{m} \log_2\left(1 + \left[ir_A \cdot \frac{\alpha}{\alpha-\beta} \cdot \frac{1}{[\ln(2)]^2}\right]^{-1}\right)}{\alpha - \beta} +$$

-continued $$\frac{\log_2\left(1 + \left[r_A \cdot \left(\frac{\alpha}{\alpha-\beta}\right)^2 \cdot \frac{1}{[\ln(2)]^2} \cdot \frac{\alpha_c-\beta_c}{\alpha_c}\right]^{-1}\right)}{\alpha - \beta}$$

$$\Delta_h = \frac{(m-1) \cdot \log_2\left(1 + \left[r_A \cdot \frac{\alpha}{\alpha-\beta} \cdot \frac{1}{[\ln(2)]^2}\right]^{-1}\right)}{\alpha - \beta} +$$

$$\frac{\log_2\left(1 + \left[r_A \cdot \left(\frac{\alpha}{\alpha-\beta}\right)^2 \cdot \frac{1}{[\ln(2)]^2} \cdot \frac{\alpha_c-\beta_c}{\alpha_c}\right]^{-1}\right)}{\alpha - \beta}$$

This gives us an equation for the delay in the general case of 'm' promotion mutations, assuming that the order the promotion mutations occur is inconsequential.

If we instead suppose that each of the promotion mutations leads to either an elevated cell growth rate or an elevated mutation rate per cell year, then there would exist a particular order for the 'm' necessary promotion mutations that would be favorable for the early promotion of the tumor. We might suppose that if the particular deleterious mutations do not occur early in the order of the 'm' mutations, the individual would not accumulate all of the necessary promotion mutations within their lifetime. Using the same logic as above, we can explicitly evaluate the delay between initiation and promotion, if the 'm' mutations had to occur in a particular order:

$$\Delta_h = \frac{(m-1) \cdot \log_2\left(1 + \left[r_A \cdot \frac{\alpha}{\alpha-\beta} \cdot \frac{1}{[\ln(2)]^2}\right]^{-1}\right)}{\alpha - \beta} +$$

$$\frac{\log_2\left(1 + \left[r_A \cdot \left(\frac{\alpha}{\alpha-\beta}\right)^2 \cdot \frac{1}{[\ln(2)]^2} \cdot \frac{\alpha_c-\beta_c}{\alpha_c}\right]^{-1}\right)}{\alpha - \beta}$$

These equations allow us to estimate the average promotion mutation rate for the case where the 'm' promotion mutations occur in a completely unordered manner and the case where the 'm' promotion mutations must follow in a particular order. Of course, it is possible that only some of the promotion mutations must occur in order. For this case, where 'm' mutations are only partially ordered, these equations would describe the possible range for the average promotion mutation rate.

Example 3

Identification of Inherited Point Mutations: Background and Significance

This section reviews competing technological approaches to the identification of point mutations (e.g., single nucleotide polymorphisms) and rare point mutations carried by human populations. "SNP" implies the widely-accepted definition of inherited point mutations present in 1% or more of the population (Brookes, A. 1999. *Gene.* 234:177–186). By 'rare' point mutations we mean all point mutations present at allelic fractions less than 1%. We have previously argued on theoretical grounds that point mutations at fractions lower than 1% would need to be discovered in order to identify genes carrying alleles that are deleterious for reproductive fitness or somatically harmful in adult humans (Tomita-Mitchell, A. et al., 1998. *Gene.* 223:381–391). Based on earlier observations by population geneticists, we believe it is both useful and necessary to scan large samples of cross-sections of the ethnic groups which constitute the American population.

Significance of Inherited Human Mutations.

Discovery of Deleterious Alleles.

As a general proposition a true fine structure map of inherited human point mutations would allow classification of each gene mapped with regard to the presence or absence of dominant or recessive deleterious obligatory knockout alleles. At this writing obligatory knockout alleles are limited to stop codons and frameshift mutations. But the growing knowledge of gene-inactivating splice site mutations should allow their use as obligatory knockouts also. Similarly, increased knowledge of protein structural motifs which inactivate gene product function should allow certain missense mutations to be recognized as probable, if not obligatory, knockout mutations in the near future. These data would also lay the groundwork for determining the fraction of the total human genomic complement which carries such deleterious alleles.

Studies in human reproduction indicate that about 0.75 of all human conceptions are lost prior to birth, many in pre-implantation or early post-implantation losses unrecognized by the mother. About 0.30 are attributable to aneuploidy or chromosomal aberrations. Thus about 0.45 of all human conceptions are lost due to unknown causes (Liber and Thilly, 1983). We have explored the theoretical possibility that all or a significant fraction of these fetal losses could be due to dominant deleterious alleles or homozygosity for recessive deleterious alleles.

Dominant deleterious alleles appear to arise at a fraction of $3 \times 10^{-5}$ per gene at risk (Cavalli-Sforza, 1971). It would thus require $(0.45/3 \times 10^{-5}) = 15,000$ of such dominant deleterious alleles to account for all of a fetal wastage fraction of 0.45. Recessive deleterious alleles are expected to be carried by 1.33% of the population. On average for each gene at risk given a forward mutation rate for gene loss of $3 \times 10^{-5}$ (the Hardy-Weinberg equilibrium calculation), this estimates that the number of such recessive deleterious allele carrying genes would be $(4 \times 0.45)/(0.0133)2 = 10,130$ to account for all of a fetal wastage fraction of 0.45.

It is reasonable to consider the possibility that all, or a large fraction, of actual fetal losses arise from a combination of fewer than 10,000 recessive and fewer than 15,000 dominant deleterious allele-carrying genes in addition to the fraction caused aneuploidy and or chromosome aberrations well described by cytogeneticists. Algebraically, the sum of the number of genes carrying either recessive, NR, or deleterious, ND, alleles are related to this estimated upper bound on fetal wastage: $3 \times 10^{-5} ND + 4.4 \times 10^{-5} NR = 0.45$.

Of course, the attribution of all fetal wastage to inherited deleterious alleles provides an upper estimate on their numbers. These estimates are, however, related to estimates of the number of essential genes in yeast, zebra fish and mice which range from 5000 to 15,000 at present count.

The clinical importance of these considerations extends to consideration of asymptomatic infertility. It is possible that a significant fraction of infertile couples with no clinical indication of reproductive dysfunction may be found to carry multiple conditions of complementing heterozygosity. For instance if a couple were heterozygous for two identical recessive deleterious alleles, 7/16 of their conceptions would be lethal. If heterozygous for three identical recessive alleles, 46/64 of their conceptions would be lethal and so on.

This "Fermi calculation" is of practical value in that it suggests that the scanning of all expressed genes in the human genome would uncover fewer than 10,000 genes which carry recessive deleterious alleles and fewer than 15,000 carrying dominant deleterious alleles. Assuming 50,000 such expressed human genes, this works out to expected fractions of less than 20% and 30% respectively. For a proposed random set of 15 genes we might thus expect 3 or fewer to show a set of obligatory knockout alleles with fractions summing to about 0.3% permitting the inference that such a gene carries recessive deleterious alleles. Similarly we expect 5 or more to show no obligatory knockout alleles permitting the inference that such a gene carries dominant deleterious alleles. If we assume 100,000 random genes, these estimates are lower accordingly. But we have not chosen a random set of genes. We propose to examine 13 genes whose gene products have been identified as constituents of the nuclear DNA repair complexes. Since obligatory knockouts of such genes are expected to possibly be dominant deleterious and certainly to be recessive deleterious alleles, we expect some of these genes to carry obligatory knockouts summing to 0.5% or less and some to show no such alleles down to our limits of detection (see Table 8, Studies).

Discovery of Somatically Harmful Alleles.

It follows that such a fine structure map drawn from juvenile populations would contain somatically harmful alleles such as those which might increase somatic mutation rates and hasten the appearance of cancer or atherosclerosis. Studies to discover such alleles would involve additional analyses of proband populations for specific diseases or extremely aged populations in which carriers have been reduced by early mortality. However, the value of the proposed study in juvenile populations would be a necessary first step in such explorations.

Discovery of Alleles Specific to Ethnic Subpopulations.

It is clear that inherited polymorphisms at fractions greater than 1% vary among the major demographic groups of the world and it may be reasonably expected that such important variations will exist for deleterious alleles present at fractions less than 1%. We have already found such an example in the Hprt gene exon 6. Our initial emphasis on a large ethnically mixed sample of 50,000 juveniles will allow us to identify any allele present down to an allele fraction of about $5 \times 10^{-5}$. This strategy is designed to increase the number of obligatory knockout alleles in the initial sample and to lay the groundwork for future studies aimed at particular demographic groups.

Technological Background: High Resolution Mutational Spectrometry.

The approach described herein represents a clear and significant improvement over present and even proposed strategies. The method described herein is extremely efficient for mutation discovery and frequency estimation, because it can analyze pooled genomic DNA from a hundred thousand or even a million individuals. This is in contrast to other presently employed techniques which require assaying each individual, or small pools of at most about a dozen individuals (Trulzsch, B. et al., 1999. *Biotechniques.* 27:266–268). Since the cost per individual is not trivial, this makes mutation discovery in large populations very expensive, and these studies are required for determination of low-frequency point mutations with useful statistical precision (Hagmann, M., 1999. *Science*. 285:21–22).

There are two alternative approaches to the use of large pooled samples analyzed by high resolution mutational spectrometry as proposed herein.

The first is the sequencing of megabases of genomic DNA from a limited number of individuals. This is the "resequencing" strategy employed by a number of private companies and various NIH or DOE sponsored university laboratories and human genome centers. This approach was made possible by construction of research facilities to sequence the human genome. High throughput was naturally defined as the length of DNA sequences that could be sequenced per year. The cost per base pair of this approach is presently estimated to be about 20 cents. But we and industry analysts estimate that reasonable improvements in processing samples and an increase in scale to analyze thousands of donor samples would reduce these costs to about 2 cents per base pair.

It would thus cost some five hundred million dollars at present cost levels charged to NIH grants to examine 2.5 billion base pairs. The method described herein will cost less than three million dollars. Furthermore we focus on exons and splice sites in which most deleterious mutations are expected. In genome resequencing these sequences rarely comprise more than 5% of the length of DNA sequenced increasing the relative cost of identifying inherited deleterious alleles in any chosen gene. Unfortunately, the use of even a thousand blood samples will not reveal recessive deleterious mutations such as many of those causing cystic fibrosis and a suspected several thousand forms of fetal loss. This is because the sum of fractions of such deleterious alleles is expected to be about 1.33% since individual alleles are expected at fractions ranging from 0.3% to 0.003%. Examination of 100,000 alleles should give a worthwhile picture of these alleles and our first studies of a few thousand individuals offer support for this expectation (Tomita-Mitchell, A. et al., 1998. *Gene*. 223:381–391). Since the cost per individual is not trivial, the usual methods of mutation discovery in large populations is very expensive. We argue that our studies are required for determination of low-frequency point mutations with useful statistical precision (Hagmann, M., 1999. *Science*. 285:21–22).

The second alternative technology (to the use of high resolution mutational spectrometry on large pooled sample) is the use of microarrays of short DNA sequences (DNA chips) created to detect any and all point mutations in a given DNA sequence. Theoretically these could focus on a sample of a 100 bp sequence to detect any of the 300 single base pair substitutions and 200 single base pair additions or deletions. Practically the use of up to 16-mers has indicated that only somewhat greater than half of all point mutations are detected in this way and that the detection of variants at fractions lower than 10% is not yet feasible using this technology (Paul Berg, Standard University, personal communication). Coupled with the cost of each "chip" and creation of a chip for each sequence to be scanned and the need to prepare and analyze blood cell DNA samples for each person, we do not think that the task of identifying deleterious inherited point mutations over a large number of genes and people can be accomplished in this way without a truly massive investment.

In short, given a means to accurately measure the fractions at the desired sensitivity, the use of large pooled samples appears to be a good way to determine the type and numerical distribution of inherited point mutations in human populations. Our proposed approach using constant denaturing gel capillary electrophoresis (CDCE) to separate mutant from wild-type sequences prior to DNA amplification has already been demonstrated to have the requisite sensitivity. Furthermore, when target sequence sizes of 80–120 base pairs are used, 100% of all point mutants studied have been separated as mutant/wild-type heteroduplexes from wild-type homoduplexes (Mickey G. et al., 1995. *Biochim. Biophys. Acta*. 1260:123–31; Khrapko, K. et al., 1998. *Nucl. Acids Res.* 15:5738–5740).

One should note separation of wild-type homoduplexes from mutant-containing heteroduplexes, which we perform using constant denaturing capillary electrophoresis, may also be accomplished by HPLC and similarly predetermined temperature conditions. The physical-chemical principles of mutant separation are similar to those in CDCE: partially melted heteroduplex molecules containing a mutant sequence are retarded in columns relative to wild-type homoduplexes. Alternatively, many, but not all, single nucleotide changes can also be detected using single strand polymorphism velocity variations in capillary electrophoresis (CE-SSCP) (Gonen et al., 1999).

The mutant separation method we propose involves constant denaturant capillary electrophoresis (CDCE) to observe somatically-derived point mutation spectra in human tissues (Khrapko, K. et al., 1994. *Nucl. Acids Res.* 22:364–369; Khrapko, K. et al., 1997. *Nucl. Acids Res.* 25:685–693; Li-Sucholeiki, X.-C. et al., 1999. *Electrophoresis*. 20:1224–1232). The method coupled with high fidelity DNA amplification has been demonstrated to detect mutations in 100 bp sequences with a sensitivity of at least $10^{-6}$ in samples from several human organs (Khrapko, K. et al., 1997. *Nucl. Acids Res.* 25:685–693; Khrapko, K. et al., 1998. *Nucl. Acids Res.* 15:5738–5740).

CDCE is based on mobility differences among partially denatured double-stranded DNA fragments. These mobility differences arise from differential cooperative melting behavior among wild-type homoduplexes and various heteroduplexes formed between the majority wild-type sequences and minority mutant sequences in a complex sample such as the pooled blood samples proposed herein (Thilly, 1985). The high resolution achieved by capillary electrophoresis, as well as elimination of artifacts arising from interaction of DNA with standard cross-linked polyacrylamide gels, resulted in a means to detect and sequence rare mutants in complex samples (Khrapko, K. et al., 1994. *Nucl. Acids Res.* 22:364–369; Khrapko, K. et al., 1997. *Nucl. Acids Res.* 25:685–693; Salas-Solano, O. et al., 1998. *Anal. Chem.* 70:3996–4003; Muller, O. et al., 1995. *Anal. Chem.* 67:2974–2980; Pennisi, E., 1999. *Science*. 283:1822–1823).

Automation. Capillary separation systems offer the advantage of complete automation of sample loading, separations, fraction collection and subsequent DNA amplification of selected collections. Automated sample injection and replacement of polymer separation matrices is being used in capillary array instruments to conduct the large-scale sequencing required to determine the human genome (Mullikin J. and McMurragy, A., 1999. *Science*. 283:1867–1868). In this proposal we introduce our already-developed peak or sample collection system coupled to automated PCR.

Role of rad54 in Homologous Recombination.

One long-term goal is to determine whether the suspected dominant and recessive deleterious and/or harmful alleles uncovered by the research actually impart a mutator phenotype to a human cell. Our approach is to create heterozygous and/or homozygous cell lines at the genetic loci identified to be potential human mutator alleles and evaluate their spontaneous mutation and mitotic recombination rates in the Hprt and TK loci.

An immediate goal is to evaluate the relative efficiencies of two protocols for gene replacement, which can be used in later experiments. The genetic locus we have chosen to work with is rad54, which appears to play a central role in homologous recombination and repair of DNA double strand breaks. We hypothesize that mutations in rad54 will result in the cell having a higher spontaneous mutation rate and becoming hypermutable to agents such as ionizing radiation.

In S. cerevisiae, there are at least 9 different proteins in the rad52 epistasis group, which is involved in homologous recombination, as it affects the repair of double strand breaks (Haber, J., 1995. *Bioessays*. 17:609–20, 1995; Bai, Y. and Symington, L. 1996. *Genes Dev*. 10:2025–37; Baumann, P. and West, S. 1998. *Trends Biochem. Sci*. 23:247–51). Mammalian homologues have been identified for several of these, including rad54 (Kanaar, R. and Hoeijmakers, J., 1997. *Genes Function*. 1: 165–74). In the mouse, disruption of rad54 leads to increased radiation-sensitivity, and decreased homologous recombination (Essers, J. et al., 1997. *Cell*. 89:195–204). From these experiments, we learn that rad54 is not an essential gene; this is important as it indicates that a knockout in human lymphoblast cells should not be lethal. The human homologue is a functional one, as it complements a repair-deficient rad54 yeast mutant (Kanaar, R. et al., 1996. *Curr. Biol*. 6:828–38). The protein is a double-stranded DNA dependent ATPase, but its precise function in recombination is still undetermined (Swagemakers, S. et al., 1998. *J. Biol. Chem*. 273:28292–7). There is evidence that rad54 alterations may be involved in carcinogenesis. Out of 132 primary tumors examined, several mutations in rad54 have been identified; these include a GGA→AGA (Gly→Arg) in a breast tumor, CCT→CAT (Pro→His) in a colon cancer, and GTG→GAG (Val→Glu) at codon 444 in a lymphoma (Matsuda, M. et al., 1999. *Oncogene*. 18:3427–30). The mutation in the colon cancer was clearly somatic in origin, as the surrounding tissue had the wild-type sequence. The observation that a rad54 mutation occurred in 1/24 lymphomas examined has an important implication for our proposed study, as it provides relevance for our work in lymphoblastoid cells.

The significance of the proposed work is that we will evaluate the effect of point mutations and rare point mutations actually found in the human populations sampled on mutation states in human cells. This emphases in phenotype evaluation and focus on DNA repair genes has been made in response to the reviewers' criticisms.

Studies

The studies proposed herein require a sensitivity of only $5 \times 10^{-5}$ to detect 5 or more inherited point mutants among 100,000 alleles. This sensitivity is possible because we use Pfu DNA polymerase under conditions in which PCR error is observed to be about $6 \times 10^{-7}$ errors per base incorporation and because we limit our initial PCR amplification to 5 doublings (André, P. et al., 1997. *Genome Research*. 7:843–852). This limits the background noise due to PCR to about $6 \times 10^{-7} \times 5 = 3 \times 10^{-6}$ mutations per base pair prior to separation of mutant from wild-type sequences. Detection on the capillary is accomplished using laser induced fluorescence from a fluorescein-labeled PCR primer that also serves as a high melting temperature "clamp" necessary for CDCE separation. Once we could detect low fractions of point mutants in simple reconstruction experiments we had to work out a method to process real human cells and tissues. Because mutant fractions were so low we had to start with cell numbers in excess of $10^9$ or more than 6 mg of genomic DNA.

The procedure we developed involves isolating the total DNA (up to 10 mg) by simply digesting with proteinase K, SDS and RNase followed by centrifugation and ethanol precipitation. This gives us >90% yield in a protocol with iterative extractions. We digest this mass of DNA with a pair of restriction enzymes, which liberates a fragment containing our desired sequences. We hybridize with an excess of biotin-labeled probes to both the Watson and Crick strands of the desired sequences. This allows us to capture the hybrids from the bulk DNA using streptavidin-coated glass beads with a particularly low affinity for non-specific DNA binding. These are then amplified using hifiPCR. A very important characteristic of this method is that it permits us to remove many thousands of DNA sequences from the same pooled samples since DNA removed from the bead washings are returned to the original sample.

Figures 22A, 22B:
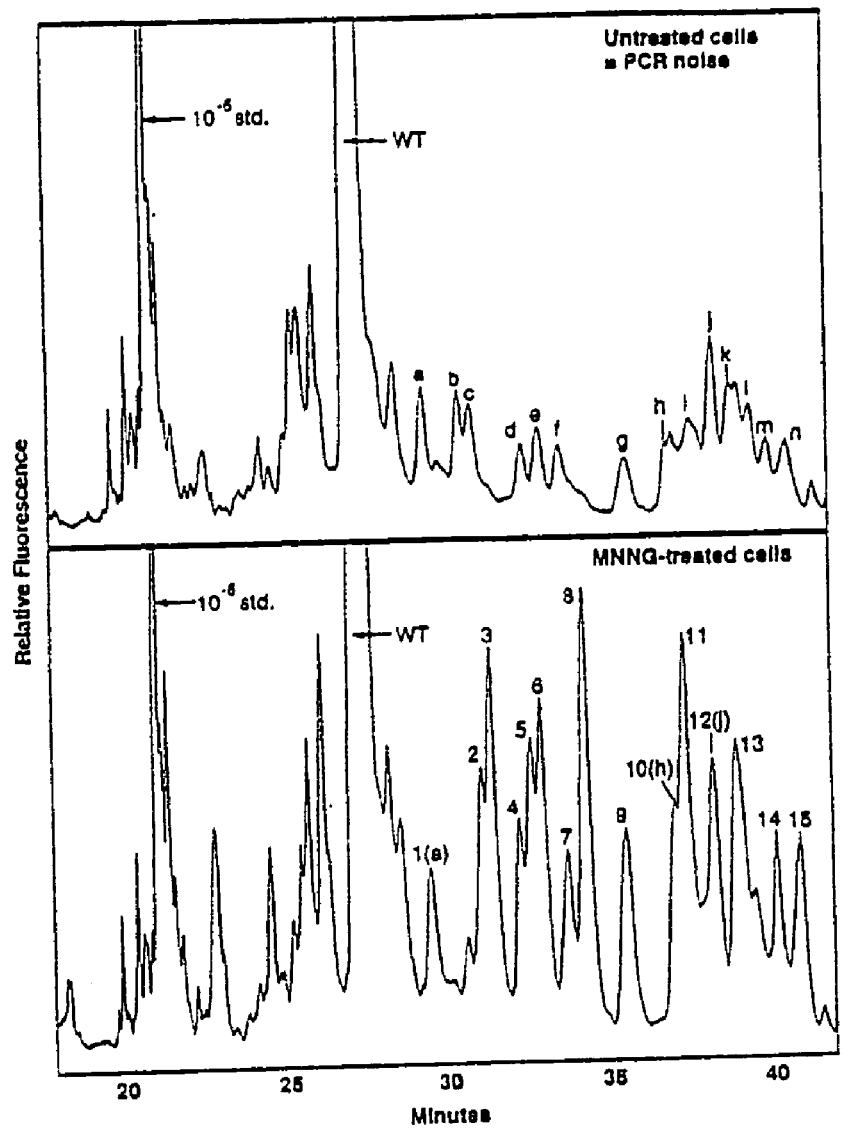
FIGS. 22A and 22B are electropherograms demonstrating the sensitivity of the method of detecting inherited point mutations. Constant denaturing capillary electrophoresis (CDCE) display of background (FIG. 22A) and MNNG-induced mutational spectra (FIG. 22B) in the APC gene in human MT1 cells. Each numbered and lettered peak is a single mutant sequence which has been isolated and sequenced. Top panel: mutants a–n are all G/C→T/A transversions arising from Pfu DNA polymerase error in the background. This constitutes the "noise" from PCR.
Figure 23A:
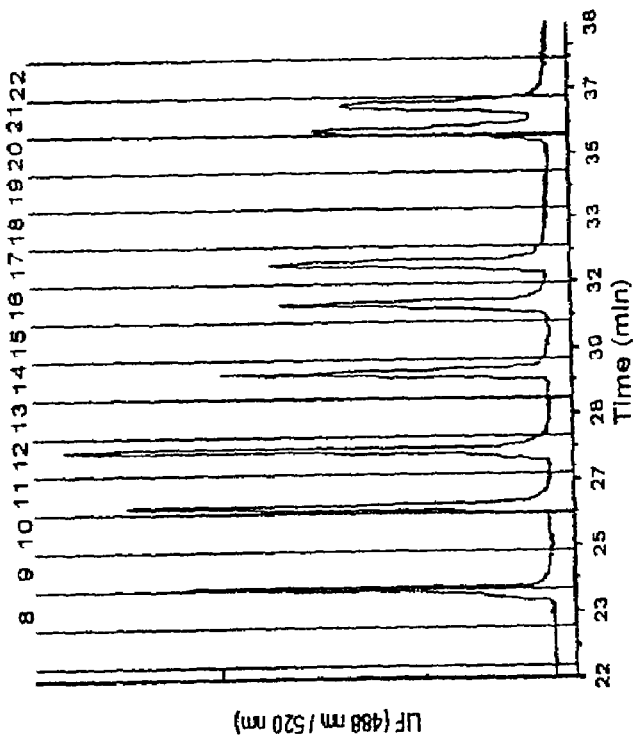
FIGS. 23A and 23B are electropherograms demonstrating the isolation of pBR322 HinfI restriction digest fragments using automated fraction collection.
Figure 23B:
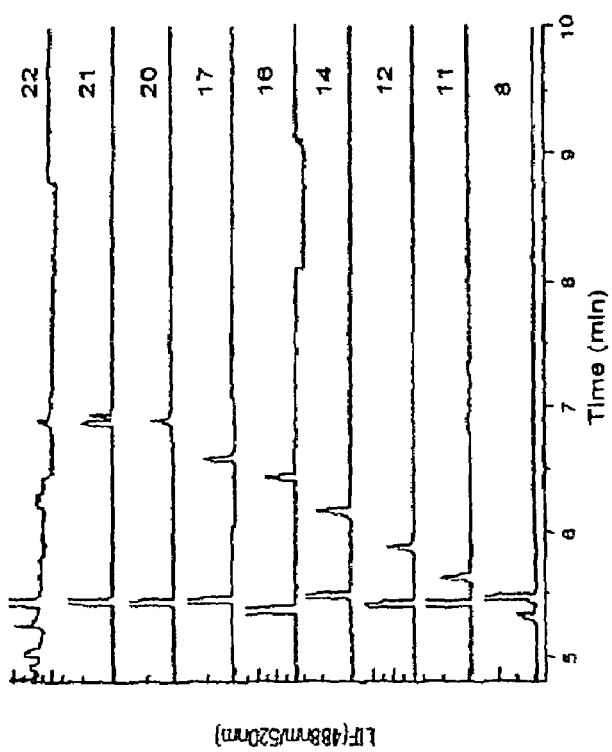

We recover more than 70% of our original copy number after elution from the streptavidin coated beads. The enrichment for a single copy nuclear gene was 10,000 fold as determined by comparison to carry over of multicopy mitochondrial sequences. The sequence we used for this development was a 255-bp sequence of the human APC gene, cDNA bp 8429–8683. It has served as an example of a nuclear sequence with juxtaposed high and low temperature isomelting domain. Mutations are detected in a 104 bp sequence between bp 8560 and 8663 in the low melting domain. Our current detection limit of these APC gene mutations in human cells and tissue samples is $10^{-6}$ (FIGS. 22A and 22B).

There are optimized procedures for controlled polymerization of linear polyacrylamide (Goetzinger, W. et al.; 1998. *Electrophoresis*. 19:242–248). Using emulsion polymerization, linear polyacrylamide (LPA) of defined chain length can be tailored for any type of DNA separation, and stored indefinitely in powdered form. For example, long chains (10 to 17 MDa or greater) alone and in combination with short chains (50 to 250 KDa) are advantageous for long DNA sequencing read lengths (Salas-Solano, O. et al., 1998. *Anal. Chem*. 70:3996–4003; Zhou, H. et al., 1999. Submitted.; Carrilho, E. et al., 1996. *Anal. Chem*. 68:3305–3313), while a medium size (~1 MDa) polymer is suitable for the separation of short (100–500 bp) dsDNA fragments (Berka, J. et al., 1995. *Electrophoresis*. 16:377–388). The capability to produce a variety of molecular masses of LPA will allow optimized compositions for the variety of tasks to be undertaken (e.g., PCR product analysis, CDCE, sequencing).

Mitochondrial Mutations.

We have also measured mutational spectra in the mitochondrial sequence bp 10,030 to 10,130 in multiple tissues, tumors, and human cells in culture. This task was substantially easier than the nuclear DNA studies described above because there were about 400 rather than two gene copies per cell and initial isolation of the desired sequence was not required. But these studies gave us substantial experience in handling DNA from human blood and organs. We discovered the same set of 17 mitochondrial hotspot mutations in all samples indicating a universal process of human mitochondrial point mutation. The mutations observed consisted primarily of both kinds of transition mutations with two transversions. A sensitivity limit of $10^{-6}$ was required for these observations. Mutations were demonstrated in both "Watson and Crick" strands, a necessary step to control for mismatch intermediates or DNA damage being mistaken for mutations (Khrapko, K. et al., 1997. *Nucl. Acids Res.* 25:685–693; Coller, H. et al., 1998. *Cancer Res.* 58:1268–1277). This research demonstrated our ability to determine rare mutations in which as many as 20 separate mutations were found in a single 100 bp target sequence. These studies establish the fact that point mutations in the human genome can be and have been detected, isolated and sequenced down to a frequency of $10^{-6}$.

Study of 1000 Pooled Blood Samples

We chose three approximately 100 bp sequences in the large exon 15 of the APC gene, one from exon 8 of the TP53 gene and six from exons 2,3,5,6,8 and 9 of the Hprt gene and one mitochondrial DNA sequence. We defined conditions for high fidelity PCR and CDCE separation. We also created internal standards for each sequence.

In our first trial, we collected two separate groups of blood samples from 1000 juveniles from the Boston Lead Laboratory. We created two separate pooled samples from each separate juvenile set. These four pooled samples, two independently constructed duplicate pooled samples from each of the two separate juvenile sets were assayed for the ten nuclear DNA sequences and one mitochondrial DNA sequence. The results are summarized in Table 1.

Of the nuclear sequences scanned six inherited point mutations were discovered and one was found in the mitochondrial sequence. Two high inherited mutant fractions were found in a sequence of the APC gene exon 15 (11%) and in the mitochondrial sequence (18%). Four separate mutations have been found but not yet sequenced in exon 9 of Hprt each with mutant fractions between $10^{-3}$ and $10^{-2}$. Since a total of 4000 alleles were scanned for the autosomal genes APC and TP53, the absence of any signal indicated that no inherited mutations were present in these samples at a level $2.5 \times 10^4$. Since the Hprt is X-linked some 3000 alleles were scanned in these mixed gender sets. One mutant in exon 3 of Hprt was later traced to persons of African-American heritage.

TABLE 7

Results of scanning ten nuclear and one mitochondrial 100 bp sequences for inherited point mutations by CDCE/hifiPCR in two separate pooled blood samples each derived from 1000 juveniles.

| Gene | Scanned sequence (position) | Allelic fraction |
|---|---|---|
| APC exon 15 | 121 bp (cDNA bp 8543–8663) | GC → TA at cDNA bp 8643 (11%) |
| APC exon 15 | 113 bp (cDNA bp 3876–3988) | None ($\geq 2.5 \times 10^{-4}$) |
| APC exon 15 | 109 bp (cDNA bp 4332–4440) | None ($\geq 2.5 \times 10^{-4}$) |
| TP53 exon 8 | 131 bp (bp 14461–144591) | None ($\geq 2.5 \times 10^{-4}$) |
| HPRT exon 2 | 72 bp (cDNA bp 34–105) | None ($\geq 3.3 \times 10^{-4}$) |
| HPRT exon 3 | 80 bp (cDNA bp 135–214) | None ($\geq 3.3 \times 10^{-4}$) |
| HPRT exon 5 | 66 bp (cDNA bp 385–402 + 9 bp 5' intron + 40 bp 3' intron) | None ($\geq 3.3 \times 10^{-4}$) |
| HPRT exon 6 | 112 bp (cDNA bp 403–485 + 3 bp 5' intron + 6 bp 3' intron) | GC → AT at cDNA bp 480 ($6 \times 10^{-3}$), only in African Americans |
| HPRT exon 8 | 96 bp (cDNA bp 538–609 + 23 bp 3' intron) | None ($\geq 3.3 \times 10^{-4}$) |
| HPRT exon 9 | 84 bp (cDNA bp 610–657 + 15 bp 3' intron + 21 bp 5' intron) | ≈4 as yet unidentified but confirmed point mutants each at 2 to 8 × $10^{-3}$ |
| Mitochondrial DNA | 100 bp (mitochondrial bp 10031–10130) | GC → AT at bp 10060 (18%) |

We regarded these first observations as important not only for the mutants observed but for the fraction of 100 bp sequences which did NOT contain inherited point mutations. 7 of 10 nuclear sequences were vacant with regard to inherited point mutations at fractions $3.3 \times 10^{-4}$. This was extremely significant since it indicated that the discovery of individual recessive deleterious alleles expected to arise at fractions from about $3 \times 10^{-3}$ and lower would not be impeded by the presence large number of non-deleterious alleles.

Figure 24:
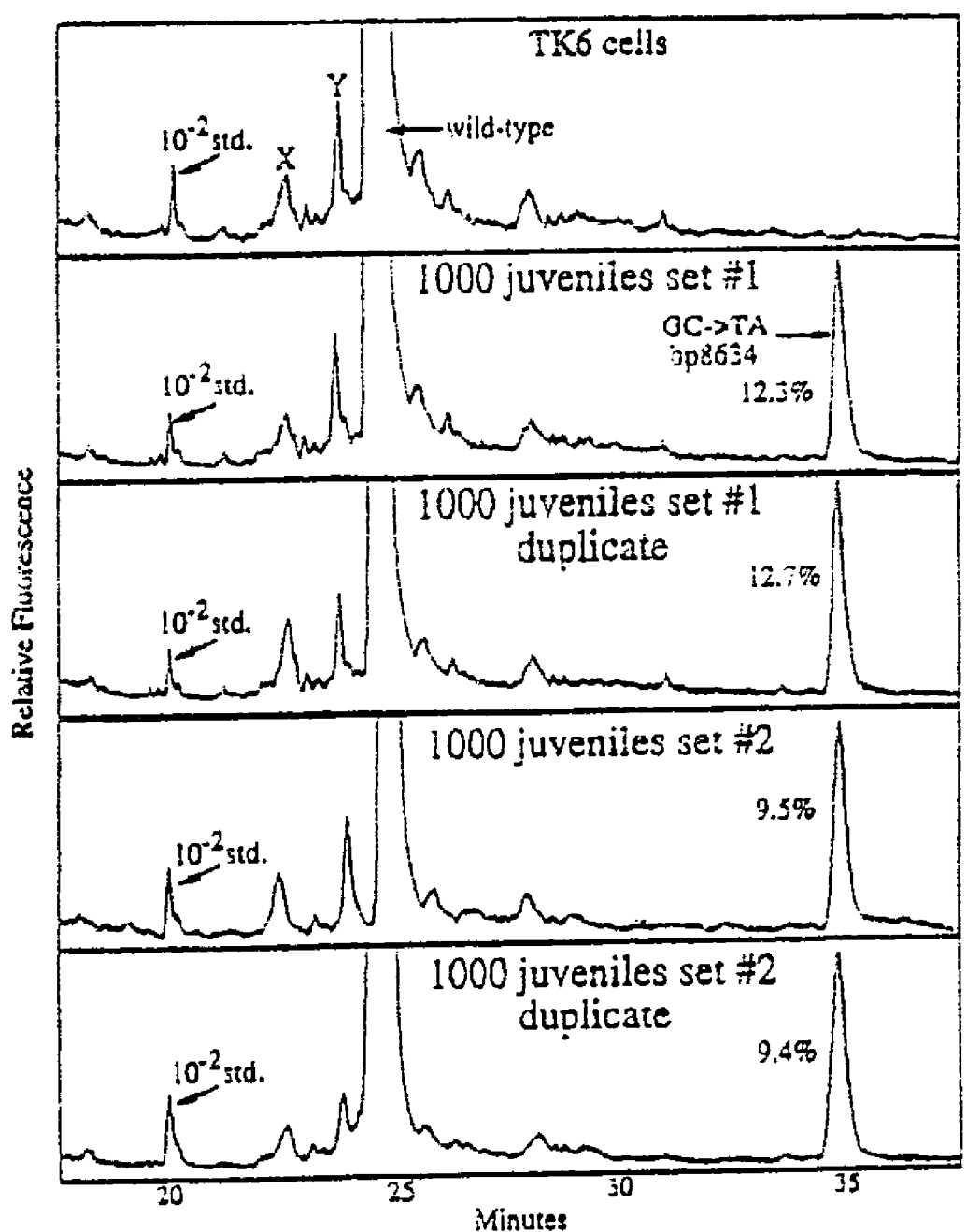
FIG. 24 is a series of electropherograms demonstrateing CDCE LIF output for runs of the four pooled samples used in Table 7. A sequence of the APC exon 15 is shown as an example. On the left one sees the PCR primers and the internal standard peak followed by the large wild-type peak and then the peak of the inherited point mutant. The mutation is a G→T transversion at bp 8634. In this form of sample presentation all sequences are in the homoduplex form so a mutant is present as a single peak of different melting temperature than the wild-type or internal standard. This demonstrates the reproducibility of the proposed assay for inherited point mutants and indicates the variation which may be expected among large samples drawn from the same community of mixed ethnicity (Boston).

In FIG. 24 we show the kind of reproducibility observed for all eleven sequences scanned using a sequence from exon 15 of the APC gene as an example. What is shown is a CDCE run in which the mutant sequences are run as homoduplexes just prior to peak isolation for sequencing. By the use of the internal standard introduced into the original sequence isolate, it was possible to obtain estimates of original mutant fractions.

In our first direct studies of potential ethnic differences with regard to rarer inherited point mutations we examined almost 1900 alleles of juveniles of African-American and Hispanic-American origin. These samples came from the New York Lead Laboratory. As may be seen in FIG. 24 an inherited mutation was found in the African-American group which was absent in the Hispanic-American group.

Sometimes our raw CDCE data creates confusion and reasonable reviewers want to see what we really see as we first amplify our genomic samples with fluorescent labeled clamp sequences as primers. The steps are shown in FIG. 24. First we check to be sure there is no significant PCR "noise" in the sample by amplifying DNA from the human TK6 cell through some 30 doublings.

Preliminary Data from MIT—Shanghai Cell Biology Institute Consortium.

The observations from the consortium supported the observation that the number of distinct point mutants in any 100 bp sequence which arose at fractions of either $>2.5 \times 10^{-4}$ or $>10^{-4}$ were "few and far between." This result is extremely important since it indicates that both non-deleterious and recessive deleterious alleles should be easily recognized in large pooled samples as proposed.

Pooled samples from 5000 Han Chinese juveniles or 10,000 alleles for autosomal genes were obtained. The sensitivity of the procedure is such that even a single point mutant sequence would be detected. In FIG. 27 the results for the beta globin gene are presented as the mutant fractions for the mutations observed plotted at their sequence positions in the genes. A similar quantitative distribution has been observed for the larger alpha-1-antichymotrypsin gene.

In a parallel effort some 41 STS were scanned as examples of sequences in which mutations would not be expected to effect reproductive fitness. These sequences had already been found by the MIT-Whitehead Institute genome center to contain point mutations at 25% or higher in the several dozens of individual genomes scanned. Using the pooled sample approach, an additional 21 point mutations (1% or higher) were found, but only three mutations in the frequency range from 0.01 to 0.001. These data extend the observations that the number of rare inherited point mutations is small.

Considerations were to:
Discover which genes have obligatory knockout alleles at fractions that permit inferences about the importance of such genes in determining reproductive fitness.
Identify and note the fraction of genes scanned which appear to carry either dominant or recessive deleterious alleles.

Some reports have express the belief that most mutations causing hereditary diseases are missense mutations. This is certainly true for sickle cell anemia and a variety of other disorders but our experience with APC and Hprt mutations led us to think that a significant fraction of recessive or dominant deleterious mutations would be frameshifts or stop codons. >5,000 recorded point mutations were studied and more than 40% were found to be of the obligatory knockout (OKO) variety. Here in Table 8 he summarizes the results for the genes with the most reported individual mutations. It is clear by inspection that OKOs are a general feature of inherited disease-causing mutations. Their presence in two or more separate knock out alleles each at fractions below 1% would permit an inference that the gene in question carries recessive deleterious alleles.

will be used as the test samples for CDCE optimization. The optimization will be performed using the same 24-capillary array CDCE instrument. Using the independent temperature control on each column, an 11° C. temperature range in increment of 1° C. which covers (Tm−6° C.) to (Tm+5° C.) will be tested in the first run. The optimum temperature will then be refined by a second multi-capillary run using temperature increments of 0.2° C. For those target sequences that a high resolution separation can not be achieved by varying the CDCE temperature, lower electric field strengths and/or a linear polyacrylamide matrix with increased salt concentrations will be used to improve the resolution (Khrapko, K. et al., 1996. *Electrophoresis.* 17:18671874).

Evaluation of the data to select the optimum temperature will be automated by software to make the required mea-

TABLE 8

Result of a study of genes and inherited mutations in the Human Genome Mutation Database to discover what fraction of inherited disease is attributable to obligatory knockout mutations (R. Wasserkort, MIT).

| genes | Total # of all kinds of mutations | Ratio OKO to all point Mutations | Gene name | Disease(s) |
|---|---|---|---|---|
| APC | 301 | 0.97 | Adenomatous polyposis coli | Adenomatous polyposis colis |
| BRCA1 | 258 | 0.82 | Breast cancer 1 | Breast cancer, ovarian cancer |
| CYBB | 182 | 0.65 | Cytochrome b-245, β-polypept. | Chronic granulomatous disease |
| BTK | 210 | 0.64 | Bruton agammaglobulinaemia tyrosine kinase | Agammaglobulinaemia |
| HBB | 259 | 0.54 | Haemoglobin beta | Thalassacmia beta, Haemoglobin variant |
| CTFR | 495 | 0.52 | Cystic fibrosis transmembrane conductance regulator | Cystic fibrosis, Congenital absence of vas deferens, Hypertrypsinaemia, low sweat chloride |
| IDS | 238 | 0.49 | Iduronate 2-sulphatase | Hunter syndrome |
| LDLR | 359 | 0.45 | Low density lipoprotein receptor | Hypercholesterolaemia |
| ALD | 123 | 0.43 | Adrenoleukodystrophy | Adrenoleukodystrophy |
| CollA1 | 123 | 0.37 | Collagen I alpha 1 | Osteogenesis imperfecta I–IV, Ehlers-Danlos syndr. VII |
| TYR | 83 | 0.36 | Tyrosinase | Albinism, oculocutaneous 1 |
| F9 | 637 | 0.36 | Factor IX | Haemophillia B, Warfarin sensitivity |
| OTC | 146 | 0.35 | Omithine carbamoyltrans-ferase | Omithine transcarbamylase deficiency, Hyperammonaemia |
| HPRT1 | 104 | 0.35 | Hypoxanthine phospho-ribosyltransferase 1 | Hypoxanthine guanine phosphoribosyltr. defic., Lesch-Nyan syndrome |
| PAH | 275 | 0.35 | Phenylalanine hydroxylase | Phenylketonuria, Hyperphenylalaninaemia |
| TP53 | 59 | 0.30 | Tumour protein p53 | Li-Fraumeni syndrome, Adrenocortical carcinoma |
| PKLR | 119 | 0.28 | Pyruvate kinase (liver and red blood cell) | Pyruvate kinase deficiency, Haemolytic anaemia |
| RHO | 88 | 0.14 | Rhodopsin | Retinitis pigmentosa, Nightblindness |
|  | 4059 | 0.46 | sum | arithm. mean |

Anticipated Optimization Studies

The following description of elements of a high throughput laboratory for point mutation discovery are offered as evidence that the teaching of this application can reasonably be anticipated to be accomplished for all or a large portion of genes in the human genome.

CDCE Optimization.

To ensure highest enrichment of mutant heteroduplexes as well as highest resolution for separation of mutant homoduplexes, CDCE conditions must be optimized for each target. The optimal CDCE conditions for collecting SNP-containing heteroduplexes should allow all of the heteroduplexes to coalesce into a single fraction well separated from the wild-type homoduplex, while the optimal conditions for isolating SNP-containing homoduplexes should provide the greatest resolution among the observed homoduplex peaks. The PCR products amplified under the optimized conditions surements of resolution and peak shape. PCR and CDCE optimization will be performed at MIT. The optimized conditions for each target sequence will be used for enrichment and isolation of SNPs and rare SNPs at the Karger laboratory.

Example 4

Research Design and Methods

Enrichment of Mutants

The target sequences amplified from the pooled genomic DNA sample by hifiPCR will be run on CDCE to separate the fast-migrating wild-type homoduplex from the slower-migrating mutant heteroduplexes at the optimal temperature. Point mutation-containing mutant heteroduplexes will be collected in a single fraction for each column and thus enriched relative to the wild-type sequence.

Quantitative enrichment of the mutant fraction in pooled genomic DNA is key to the ability of CDCE/hifiPCR to detect low-frequency mutations (Khrapko, K. et al., 1997. *Nucl. Acids Res.* 25:685–693). We will first quantify the copy number of the target sequence enriched from the pooled DNA sample containing 100,000 alleles by competitive PCR with the same two artificial mutants used for PCR and CDCE optimization. Based on the target copy number measured, the two mutants will be added at a mutant fraction of 0.05% to serve as internal standards. The mixed sample will be amplified 6 doublings (to minimize PCR noise), boiled and reannealed to form heteroduplexes, and run on the CDCE instrument to enrich the heteroduplexes.

In this case, two rows of a standard 96-well plate will be used for collection. During separation, the signal in each capillary will be monitored to detect the exit time of the wild-type DNA from the capillaries. This detection will be performed automatically, without need for manual attention. At the moment the program determines that the broadened tail section of the wild-type peak in a particular capillary has reached a given fraction of the peak maximum, the electric current in that capillary will be interrupted using computer controlled relays. Once the current to all capillaries has been stopped (zones will elute at different times in different capillaries and therefore the time of stoppage will differ for each of the columns), the capillary ends will be moved into the next row of the wells on the collection plate, and all the DNA fragments behind the wild-type zone will be collected. Diffusion of the DNA from the capillary during current stoppage is not a concern because this step will be fast (in seconds), and diffusion is minimized by the viscous sieving matrix.

Several iterations of hifiPCR and CDCE may be required to enrich and amplify the mutants sufficiently for the next stage which is isolation of individual mutants. The number of iterations will be determined by whether the peaks corresponding to the internal standards are visible in the CDCE data trace at a signal-to-noise ratio above a pre-defined threshold. To aid in automation, the decision of sufficient enrichment will be made by software based on the ABC expert system that was developed in the Karger laboratory (Northeastern University, Boston, Mass.) as a base caller for DNA sequencing. Sample handling will be done with a robotic workstation.

Isolation of Individual Mutants.

After heteroduplex enrichment, mutants must be isolated, quantitated, and sequenced. The combined mutant fraction from the previous step will be amplified using only a few cycles of PCR, so that excess primers will still be present in the final reactions, preventing the formation of heteroduplexes. The resultant mutant homoduplexes will then be isolated by CDCE with fraction collection into the multiwell gel plate (again at the previously determined optimum temperature). As mentioned previously, the location of the fractions on the collection plate will be automatically correlated with the detection signal from the LIF detector. The frequency of a mutant in the original sample will be measured by comparing the peak area of the mutant with the peak areas of the internal standards added in the first CDCE step. Despite the high resolving power of CDCE, there will undoubtedly be samples where more than one mutant homoduplex will comigrate. Large homoduplex peaks will be tested for buried peaks by melting and reannealing followed by CDCE. The presence of multiple peaks under CDCE will reveal any previously hidden mutant.

In the CDCE multicapillary operation, manipulation of the collected fractions will be performed with the robot, and the separation matrix will be replaced after each run. Since both the injection and collection ends of the capillary array must be free, the standard mode of the matrix replacement in DNA sequencing (port permanently connected to the detection end of the capillaries) cannot be applied. At the start of the research project, the matrix will be manually replaced by a syringe equipped with a Teflon joint. At a later stage, a microfabricated matrix replacement port, for automated matrix replacement in all capillaries will be incorporated. This device will replace the matrix from the center of each capillary in the array using a liquid junction. Software to automate data analysis for the fraction-collecting instrument will be developed. The program will aid the operator in using the fluorescence traces from the two detection windows on the capillary array to locate rapidly the collected fractions containing particular peaks. The program will also generate reports with the trace profiles. In the first year of the proposed work, this software will be supplemented by a fully automated procedure to align the traces from the two detection windows using either cross-correlation or dynamic time-warping (Malmquist, G. and Danielsson, R., 1994. *J. Chromatog.* A687:71–88; Nielsen, N.-P. et al., 1999. *Anal. Chem.* 71:727–735) followed by peak detection (Dyson, N., 1990. Chromatographic integration methods. The Bath Press, Bath, U.K.).

Sequencing of Isolated Mutants.

After the final CDCE step, the mutants from the multi-well agarose gel plate will be automatically pipetted to a robotic workstation with an embedded thermocycler for cycle sequencing. Since only short stretches of DNA (<1000 bp) will be sequenced, desalting will not be used as a clean-up step. The samples will simply be diluted ten-fold with water and electrokinetically injected. We will construct an automated capillary array sequencer with column lengths of ~20 cm each, since only 100–200 bases will need to be sequenced. The instrument will be similar to one already built for de novo long read sequencing using a 48 capillary array. It will incorporate a line generator with a Powell lens to make uniform illumination of all capillaries. Detection will use a CCD camera. This instrument can be easily expanded to a greater number of capillaries, as required. The instrument will be dedicated for the many sequences to be determined in this project.

The sequencing strategy will employ energy transfer dye terminator chemistry. Each isolated mutant will be amplified and both strands sequenced. For one strand, a primer will be used to anneal to a section of the high melting domain (clamp) sequence. For the other strand, the primer used in hifiPCR will be employed. Along with sequencing of mutant strands, appropriate controls will be employed including periodic sequencing of standard DNA sequences. Base calling will be performed using the ABC expert system developed for human genome sequencing (Miller, A. and Karger, B. 1999. In preparation). Enrichment, isolation and sequencing of mutants will be performed at Northeastern University.

Software and Informatics.

Custom software that will be needed for automating data acquisition, instrument control and electrophoretic data analysis. Additional software will be needed to coordinate laboratory activities, to centralize information, and to make the results of the project accessible. It will be essential to track and coordinate activities for the thousands of PCRs, CDCE electropherograms, pooled fractions, and DNA sequencing samples generated over the course of the work.

Initially, inexpensive commercial databases and internet development tools will be used for these functions, though ultimately a commercial laboratory information management system (LIMS) may be required if one were to examine a much larger number of genes. Development and maintenance of the data systems to be developed will be essential throughout the whole of the project as the amount of data multiplies and the variety of analyses increases.

The mutation information emerging from the proposed work will constitute a valuable database, containing both sequence information and extensive annotations, following the model of other genetic databases (Brown, S. 1999. *BioTechniques*. 26:1090–1094). Existing public repositories (Burks, C. 1999. *Nucl. Acids Res.* 27:1–9) can also be leveraged as their number and contents burgeon over the next few years. These resources will include a very substantial volume of information on point mutations obtained by the described methods, which will be used to cross-validate our results. Even outside of mutation databases, sequence databases can be used to detect mutations for this purpose by finding mismatches in overlapping sequences derived from different genetic lineages (Taillon-Miller, P. et al., 1998. *Genome Res.* 8:748–754; Picoult-Newberg, L. et al., 1999. *Genome Res.* 9:167–174). An additional use of the databases will be routine surveillance to identify additional genes involved in DNA replication, repair and recombination, and to update information on known genes. This database work will be accomplished primarily with sequence analysis and data mining software already in the public domain (Altschul, S. et al., 1997. *Nucl. Acids Res.* 25:3389–3402; Pruitt, K., 1998. *Genome Res.* 8:1000–1004; Kuehl, P. et al., 1999. *Genome Res.* 9189–194).

Samples

Collect blood samples from a large number of juvenile Americans. Our first large sample will use all intact samples from a large New York City children's lead testing laboratory plus a set already collected in Boston. From this and a series of other lead testing laboratories we expect to get a sufficiently large number of samples from major ethnic groups to allow creation of separate pooled samples. We expect that studies of these different groups will carry a number of idiosyncratic point mutations which will increase the number of obligatory knockout mutations observed and permit more conclusive determination as to whether a gene carries recessive or dominant deleterious alleles.

The comparison of different ethnic groups is expected to increase the number of different inherited alleles observed for each gene. For instance, we expect to observe different sets of recessive deleterious alleles for genes which have come to Hardy-Weinberg equilibria in Asian populations as opposed to African populations. Some alleles may be identical but several in a set of six to ten are expected to vary.

Selection of Genes and Defining Target Sequences in Initial Studies.

We have been interested in the mutations created during the DNA repair processes for a number of years and have a special interest in determining the kinds of SNPs present in genes that are involved in human DNA repair. We propose to initially examine a set of genes known to be involved in DNA repair and recombination. One would imagine that such genes are essential. They might carry dominant deleterious alleles, but, if not, they must carry recessive deleterious alleles. Findings of any evidence of inherited non-deleterious variation in these alleles could be of value in understanding variations among humans with regard to mutation rates. Together they offer a look at a multigenic set of factors which could disrupt or alter primary physiologic processes, DNA repair and recombination.

We have selected 13 genes that are essential for mismatch, base excision and nucleotide excision repair as well as DNA recombination (Table 9; Sancar, A., 1995. *Annu. Rev. Genet.* 29:69–105; Nelson et al. (1996); Acharya et al. (1996); Plug et al.(1997); Iaccarino, I. et al., 1998. *EMBO J.* 17:2677–86; Jeggo, P., 1998. *Adv. Genet.* 38:185–2189; Kolodner, R. and Marsischky, G., 1999. *Curr. Opin. Genet. Dev.* 9:89–96; Arbel, A. et al., 1999. *EMBO J.* 18:2648–2658; Zhong, Q. et al., 1999. *Science.* 285:747–50). cDNAs have been determined for each of these and the complete sequences for all selected genes permitting us to define the exons and splice sites are expected during 2000 when much of the human genome sequencing efforts will be completed.

As an internal control for detection of non-deleterious and recessive deleterious alleles we propose to study two housekeeping genes, Alpha-1-antichymotrypsin (AACT) and Adenine Phosphoribosyltransferase (APRT), respectively, both of which are no involved in either DNA repair or recombination. AA CT is a plasma protease inhibitor synthesized in the liver and the disorders caused by mutations in this gene are inherited in an autosomal dominant manner. Several polymorphisms of this gene have been described and the carriers of such polymorphisms show increased susceptibility to Alzheimer's disease (Kamboh, M. et al., 1995. *Nat. Genet.* 10:486–488) or Parkinson disease (Yamamoto, M. et al., 1997. *Brain Res.* 759:153–155). The APRT gene will be studied as a control gene believed to carry only non-deleterious alleles. Patients with complete deficiency of APRT excrete gravel consisting of stones of 2,8-dihydroxyadenine (DHA) in urine, but do not have hyperuricemia or gout. Already nine allelic variants of the APRT gene are known (see APRT entrants in the OMIM database).

We will determine the melting maps (example shown in FIG. 29) and restriction maps for all 15 genes listed in Table 3. This process defines the target sequences including coding sequences and adjacent splice sites in terms of a set of approximately 100 bp "isomelting domains" bounded by suitable restriction sites. Approximately 98% of the human genome is assayable by this approach as estimated by computer scanning of 0.5 megabases by melting temperature calculations. Restriction enzymes, sequences of biotinylated probes and PCR primers will then be determined and tested.

TABLE 9

List of genes to be studied. This list is only a subset of all genes that are involved in DNA repair and recombination. A list with virtually all genes that are presently known (or suspected) to be involved in DNA repair and recombination has been assembled and contains more than 100 entries. A subset had to be selected as the study of all of these genes is not feasible within the framework of this proposal. The other genes, however, remain of interest for future work.

| Gene Symbol | Name/ definition | Chromos. location | Genbank access # | Complete sequence | cDNA length (bp) |
|---|---|---|---|---|---|
| Gene Involved in DNA Repair and/or Recombination | | | | | |
| APE | AP endonuclease | 14q12 | D13370 | yes | 1021 |
| ATM | Ataxia telangiectasia | 11q22.3 | U33841 | yes | 9385 |
| BRCA1 | Breast cancer, type 1 | 17q21 | L78833 | yes | 5580 |
| ERCC2 | excision repair, complementation group 2 | 19q13.3 | L47234 | yes | 2247 |

TABLE 9-continued

List of genes to be studied. This list is only a subset of all genes that are involved in DNA repair and recombination. A list with virtually all genes that are presently known (or suspected) to be involved in DNA repair and recombination has been assembled and contains more than 100 entries. A subset had to be selected as the study of all of these genes is not feasible within the framework of this proposal. The other genes, however, remain of interest for future work.

| Gene Symbol | Name/ definition | Chromos. location | Genbank access # | Complete sequence | cDNA length (bp) |
|---|---|---|---|---|---|
| HEX1 | exonuclease 1 | 1q43 | AF042282 | yes | 2411 |
| MPG | N-Methyl-purine DNA glycosylase | 16p13.3 | NM_002434 | no | 1108 |
| MSH2 | DNA mismatch repair protein | 2p21 | U03911 | no | 3080 |
| MSH6 | G/T mismatch binding protein (GTBP) | 2p21 | U28946 | no | 4264 |
| POLB | DNA polymerase beta | 8p12-p11 | D29013 | no | 1259 |
| RAD54L | helicase II (RAD54 like) | 1p32 | X97795 | no | 2607 |
| UNG | uracil-DNA glycosylase | 12q23-q24.1 | X89398 | yes | 973 |
| XPA | XPAC protein, xeroderma pigmentosum, complementation group A | 9q22.32 | D14533 | no | 1377 |
| XPC | XP-C repair complementing protein (p125) | 3p25.1 | D21089 | no | 3558 |
| Control Gene not Involved in DNA Repair or Recombination | | | | | |
| AACT | alpha-1-antichymotrypsin | 14q32.11 | K01500 | yes | 1324 |
| APRT | adenine phosphoribosyl-transferase | 16q24.3 | M16446 | yes | 538 |

Creation of Pooled Samples.

We will receive heparinized blood samples of about 2 or more ml which have been stored frozen since sampling for lead determination. We will thaw each sample rapidly, pipette rigorously to mix each sample, place 0.25 mL samples in each of two separate tubes and place the remainder up to 2 mL in −135° C. freezer vials which will be immediately returned to storage. Thus each individual blood sample will be maintained separately for any important future use, testing linkage hypotheses, for instance. Since we extract DNA from whole blood, the total white blood cell (WBC) count is the relevant parameter to consider variations from sample to sample.

The automated hematology reference ranges (95% confidence limits) from the MIT Medical Department Laboratory are 4.8–10.8 million WBC/mL with a mode of about 8 million WBC/mL for pediatric samples. Thus the average number of WBC/mL in five separate samples will be close to $8 \times 10^6$. At our limit of detection of 5 identical mutant alleles per 100,000 sampled alleles, it appears we may reasonably neglect variation due to the average number of WBC per five donors in estimating allele frequency. No conclusion in this work would be based on attempting to differentiate an allele fraction of 5/100,000 from 10/100,000.

The two 0.25 mL whole blood aliquots each contains approximately 2,000,000 WBC or about four million alleles for autosomal genes. We will pool 1000 blood samples simultaneously to create two independent duplicate pooled blood samples containing 2000 alleles each. Blood samples belonging to the same ethnic group will be pooled together. A total of 50 such pooled samples each in duplicate will thus be created from the 50,000 blood samples. Each pooled sample will contain about $2 \times 10^9$ WBC.

We will extract genomic DNA from the duplicated 50 samples pooled from 1000 donors each, using a modified genomic DNA isolation protocol without exposing DNA to either phenol or anion-exchange resins (Khrapko, K. et al., 1997. *Nucl. Acids Res.* 25:685–693). The blood cells will be precipitated and washed by centrifugation and resuspension in TE buffer (50 mM Tris-HCl, pH 8.0, 10 mM EDTA). The genomic DNA will be isolated from the blood cells through digestion with proteinase K (1 mg/mL) and SDS (0.5%) at 50° C. for 3 hours, RNaseA (0.1 mg/ml) at 37° C. for 1 hour, and then centrifugation and ethanol precipitation. This protocol usually provides a greater than 90% yield of genomic DNA from $10^5$ to $10^9$ cultured cells or milligrams to grams of tissues (Khrapko, K. et al., 1997. *Nucl. Acids Res.* 25:685–693; Li-Sucholeiki, X.-C. et al., 1999. *Electrophoresis.* 20:1224–1232). The UV absorption ratio of A260/A280 is typically 1.5–1.8. The isolated genomic DNA can be readily digested by restriction endonucleases. These genomic DNA samples will be held separately at −135° C. to create subsamples as required. This will allow us to have sets of samples from each ethnic group and sets of unknown ethnic origin. Aliquots of the 50 genomic DNA samples each in duplicate will be pooled to create the final Master pooled DNA sample containing 100,000 alleles. Sample pooling and DNA isolation will be performed at MIT.

Defining Unit Processes for Individual Target Sequences.

In this initial study of 15 genes we anticipate that as many as 150 target sequences each consisting of ~100 bps will be processed.

We will optimize the high-fidelity PCR and CDCE conditions for each target sequence using the automated 24-capillary array CDCE instrument and a temperature gradient thermocycler in a 96-well plate coupled with a robotic workstation for pipetting. The defined conditions will be integrated into the automated unit processes for high-throughput enrichment and isolation of SNPs and rare SNPs in the 15 genes.

PCR optimization will be done in three stages as previously described. In the first stage, we will apply our standard hifiPCR conditions to all of the target sequences. The only PCR parameter to be adjusted for each target sequence at this stage is the reannealing temperature which will be set at about 5° C. lower than the melting temperature of individual primer pairs. For target sequences which can be amplified with a high efficiency (50% per cycle) and low levels of nonspecific amplification and byproducts (<1% of the desired products), we will immediately proceed to CDCE optimization.

The standard hifiPCR will be performed in 20–30 $\mu$L using native *Pyrococcus furiosus* (Pfu) DNA polymerase with an associated 3'→5' exonuclease activity and the temperature gradient thermocycler in a 96-well plate. About 50 ng of genomic DNA isolated from TK6 cells will be mixed with the two artificial mutants for each target sequence at a mutant fraction above 10%, which will be used as the template. The standard PCR mixture will contain 20 mM Tris-HCl (pH 8.0), 2 mM $MgCl_2$, 10 mM KCl, 6 mM $(NH_4)_2SO_4$, 0.1% Triton X-100, 0.1 mg/mL BSA, 0.1 mM dNTPs, 0.2 M each primer, 0.1 U/$\mu$L Pfu DNA polymerase.

The target sequences which do not have acceptable PCR products in the first stage will be subjected to the second stage of optimization. In this stage, different reannealing temperatures and reannealing times will be tested to improve the efficiency or specificity of PCR. Some sequences may have a high level of PCR byproducts which consist of incomplete or exonucleolytically processed products missing one to several nucleotides. The formation of these byproducts is usually sequence-dependent and associated with the properties of the polymerase. Our past experiences have shown that the majority of these byproducts can be significantly reduced by incubating the final PCR products at 45° C. for 15 minutes or with a small amount of fresh Pfu DNA polymerase at 72° C. for 10 minutes (Khrapko, K. et al., 1997. *Nucl. Acids Res.* 25:685–693; Li-Sucholeiki, X.-C. et al., 1999. *Electrophoresis.* 20:1224–1232).

In our preliminary point mutation studies, we have successfully amplified all of the 11 target sequences under the standard PCR conditions, after adjusting for the temperature and time of reannealing or including a post-PCR incubation step. We thus expect that the optimal PCR conditions will be determined for the majority of the 150 target at this stage. For the remaining target sequences that do not work, we will proceed to the third step of optimization. This step will involve changing the components of the PCR mixtures, such as the concentrations of the magnesium, dNTPs and/or the primers. Finally, if this fails, we will redesign the primers and repeat the optimization process. Software for data evaluation will be developed in the Karger laboratory during the first year to aid in rapid semi-automated evaluation of the PCR product peaks on CDCE. This software will accelerate the PCR optimization process, particularly for the second and third stages.

The CDCE conditions for each target sequences will be optimized using the 24-capillary array CDCE instrument as previously described. The optimal CDCE conditions for collecting point mutation-containing heteroduplexes should allow all of the heteroduplexes to coalesce into a single fraction well separated from the wild-type homoduplex, while the optimal conditions for isolating point mutation-containing homoduplexes should provide the greatest resolution among the observed homoduplex peaks. These optimal conditions will be determined by first running the test samples at various separation temperatures and then by lowering the electric field strength and/or using a linear polyacrylamide matrix with high salt concentrations (Khrapko, K. et al., 1996. *Electrophoresis.* 17:1867–1874). While lowering the field strength will increase the separation time, this will not be a concern since those sequences required a lower field strength can be processed together using the 12-capillary array CDCE instrument connected to an automated fraction collection system. Evaluation of the data to select the optimum temperature will be automated by software to make the required measurements of resolution and peak shape.

Isolation of Individual Target Sequences from the Pooled DNA Sample.

A number of cell equivalent of 1000 cells per donor sample in a pooled sample will be required for point mutation analysis of each target sequence to remove any significant variation due to cell number. Thus the number of total WBC in the pooled sample containing 50,000 donors would be $5 \times 10^7$ cells which is equivalent to 300 g of genomic DNA. Such large amount of genomic DNA can not be directly subjected to a routine hifiPCR procedure. Furthermore, we will only pool $2 \times 10^6$ WBC (or 0.25 mL of blood) from each donor at this point. Thus one could think of our pooled blood samples containing material to study only 2000 DNA sequences or about 20 genes, which are certainly not enough for the proposed set of genes plus future point mutation identifications.

To overcome these problems, we will enrich individual target sequences from the pooled genomic DNA sample using our recently developed technology based on sequence-specific hybridization coupled with biotin-streptavidin capture systems (Li-Sucholeiki, X.-C. et al., 1999. *Electrophoresis.* 20:1224–1232). This enrichment step can not only significantly reduce the DNA sample size permitting the subsequent PCR, but also allow us to isolate multiple target sequences from the same genomic DNA sample, thus greatly increasing the number of sequences that can be studied.

In this approach, the pooled genomic DNA sample is first digested with suitable restriction endonucleases to release the DNA fragment containing the target sequence. The digested DNA is then hybridized simultaneously to excess biotin-labeled oligo DNA probes complementary to the Watson and Crick strands of the target sequence which is embedded in the restriction fragment. The hybrids are then captured by streptavidin-coated microspheric beads. Alternatively, the hybridization can be done with biotinylated probes pre-immobilized on the streptavidin-coated beads. In either case, the hybrid-bound beads are separated from the bulk DNA solution by centrifugation or by applying a magnetic field if the beads have paramagnetic properties. The beads are washed under stringent conditions to remove nonspecific binding. The washings are combined with the bulk DNA solution. The probe-bound target sequence is eluted from the beads into deionized $H_2O$ by heating. The elution can be directly amplified by hifiPCR. We have applied this method to enriching a digested APC gene fragment. A 10,000-fold enrichment and over 70% recovery was achieved for this target sequence (Li-Sucholeiki, X.-C. et al., 1999. *Electrophoresis.* 20:1224–1232).

To enrich multiple target sequences from the same genomic DNA sample, different types of streptavidin-coated beads, each containing a separate pair of probes for a different target sequence, will be used to hybridize simultaneously with the genomic DNA in the same reaction. After hybridization the different types of beads will be separated from the DNA solution and then from each other. After washing, individual target sequences will be separately eluted from each type of beads. This procedure can be repeated for the same bulk DNA solution to enrich another set of target sequences. We have demonstrated the use of paramagnetic beads and non-magnetic beads together to enrich four different target sequences from the same genomic DNA sample (Li-Sucholeiki et al., unpublished data).

The strategy for restriction digestion of the pooled genomic DNA sample at this point is to choose a "6-cutter" restriction endonuclease to reduce the high molecular weight genomic DNA into a reproducible set of fragments averaging about 4000 bp in length. While theoretically we could choose any 6-cutter, such a step may cut a desired sequence. We need 140 bp intact to amplify any desired 100 bp sequence after restriction digestion. By chance any 140 bp sequence will be cut in 140/4096=3.4% of the time. But Murphy's Law predicts that some very important sequence will eventually be found to be destroyed no matter what 6-cutter is chosen. Thus we will use two separate 6-cutters on the two Master Aliquot samples and process them in parallel thereafter. The chance that both endonucleases would cut a particular 140 bp sequence is only 0.001168.

Based on our preliminary results, we can in principle isolate up to 1000 separate sequences from each Master Aliquot containing an average of 1000 cells from each donor. Thus the average $2\times10^6$ WBC obtained from each donor would permit study of up to 2 million separate 100-bp sequences or as many as 100,000 genes. Isolation of individual target sequences will be performed at MIT.

Limited Amplification, Attachment of Clamp and Fluorescein Label.

The target sequence in the target-enriched sample will be amplified by high-fidelity PCR using Pfu polymerase and primers flanking the target sequence. One primer is simply 20 bp in length. The other primer is consisted of 60 base pairs including a 20 bp target specific sequence and a 40 bp non-monotonous GC sequence. This primer is labeled 5' with a fluorescein molecule. Thus the PCR product molecules will contain the desired 100 bp target sequence in a double stranded molecule with a contiguous high melting temperature domain or "clamp" which is necessary for achieving separation on the basis of differences in melting temperatures in the desired low melting domain. The fluorescein tag permits measurement of the number of molecules in a CDCE peak using laser induced fluorescence detection.

Because PCR, even with our high fidelity conditions using Pfu DNA polymerase, creates mutations in the product molecules, care must be taken that these PCR created mutants do not interfere with the observation and enumeration of point mutation-containing sequences. The PCR induced mutant fraction, PCRmf, is the product of the number of PCR doublings, d, the number of base pairs in the target sequence, b, and the error rate in terms of mutations per base pair per doubling, f (Keohavong and Thilly, 1988).

$$PCRmf = b \times f \times d$$

For Pfu DNA polymerase under our conditions $f=6\times10^{-7}$, and our target sequence is 100 bp. Thus if we amplified some 64× or 6 doublings (approximately 9 cycles), we would expect that (100) $(6\times10^{-7})$ (6)=$36\times10^{-5}$ of the products would contain PCR induced mutations. These Pfu-induced mutations are generally distributed over 10 distinct hotspot mutations each with a mutant fraction of about $3.6\times10^{-5}$ after 6 doublings as proposed (André, P. et al., 1997. *Genome Research.* 7:843–852). Since even a single specific SNP in 100,000 alleles would have a mutant fraction of $5\times10^{-5}$, it would be observed as a clear peak separate from the PCR "noise." A point mutation present in 0.1% of all persons would be represented 10 times and produce a mutant fraction of $50\times10^{-5}$ "towering" over any PCR noise.

For an accurate quantification of the allelic fractions of the SNPs and particularly the rare point mutations, we will introduce the two artificial mutants into the target-enriched sample prior to PCR at a known mutant fraction of $5\times10^{-4}$ to serve as internal standards (Khrapko, K. et al., 1997. *Nucl. Acids Res.* 25:685–693). The first hifiPCR step with 6 doublings will create $6\times10^9$ copies (=60×100,000 alleles×1000 copies/allele) of fluorescently labeled target sequences. The PCR sample will be boiled and reannealed to convert all point mutation-containing mutant sequences into mutant/wild-type heteroduplexes. This hifiPCR step will be performed at MIT.

Identification of Point Mutations and Rare Point Mutations Using Automated Unit processes.

Some 10% of the PCR product sample (about $6\times10^8$ copies) will be separated on CDCE at a suitable condition, and the heterodplexes will be collected in a single fraction separate from the wild-type homoduplex. We expect that this first CDCE collection will enrich the mutants 20-fold against the wild-type sequences. The heteroduplex fraction will be amplified by hifiPCR. A second heteroduplex collection by CDCE and hifiPCR will be performed to further enrich the mutants by about 5-fold. After the above procedures, rare point mutations at an initial allelic fraction of $5\times10^{-5}$ will be present at $5\times10^{-3}$ in the PCR products, which can be visualized on CDCE. The initial allelic fraction of a SNP can be determined by comparison to the internal standard (Khrapko, K. et al., 1997. *Nucl. Acids Res.* 25:685–693). Individual SNP-containing peaks will be isolated, amplified to create large numbers of labeled molecules, checked for homogeneity (little peaks hidden under big peaks), and finally, sequenced.

Enrichment and isolation of mutants will be performed with the 12-capillary array CDCE instrument equipped with automated fraction collection for each column which in turn interfaces with an automated collection transferring system for hifiPCR. The temperature for each column will be set at the optimized condition pre-determined for each target sequence. This system, which allows 12 different target sequences to be processed simultaneously, is essential for our high throughput. Sequencing of the isolated mutants will be done using the 8-capillary array CE instrument.

Tests for Bias.

We re-emphasize here that any and all rare point mutations identified in any pooled samples will be re-assayed using separated Watson and Crick strands. This is necessary in any assay for low frequency mutations since they may arise from mismatch intermediates in cells undergoing DNA synthesis at the time of sampling or as DNA damaged sites which were converted into mutations during PCR. These kinds of errors produce asymmetric distributions of apparent mutation on opposite DNA strands at the same position. True mutations produce symmetrical and complementing mutations. We introduced this control step in our studies of mitochondrial mutation and found two examples attributable to mismatch intermediates in rapidly growing cells in culture (Khrapko, K. et al., 1997. *Nucl. Acids Res.* 25:685–693). To the best of our knowledge the use of this essential control step is unique to our laboratory.

Considerations were to:

Discover which genes have obligatory knockout alleles at fractions that indicate the importance of such genes in determining reproductive fitness.

Identify and note the fraction of genes scanned which appear to carry either dominant or recessive deleterious alleles.

Our expectation is that if a gene carries only non-deleterious alleles, there will be some obligatory knockout alleles in the set of inherited mutations with allelic fractions greater than 1% with a sum of about 10%. If a gene carries recessive deleterious alleles we expect to see the sum of obligatory knockout alleles to be around 0.7% or so. If a gene carries dominant deleterious alleles we expect to see no obligatory knockout alleles in any ethnic group with an allelic fraction as high as 5/100,000 our limit of detection.

The determination of a reproducible fine map as proposed will mean different things to different scientists. It will give the first quantitative distribution of rare inherited alleles. It will provide some indication of which genes in the DNA replication complex carry dominant or recessive deleterious alleles. The observation of missense mutations in these genes may suggest that they could be involved in mutator syndromes which increase the spontaneous rate of somatic mutation. Such conditions would be expected to hasten the appearance of cancer or atherosclerosis, i.e., they would be harmful alleles.

We will create a readily accessible web file of our data as we obtain them as well as submitting observations for publications in reviewed journals. Our data set will include links to structural information as well as genomic sequences for each gene.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for identifying genes that carry one or more alleles that confer an increased likelihood of mortal disease, comprising
   a) determining the number of two or more detectable point mutations in a gene or gene segment in a population of young individuals, and calculating the sum of the frequencies of all point mutations determined for each gene or segment;
   b) determining the number of two or more detectable point mutations in a gene or gene segment in a population of aged individuals and calculating the sum of the frequencies of the point mutations determined for each gene or segment;
   c) comparing the sum of the frequencies of point mutations that are found in a selected gene or portion thereof of the young population calculated in a) with the sum of the frequencies of point mutations that are found in the same gene or portion thereof of the aged population calculated in b),
wherein a statistically significant decrease in the sum of the frequencies of point mutations associated with a particular gene in the aged population indicates that said selected gene carries one or more alleles that confer an increased likelihood of mortal disease.

2. A method for identifying genes that carry one or more alleles with an increased likelihood of being harmful, comprising:
   a) identifying the set of point mutations that are found in one or more genes or portions thereof of a population of young individuals, wherein the set comprises all detectable point mutations occurring at a frequency at about or above $5 \times 10^{-5}$ in a population from which the sample was obtained, and determining the frequency with which each point mutation occurs;
   b) identifying the detectable set of point mutations that are found in the genes or portions thereof of a population of aged individuals, and deter the frequency with which each point mutation occurs; and
   c) comparing the frequency of each point mutation identified in a selected gene or portion thereof of the young population determined in a) with the frequency of the same point mutations identified in said selected gene of the aged population determined in b),
wherein a significant decrease in the frequency of two or more point mutations in said selected gene of the aged population relative to said selected gene of the young population indicates that said selected gene carries one or more alleles with an increased likelihood of being harmful.

3. The method of claim 2 further comprising:
   d) determining the frequency of a subset of the mutations identified in c) that have significantly decreased frequencies in the aged population, wherein the subset of point mutations are obligatory knockout point mutations;
   e) determining the age-specific decrease in frequency of any of said subset of point mutations; and
   f) comparing the age-specific decrease in frequency with the expected age-specific decrease in frequency of a set of harmful alleles that cause a particular mortal disease, wherein a determination that he age-specific decrease in frequency determined in e) is not significantly different from the expected age-specific decrease in frequency of harmful alleles further indicates that said selected gene carries one or more alleles with an increased likelihood of being harmful.

4. The method of claim 2 further comprising:
   d) identifying a subset of obligatory knockout point mutations in the point mutations identified in c) that have decreased frequencies in the aged population;
   e) determining the frequency of the point mutations identified in d), that are significantly decreased in one or more proband populations, wherein the proband population consists of persons diagnosed with a mortal disease drawn from a common population; and
   e) comparing the frequencies of the subset of point mutations in said selected gene or portion thereof in the young population with the frequencies of said point mutations in said selected gene or portion thereof in the one or more proband populations,
wherein a significant increase in the frequencies of said subset of point mutations in the proband population relative to the young population indicates that said gene carries one or more alleles that confer an increased likelihood of said disease.

5. The method of claim 4, wherein the proband population consists of individuals with early onset disease.

6. A method for identifying total detectable obligatory knockout point mutations in any target region of a genome of a population, wherein said point mutations increase the likelihood of a mortal disease or increase the likelihood of delay or preventing the appearance of a mortal disease, comprising:
   a) separately determining the frequencies of all detectable mutations occurring at a frequency at or above $5 \times 10^{-5}$ in members of a population that comprises subpopulations selected from the group consisting of young, aged, intermediate age, afflicted with disease, afflicted with a disease of early age onset and afflicted with a disease of late age onset; and b) determining the frequencies of each mutation of a) within one or more subpopulations, wherein a decrease in the frequency in the aged population compared to the young population is indicative of an allele that increases the likelihood of a mortal disease, and an increase in frequency in the intermediate or aged population compared to the young population is indicative of an allele that increases the likelihood of preventing or delaying the appearance of a mortal disease.

7. The method of claim 2, wherein said point mutations are identified using a method that comprises:
   a) providing a first pool of DNA fragments comprising a gene or portion thereof, wherein said pool is isolated from a population and contains DNA pooled from 10 to 10,000 individuals;
   b) amplifying a target region of said gene or portion from each of said fragments in a high fidelity polymerase chain reaction (PCR) under conditions suitable to produce double-stranded DNA products that contains, or may be subsequently attached to, a terminal high temperature isomelting domain that is labeled with a detectable label, and wherein the mutant fraction of each PCR-induced mutation among The PCR products is not greater than about $5 \times 10^{-5}$ for a pool created by DNA from 10,000 persons;
   c) melting and reannealing the product of b) under conditions suitable to form duplexed DNA, thereby producing a mixture of wild-type homoduplexes and heteroduplexes that contain point mutations;
   d) separating the heteroduplexes from the homoduplexes based upon the differential melting temperatures of said heteroduplexes and said homoduplexes and recovering the heteroduplexes, thereby producing a second pool of DNA that is enriched in target regions containing point mutations;
   e) amplifying said second pool by high fidelity PCR under conditions where only homoduplexed double-stranded DNA is produced, thereby producing a mixture of homoduplexed DNA containing wild-type target region and homoduplexed DNAs that contain target regions that include point mutations;
   f) resolving from step e) hetero-duplexed DNAs containing larger regions that include point mutations based upon the differential melting temperatures of the DNAs, and recovering the resolved DNAs that contain a target region that includes point mutations; and
   g) determining the sequence of the target region of the recovered DNAs to identify point mutations with the target region.

8. A method for identifying genes that carry one or more alleles with an increased likelihood of being harmful comprising:
   a) identifying in one or more samples two or more point mutations that are found in one or more genes or portions thereof of a population of young individuals, determining the frequency with which each point mutation occurs, and calculating the sum of the frequencies of all point mutations identified for each gene or segment;
   b) identifying in one or more samples two or more point mutations that are found in one or more genes or portions thereof of a population of aged individuals, determining the frequency with which each point mutation occurs, and calculating the sum of the frequencies of all point mutations identified for each gene or segment;
   c) determining the subset of point mutations that are obligatory knock-out point mutations for steps a) and b); and
   d) comparing the sum of the frequencies of obligatory knock-out mutations that are found in a selected gene or portion thereof of the young population with the sum of the frequencies of obligatory knockout point mutations that are found in the same gene or portion thereof of the aged population, wherein a significant decrease in the sum of the frequencies of obligatory knock-out point mutations in the aged population indicates that said selected gene carries one or more alleles with an increased likelihood of being harmful.

9. A method for identifying genes that carry one or more alleles that confer an increased likelihood of mortal disease, comprising:
   a) determining the number and nucleotide sequence identities of all detectable point mutations in a gene or gene segment in a population of young individuals, wherein said gene segment consists of the axons and splice sites of genes that code for proteins, wherein detectable point mutations are selected from the group consisting of: point mutations resulting in amino acid substitutions, small insertions or deletions, termination codons or splice site mutations, in a population of young individuals, and calculating the sum of frequencies of all point mutations determined for each gene or segment;
   b) determining the number and nucleotide sequence identities of all detectable point mutations in a gene or gene segment in a population of aged individuals, wherein said gene segment consists of the exons and splice sites of genes that code for proteins, wherein detectable point mutations are selected from the group consisting of: point mutations resulting in amino acid substitutions, small insertions or deletions, termination codons or splice site mutations, and calculating the sum of the frequencies of all point mutations determined for each gene or segment; and
   c) comparing the sum of the frequencies of the specified type or types of point mutations that are found in a selected gene or segment thereof of the young population calculated in a) with the sum of the frequencies of the specified type or types of point mutations that are found in the same gene or segment thereof of the aged population calculated in b), wherein a statistically significant decrease in the sum of the frequencies of the specified type or types of point mutations associated with a particular gene in the aged population indicates that said selected gene carries one or more alleles that confer an increased likelihood of moral disease.

10. A method for identifying genes that carry one or more alleles that confer an increased likelihood of mortal disease, comprising
    a) determining the number and nucleotide sequence identities of all detectable point mutations in a gene or gene segment in a population of young individuals, wherein the gene segment consists of the exons and splice sites of genes that code for proteins and enumerating the detectable point mutations that are expected to result in a nonfunctional gene product, wherein the point mutations are selected from the group consisting of: small insertions or deletions, termination codons, splice site mutations, gene-inactivating mutation and or any combination thereof, and calculating the sum of the frequencies of all such specified type or types of point mutations determined for each gene or segment;

b) determining the number and nucleotide sequence identities of all detectable point mutations in a gene or gene segment in a population of aged individuals, wherein the gene segment consists of the exons and splice sites of genes that code for proteins and enumerating the detectable point mutations that are expected to result in a nonfunctional gene product, wherein the point mutations are selected from the group consisting of: small insertions or deletions, termination codons splice site mutations, gene-inactivating mutations and any combination thereof, and calculating the sum of the frequencies of all such specified type or types of point mutations determined for each gene or segment;

c) comparing the sum of the frequencies of specified types of point mutations that are found in a selected gene or segment thereof of the young population calculated in a) with the sum of the frequencies of specified type or types of point mutations that are found in the same gene or segment thereof of the aged population calculated in b), wherein a statistically significant decrease in the sum of the frequencies of the specified type or types of point mutations associated with a particular gene in the aged population indicates that said selected gene carries one or more alleles that confer an increased likelihood risk of mortal disease.

11. The method of claim 2 wherein said point mutations are identified by amplifying DNA obtained from the individual members of the population samples and determining the nucleotide sequence of the DNA.

* * * * *

UNITED STATES PATENT AND TRADEMARK OFFICE
CERTIFICATE OF CORRECTION

PATENT NO. : 6,994,962 B1 Page 1 of 1
APPLICATION NO. : 09/503758
DATED : February 7, 2006
INVENTOR(S) : William G. Thilly It is certified that error appears in the above-identified patent and that said Letters Patent is hereby corrected as shown below:

<u>Title page,</u>
Item [54], Title, should read:
-- METHODS OF IDENTIFYING POINT MUTATIONS IN A GENOME THAT CAUSE OR ACCELERATE DISEASE --.

<u>Column 91,</u>
Line 56, delete "deter" and insert -- determining --.

<u>Column 92,</u>
Line 29, delete "he" and insert -- the --.
Line 59, delete "delay" and insert -- delaying --.

<u>Column 93,</u>
Line 23, delete "The" and insert -- the --.
Line 44, delete "larger" and insert -- target --.

<u>Column 94,</u>
Line 20, delete "axons" and insert -- exons --.

Signed and Sealed this

Twentieth Day of June, 2006

JON W. DUDAS
*Director of the United States Patent and Trademark Office*

```
                          SEQUENCE LISTING

<160> NUMBER OF SEQ ID NOS:  3

<210> SEQ ID NO 1
<211> LENGTH: 6
<212> TYPE: DNA
<213> ORGANISM: Homo sapiens

<400> SEQUENCE: 1 gtcgca                                                                    6

<210> SEQ ID NO 2
<211> LENGTH: 6
<212> TYPE: DNA
<213> ORGANISM: Homo sapiens

<400> SEQUENCE: 2 gttgca                                                                    6

<210> SEQ ID NO 3
<211> LENGTH: 78
<212> TYPE: DNA
<213> ORGANISM: Artificial Sequence
<220> FEATURE:
<223> OTHER INFORMATION: Synthetic DNA/RNA chimera
<221> NAME/KEY: modified_base
<222> LOCATION: (17)...(17)
<223> OTHER INFORMATION: 2'-O-methyl adenosine
<221> NAME/KEY: modified_base
<222> LOCATION: (18)...(18)
<223> OTHER INFORMATION: gm
<221> NAME/KEY: modified_base
<222> LOCATION: (19)...(20)
<223> OTHER INFORMATION: cm
<221> NAME/KEY: modified_base
<222> LOCATION: (21)...(21)
<223> OTHER INFORMATION: 2'-O-methyl adenosine
<221> NAME/KEY: modified_base
<222> LOCATION: (22)...(22)
<223> OTHER INFORMATION: gm
<221> NAME/KEY: modified_base
<222> LOCATION: (23)...(23)
<223> OTHER INFORMATION: cm
<221> NAME/KEY: modified_base
<222> LOCATION: (24)...(24)
<223> OTHER INFORMATION: um
<221> NAME/KEY: modified_base
<222> LOCATION: (25)...(26)
<223> OTHER INFORMATION: gm
<221> NAME/KEY: modified_base
<222> LOCATION: (32)...(32)
<223> OTHER INFORMATION: 2'-O-methyl adenosine
<221> NAME/KEY: modified_base
<222> LOCATION: (33)...(33)
<223> OTHER INFORMATION: gm
<221> NAME/KEY: modified_base
<222> LOCATION: (34)...(37)
<223> OTHER INFORMATION: 2'-O-methyl adenosine
<221> NAME/KEY: modified_base
<222> LOCATION: (38)...(39)
<223> OTHER INFORMATION: cm
<221> NAME/KEY: modified_base
```

-continued

```
<222> LOCATION: (40)...(40)
<223> OTHER INFORMATION: um
<221> NAME/KEY: modified_base
<222> LOCATION: (41)...(41)
<223> OTHER INFORMATION: gm
<223> OTHER INFORMATION: (1)...(16), (27)...(31), (42)...(78) DNA
<223> OTHER INFORMATION: (17)...(26), (32)...(41) 2'-O-methyl RNA

<400> SEQUENCE: 3
gggagctttt gctcccagcc agcuggccta gagaaaaccu gaaggttttc cttcaggttt        60
tctctaggcc agctggct                                                     78
```